United States Patent
Xi et al.

(10) Patent No.: US 9,718,841 B2
(45) Date of Patent: Aug. 1, 2017

(54) BICYCLIC PYRAZOLONE COMPOUNDS AND METHODS OF USE

(71) Applicants: CALITOR SCIENCES, LLC, Newbury Park, CA (US); SUNSHINE LAKE PHARMA CO., LTD., Dongguan, Guangdong (CN)

(72) Inventors: Ning Xi, Newbury Park, CA (US); Yanjun Wu, Dongguan (CN)

(73) Assignees: CALITOR SCIENCES, LLC, Newbury Park, CA (US); SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/300,284

(22) PCT Filed: Apr. 16, 2015

(86) PCT No.: PCT/US2015/026062
§ 371 (c)(1),
(2) Date: Sep. 29, 2016

(87) PCT Pub. No.: WO2015/164161
PCT Pub. Date: Oct. 29, 2015

(65) Prior Publication Data
US 2017/0183358 A1 Jun. 29, 2017

Related U.S. Application Data

(60) Provisional application No. 61/982,729, filed on Apr. 22, 2014.

(51) Int. Cl.
| | | |
|---|---|---|
| C07D 498/04 | (2006.01) |
| C07D 471/04 | (2006.01) |
| C07D 487/04 | (2006.01) |
| A61K 31/437 | (2006.01) |
| A61K 31/4439 | (2006.01) |
| A61K 31/444 | (2006.01) |
| A61K 31/5383 | (2006.01) |
| A61K 45/06 | (2006.01) |
| C12N 9/12 | (2006.01) |

(52) U.S. Cl.
CPC .......... *C07D 498/04* (2013.01); *A61K 31/437* (2013.01); *A61K 31/444* (2013.01); *A61K 31/4439* (2013.01); *A61K 31/5383* (2013.01); *A61K 45/06* (2013.01); *C07D 471/04* (2013.01); *C07D 487/04* (2013.01); *C12N 9/12* (2013.01); *C12Y 207/10001* (2013.01)

(58) Field of Classification Search
None
See application file for complete search history.

(56) References Cited

U.S. PATENT DOCUMENTS

| | | | |
|---|---|---|---|
| 7,858,623 B2 * | 12/2010 | Kim .................... | C07D 401/12 514/236.5 |
| 8,030,302 B2 | 10/2011 | Li et al. | |
| 8,088,794 B2 | 1/2012 | Kim et al. | |
| 8,685,983 B2 | 4/2014 | Kim et al. | |
| 8,957,102 B2 | 2/2015 | Kim et al. | |
| 8,969,388 B1 | 3/2015 | Xi et al. | |
| 8,975,282 B2 | 3/2015 | Xi et al. | |
| 9,133,162 B2 | 9/2015 | Xi | |
| 2012/0289509 A1 | 11/2012 | Kim et al. | |
| 2014/0206679 A1 | 7/2014 | Cheng et al. | |
| 2016/0168121 A1 | 6/2016 | Inukai et al. | |

FOREIGN PATENT DOCUMENTS

| | | |
|---|---|---|
| WO | 2013097753 | 7/2013 |
| WO | 2013180949 | 12/2013 |

OTHER PUBLICATIONS

Sai Li et al., Discovery of novel 4-(2-fluorophenoxy)quinoline derivatives bearing 4-oxo-1,4-dihydrocinnoline-3-carboxamide moiety as c-Met kinase inhibitors, Bioorganic & Medicinal Chemistry 2013, vol. 21, Issue 11, p. 2843-2855.
Sai Li et al., Design, synthesis and antitumour activity of bisquinoline derivatives connected by 4-oxy-3-fluoroaniline moiety, European Journal of Medicinal Chemistry, 2013, vol. 64, Issue 6, p. 62-73.
Yasushi Rino et al., Phase II study on the combination of irinotecan plus cisplatin as a second-line therapy in patients with advanced or recurrent gastric cancer, Molecular and Clinical Oncology, 2013, vol. 1, Issue 4, p. 749-752.
ISR of PCT/US2015/026062.
Written Opinion of PCT/US2015/026062.

* cited by examiner

*Primary Examiner* — Timothy R Rozof
(74) *Attorney, Agent, or Firm* — Kam W. Law; Squire Patton Boggs (US) LLP

(57) ABSTRACT

The present invention provides substituted bicyclic pyrazolone compounds, which are used to inhibit or modulate the activity of receptor tyrosine kinases, especially Axl, Mer, c-Met and Ron. The invention also provides pharmaceutical compositions comprising the compound disclosed herein, and a method of preventing, treating or lessening the severity of a proliferative disorder in a patient with the compounds or the pharmaceutical compositions disclosed herein.

19 Claims, No Drawings

BICYCLIC PYRAZOLONE COMPOUNDS AND METHODS OF USE

CROSS-REFERENCE TO RELATED APPLICATIONS

This is a U.S. national stage application of the International Patent Application No. PCT/US2015/026062, filed on Apr. 16, 2015, which claims the benefit of U.S. Provisional Application Ser. No. 61/982,729, filed on Apr. 22, 2014, both of which are incorporated herein by reference in their entirety.

FIELD OF THE INVENTION

This invention relates to novel substituted bicyclic pyrazolone compounds and salts thereof, which are useful in the treatment of proliferative diseases, such as cancers, in mammals. In particular, the invention relates to compounds that inhibit the protein tyrosine kinase activity, resulting in the inhibition of inter- and/or intra-cellular signaling. This invention also relates to a method of using such compounds in the treatment of hyperproliferative diseases in mammals, especially humans, and to pharmaceutical compositions containing such compounds.

BACKGROUND OF THE INVENTION

Protein kinases represent a large family of proteins that play a central role in the regulation of a wide variety of cellular processes. Through regulating an array of signaling pathways, protein kinases control cell metabolism, cell cycle progression, cell proliferation and cell death, differentiation and survival. There are over 500 kinases in the human kinome, and over 150 of these have been shown or are proposed to be involved in the onset and/or progression of various human diseases including inflammatory diseases, cardiovascular diseases, metabolic diseases, neurodegenerative diseases and cancer.

A partial list of such kinases include abl, AATK, ALK, Akt, Axl, bmx, bcr-abl, Blk, Brk, Btk, csk, c-kit, c-Met, c-src, c-fms, CDK1, CDK2, CDK3, CDK4, CDK5, CDK6, CDK7, CDK8, CDK9, CDK10, cRaf1, CSF1R, CSK, DDR1, DDR2, EPHA, EPHB, EGFR, ErbB2, ErbB3, ErbB4, Erk, Fak, fes, FER, FGFR1, FGFR2, FGFR3, FGFR3, FGFR4, FGFR5, Fgr, flt-1, Fps, Frk, Fyn, GSG2, GSK, Hck, LLK, INSRR, IRAK4, ITK, IGF-1R, INS-R, Jak, KSR1, KDR, LMTK2, LMTK3, LTK, Lck, Lyn, MATK, MERTK (Mer), MLTK, MST1R (Ron), MUSK, NPR1, NTRK, MEK, MET, PLK4, PTK, p38, PDGFR, PIK, PKC, PYK2, RET, ROR1, ROR2, RYK, ros, SGK493, SRC, SRMS, STYK1, SYK, TEC, TEK, TEX14, TNK1, TNK2, TNNI3K, TXK, TYK2, Tyro-3, tie, tie2, TRK, Yes, and Zap 70.

Protein tyrosine kinases are a subclass of protein kinase. They also may be classified as growth factor receptor (e.g., Axl, Mer, c-Met (HGFR), Ron, EGFR, PDGFR and FGFR) or non-receptor (e.g., c-src and bcr-abl) kinases. Receptor tyrosine kinases are transmembrane proteins that possess an extracellular binding domain for growth factors, a transmembrane domain, and an intracellular portion that functions as a kinase to phosphorylate a specific tyrosine residue in proteins. Abnormal expression or activity of protein kinases has been directly implicated in the pathogenesis of myriad human cancers.

Axl and Mer are both members of the TAM receptor family, which also includes Tyro3. All three are activated by a common ligand, Growth Arrest-specific protein 6 (Gas6), and they ordinarily play an embryonic developmental role in cell survival, migration and differentiation. The TAM receptors are characterized by a combination of two immunoglobulin-like domains and dual fibronectin type III repeats in the extracellular region and a cytoplasmic kinase domain (Trevor et al., "The anticoagulation factor protein S and its relative, Gas6, are ligands for the Tyro3/Axl family of receptor tyrosine kinases" *Cell,* 1995, 80, 661-670; Varnum et al., "Axl receptor tyrosine kinase stimulated by the vitamin K-dependent protein encoded by growth-arrest-specific gene 6" *Nature,* 1995, 373, 623-626).

Axl signaling is required to maintain EMT-associated features including invasiveness and metastasis (Linger et al., "TAM receptor tyrosine kinases: biologic functions, signaling, and potential therapeutic targeting in human cancer" *Adv. Cancer Res.,* 2008, 100, 35-83). Axl overexpression and signaling has been implicated in several human malignancies, such as colon, breast, glioma, thyroid, gastric, melanoma, lung cancer, and in renal cell carcinoma (RCC). A more detailed role of Axl biology has been proven in glioma, where loss of Axl signaling diminished glioma tumor growth, and in breast cancer, where Axl drive cell migration, tube formation, neovascularization and tumor growth. Axl has been shown to play multiple roles in tumorigenesis and that therapeutic antibodies against Axl may block Axl functions not only in malignant tumor cells but also in the tumor stroma. The additive effect of Axl inhibition with anti-VEGF suggests that blocking Axl function could be an effective approach for enhancing antiangiogenic therapy (Li et al., "Axl as a potential therapeutic target in cancer: role of Axl in tumor growth, metastasis and angiogenesis" *oncogene,* 2009, 28, 3442-3455; and Linger et al., "TAM receptor tyrosine kinases: biologic functions, signaling, and potential therapeutic targeting in human cancer" *Adv. Cancer Res.,* 2008, 100, 35-83).

High levels of Axl expression have been correlated with poor survival in many types of cancer, including breast cancer (Christine et al., "Axl is an essential epithelial-to-mesenchymal transition-induced regulator of breast cancer metastasis and patient survival" *Proc. Natl. Acad. Sci. USA,* 2010, 107(3), 1124-1129), acute myeloid leukemia (Amer. Soc. Hematol. Annual Meeting, San Diego 2011), glioblastoma multiforme (Markus et al., "Axl and growth arrest-specific gene 6 are frequently overexpressed in human gliomas and predict poor prognosis in patients with glioblastoma multiforme" *Clin. Cancer Res.,* 2008, 14, 130-138) and osteosarcoma (Han et al., "Gas6/Axl mediates tumor cell apoptosis, migration and invasion and predicts the clinical outcome of osteosarcoma patients" *Biochem. Biophys. Res. Commun.,* 2013, 435(3), 493-500). In addition, activation of Axl kinase has been identified as one mechanism by which lung cancers can develop resistance to therapies targeting EGFR, such as Tarceva (erlotinib) (Zhang et al., "Activation of the Axl kinase causes resistance to EGFR-targeted therapy in lung cancer" *Nat. Genet.,* 2012, 44(8), 852-860).

Mer expression correlates with disease progression. It has been found that Mer expression was high in metastatic melanomas (Jennifer et al., "MERTK receptor tyrosine kinase is a therapeutic target in melanoma" *J. Clin. Invest.,* 2013, 123(5), 2257-2267), and activation of Mer promotes invasion and survival in glioblastoma multiforme (Wang et al., "Mer receptor tyrosine kinase promotes invasion and survival in glioblastoma multiforme" *Oncogene,* 2013, 32, 872-882). Studies also indicated a role for Mer in acute lymphoblastic leukemia (ALL). Mer is ectopically expressed in at least 50% of pediatric T-cell ALL samples as well as in pre-B ALL samples (Graham et al., "Ectopic expression of the proto-oncogene Mer in pediatric T-cell acute lymphoblastic leukemia" *Clin. Cancer Res.,* 2006, 12(9), 2662-2669). Thus, Mer receptor tyrosine kinase is proposed to be a therapeutic target for various solid or hematological malignancies.

Recently a study showed that Mer and Axl were frequently overexpressed and activated in NSCLC cell lines. Ligand-dependent Mer or Axl activation stimulated MAPK, AKT and FAK signaling pathways indicating roles for these RTKs in multiple oncogenic processes. Abnormal expression and activation of Axl knockdown also improved in vitro NSCLC sensitivity to chemotherapeutic agents by promoting apoptosis. When comparing the effects of Mer and Axl knockdown, Mer inhibition exhibited more complete blockade of tumor growth while Axl knockdown more robustly improved chemosensitivity. These results indicated that Mer and Axl play complementary and overlapping roles in NSCLC and suggest that treatment strategies targeting both RTKs may be more effective than singly-targeted agents. Therefore, inhibition of both Axl and Mer is potentially a therapeutic strategy to target cancer cells (Rachel et al., "Mer or Axl Receptor Tyrosine Kinase inhibition promotes apoptosis, blocks growth, and enhances chemosensitivity of human non-small cell lung cancer" *Oncogene,* 2013, 32(29), 3420-3431).

c-Met, also referred to as hepatocyte growth factor receptor (HGFR), is expressed predominantly in epithelial cells but has also been identified in endothelial cells, myoblasts, hematopoietic cells and motor neurons. The natural ligand for c-Met is hepatocyte growth factor (HGF), also known as scatter factor (SF). In both embryos and adults, activated c-Met promotes a morphogenetic program, known as invasive growth, which induces cell spreading, the disruption of intercellular contacts, and the migration of cells towards their surroundings (Peschard et al., "From Tpr-Met to Met, tumorigenesis and tubes" *oncogene,* 2007, 26, 1276-1285; and Christine et al., "MET receptor tyrosine kinase as a therapeutic anticancer target" *Cancer Letters,* 2009, 280(1), 1-14).

A wide variety of human malignancies exhibit sustained c-Met stimulation, overexpression or mutation, including carcinomas of the breast, liver, lung, ovary, kidney, thyroid, colon, glioblastomas and prostate, etc. c-Met is also implicated in atherosclerosis and lung fibrosis. Invasive growth of certain cancer cells is drastically enhanced by tumor-stromal interactions involving the HGF/c-Met pathway. Thus, extensive evidence that c-Met signaling is involved in the progression and spread of several cancers and an enhanced understanding of its role in disease have generated considerable interest in c-Met as major targets in cancer drug development (Cristina et al., "Molecular cancer therapy: Can our expectation be MET" *Eur. J. Cancer,* 2008, 44(5) 641-651; and Peruzzi et al., "Targeting the c-Met signaling pathway in cancer" *Clin. Cancer Res.,* 2006, 12(12), 3657-3660).

Ron (MST1R, recepteur d'origine nantais), the other member of the MET family, is a receptor tyrosine kinase for the ligand macrophage-stimulating protein (MSP, also known as MST1, and hepatocyte growth factor-like (HGFL) protein), which is associated with in vitro and in vivo cell dissociation, motility and matrix invasion—all of which are surrogate markers of an aggressive cancer phenotype with metastatic potential. Ron mediates oncogenic phenotypes in lung, thyroid, pancreas, prostate, colon and breast cancer cells and predicts a poor prognosis in human breast cancer. Co-expression of Ron with Met and the induction of Ron expression by HGF-Met signaling have both been described in hepatocellular carcinoma. Furthermore, co-expression of Met and Ron portends a worse prognosis in ovary, breast and bladder cancers. Given Ron and Met signaling redundancy, it is possible that resistance to Met inhibition is mediated by Ron signaling (Catenacci et al., "RON (MST1R) is a novel prognostic marker and therapeutic target for gastroesophageal adenocarcinoma" *Cancer Biol. Ther.,* 2011, 12(1), 9-46).

The roles of MSP-Ron signaling axis in cancer pathogenesis has also been extensively studied in various model systems. Both in vitro and in vivo evidence has revealed that MSP-Ron signaling is important for the invasive growth of different types of cancers. Aberrant Ron activation, which is induced by overexpression of protein and the generation of oncogenic isoforms and is indicated by the persistent activation of multi-intracellular signaling cascades, occurs in various types of cancers. Ron signaling is also necessary for cancer cell growth and survival. These features render Ron as a drug target for cancer therapy (Yao et al., "MSP-RON signalling in cancer: pathogenesis and therapeutic potential" *Nat. Rev. Cancer,* 2013, 13(7), 466-481).

It is widely known that cancer cells employ multiple mechanisms to evade tightly regulated cellular processes such as proliferation, apoptosis and senescence. Thus, most tumors can escape from the inhibition of any single kinase. System-wide analysis of tumors identified receptor tyrosine kinase (RTK) coactivation as an important mechanism by which cancer cells achieve chemoresistance. One of the strategies to overcome RTK coactivation may involve therapeutically targeting multiple RTKs simultaneously in order to shut down oncogenic RTK signaling and overcome compensatory mechanisms (Alexander et al., "Receptor tyrosine kinase coactivation metworks in cancer" *Cancer Res.,* 2010, 70, 3857-3860). Anti-tumor approaches in targeting Axl, Mer, c-Met and/or Ron signaling may circumvent the ability of tumor cells to overcome Axl, Mer (MERTK), c-Met (HGFR) and/or Ron (MST1R) inhibition alone and thus may represent improved cancer therapeutics.

SUMMARY OF THE INVENTION

The present invention provides substituted bicyclic pyrazolone compounds which are useful as multiple function inhibitors, capable of inhibiting, for example, Axl, Mer (MERTK), c-Met (HGFR) and/or Ron (MST1R). The invention also provides methods of making the compounds, methods of using such compounds in the treatment of diseases and conditions proliferative diseases in mammals and pharmaceutical compositions comprising such compounds.

Specifically, in one aspect, provided herein is a compound having Formula (I):

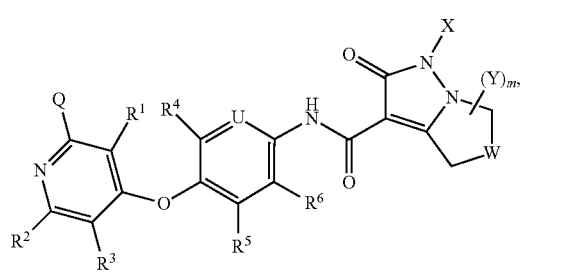

or a stereoisomer, a tautomer, an N-oxide, a solvate, a metabolite, a pharmaceutically acceptable salt or a prodrug thereof, wherein:

Q is H, $OR^a$, $NR^aR^b$, —C(=O)$NR^aR^b$, —N($R^c$)C(=O)$R^d$, —N($R^c$)C(=O)$OR^a$ or —N($R^c$)C(=O)$NR^aR^b$;

U is $CR^7$ or N, provided that when U is N, the compound is not 2-oxo-1-phenyl-N-(5-((2-(pyrrolidine-1-carboxamido)pyridin-4-yl)oxy)pyridin-2-yl)-2,4,6,7-tetrahydro-1H-pyrazolo[5,1-c][1,4]oxazine-3-carboxamide or 1-(buta-1,3-dien-2-yl)-2-oxo-N-(5-((2-(pyrrolidine-1-carboxamido)pyridin-4-yl)oxy)pyridin-2-yl)-1,2,4,5,6,7-hexahydropyrazolo[1,5-a]pyrazine-3-carboxamide;

X is H, $C_1$-$C_6$ alkyl, $C_3$-$C_8$ alkenyl, $C_3$-$C_8$ alkynyl, $C_3$-$C_8$ cycloalkyl, —($C_1$-$C_4$ alkylene)-($C_3$-$C_8$ cycloalkyl), 3-8 membered heterocyclyl, —($C_1$-$C_4$ alkylene)-(3-8 membered heterocyclyl), $C_6$-$C_{10}$ aryl, —($C_1$-$C_4$ alkylene)-($C_6$-$C_{10}$ aryl), 5-10 membered heteroaryl or —($C_1$-$C_4$ alkylene)-(5-10 membered heteroaryl), wherein each of the $C_1$-$C_6$ alkyl, $C_3$-$C_8$ alkenyl, $C_3$-$C_8$ alkynyl, $C_3$-$C_8$ cycloalkyl, —($C_1$-$C_4$ alkyl ene)-($C_3$-$C_8$ cycloalkyl), 3-8 membered heterocyclyl, —($C_1$-$C_4$ alkylene)-(3-8 membered heterocyclyl), $C_6$-$C_{10}$ aryl, —($C_1$-$C_4$ alkylene)-($C_6$-$C_{10}$ aryl), 5-10 membered heteroaryl and —($C_1$-$C_4$ alkylene)-(5-10 membered heteroaryl) is optionally substituted with 1, 2, 3, 4 or 5 substituents independently selected from F, Cl, Br, CN, $C_1$-$C_6$ alkyl, $C_2$-$C_6$ alkenyl, $C_2$-$C_6$ alkynyl, $OR^a$, $NR^aR^b$, alkylene)-$OR^a$ and —($C_1$-$C_4$ alkylene)-$NR^aR^b$;

each Y is independently $C_1$-$C_6$ alkyl, $C_2$-$C_6$ alkenyl, $C_2$-$C_6$ alkynyl, $C_3$-$C_8$ cycloalkyl, —($C_1$-$C_4$ alkylene)-($C_3$-$C_8$ cycloalkyl), 3-8 membered heterocyclyl, —($C_1$-$C_4$ alkylene)-(3-8 membered heterocyclyl), $C_6$-$C_{10}$ aryl, —($C_1$-$C_4$ alkylene)-($C_6$-$C_{10}$ aryl), 5-10 membered heteroaryl, —($C_1$-$C_4$ alkylene)-(5-10 membered heteroaryl), $OR^a$, $NR^aR^b$, —($C_1$-$C_4$ alkylene)-$OR^a$ or —($C_1$-$C_4$ alkylene)-$NR^aR^b$;

m is 0, 1, 2, 3, 4;

W is —$(CH_2)_n$—, —$(CH_2)_nO$—, —$(CH_2)$—NH— or —$(CH_2)$—S—, wherein n is 0, 1, 2, 3 or 4;

each of $R^1$, $R^2$, $R^3$, $R^4$, $R^5$, $R^6$ and $R^7$ is independently H, F, Cl, Br, CN, $N_3$, $OR^a$, $C_1$-$C_6$ alkyl, $C_1$-$C_6$ haloalkyl, $C_2$-$C_6$ alkenyl or $C_2$-$C_6$ alkynyl;

each of $R^a$, $R^b$ and $R^c$ is independently H, $C_1$-$C_6$ alkyl, $C_1$-$C_6$ haloalkyl, $C_3$-$C_6$ cycloalkyl, —($C_1$-$C_4$ alkylene)-($C_3$-$C_6$ cycloalkyl), 3-6 membered heterocyclyl, —($C_1$-$C_4$ alkylene)-(3-6 membered heterocyclyl), $C_6$-$C_{10}$ aryl, —($C_1$-$C_4$ alkylene)-($C_6$-$C_{10}$ aryl), 5-10 membered heteroaryl or —($C_1$-$C_4$ alkylene)-(5-10 membered heteroaryl), or $R^a$ and $R^b$ taken together with the nitrogen atom to which they are attached form a 3-8 membered heterocyclic ring, wherein each of the $C_1$-$C_6$ alkyl, $C_1$-$C_6$ haloalkyl, $C_3$-$C_6$ cycloalkyl, —($C_1$-$C_4$ alkylene)-($C_3$-$C_6$ cycloalkyl), 3-6 membered heterocyclyl, —($C_1$-$C_4$ alkylene)-(3-6 membered heterocyclyl), $C_6$-$C_{10}$ aryl, —($C_1$-$C_4$ alkylene)-($C_6$-$C_{10}$ aryl), 5-10 membered heteroaryl, —($C_1$-$C_4$ alkylene)-(5-10 membered heteroaryl) and 3-8 membered heterocyclic ring is optionally substituted with 1, 2, 3 or 4 substituents independently selected from F, Cl, CN, $N_3$, OH, $NH_2$, $C_1$-$C_6$ haloalkyl, $C_1$-$C_6$ alkoxy and $C_1$-$C_6$ alkylamino; and $R^d$ is H, $C_1$-$C_6$ alkyl, $C_3$-$C_8$ cycloalkyl, —($C_1$-$C_4$ alkylene)-($C_3$-$C_8$ cycloalkyl), 3-8 membered heterocyclyl, —($C_1$-$C_4$ alkylene)-(3-8 membered heterocyclyl), $C_6$-$C_{10}$ aryl, —($C_1$-$C_4$ alkylene)-($C_6$-$C_{10}$ aryl), 5-10 membered heteroaryl or —($C_1$-$C_4$ alkylene)-(5-10 membered heteroaryl), wherein each of the $C_1$-$C_6$ alkyl, $C_3$-$C_8$ cycloalkyl, —($C_1$-$C_4$ alkylene)-($C_3$-$C_8$ cycloalkyl), 3-8 membered heterocyclyl, —($C_1$-$C_4$ alkylene)-(3-8 membered heterocyclyl), $C_6$-$C_{10}$ aryl, —($C_1$-$C_4$ alkylene)-($C_6$-$C_{10}$ aryl), 5-10 membered heteroaryl and —($C_1$-$C_4$ alkylene)-(5-10 membered heteroaryl) is optionally substituted with 1, 2, 3 or 4 substituents independently selected from F, Cl, Br, CN, $OR^a$, $NR^aR^b$, $C_1$-$C_6$ alkyl, $C_2$-$C_6$ alkenyl, $C_2$-$C_6$ alkynyl, —($C_1$-$C_4$ alkylene)-$OR^a$ and —($C_1$-$C_4$ alkylene)-$NR^aR^b$.

In one embodiment, Q is $NR^aR^b$, —C(=O)$NR^aR^b$, —N($R^c$)C(=O)$R^d$ or —N($R^c$)C(=O)$NR^aR^b$.

In another embodiment, X is $C_1$-$C_4$ alkyl, $C_3$-$C_6$ alkenyl, $C_3$-$C_6$ alkynyl, $C_3$-$C_6$ cycloalkyl, —($C_1$-$C_2$ alkylene)-($C_3$-$C_6$ cycloalkyl), phenyl or —($C_1$-$C_2$ alkylene)-phenyl, wherein each of the $C_1$-$C_4$ alkyl, $C_3$-$C_6$ alkenyl, $C_3$-$C_6$ alkynyl, $C_3$-$C_6$ cycloalkyl, —($C_1$-$C_2$ alkylene)-($C_3$-$C_6$ cycloalkyl), phenyl and —($C_1$-$C_2$ alkylene)-phenyl is optionally substituted with 1, 2, 3, 4 or 5 substituents independently selected from F, Cl, Br, CN, $C_1$-$C_4$ alkyl, $C_2$-$C_4$ alkenyl, $C_2$-$C_4$ alkynyl, $OR^a$, $NR^aR^b$, —($C_1$-$C_2$ alkylene)-$OR^a$ and —($C_1$-$C_2$ alkylene)-$NR^aR^b$.

In another embodiment, each Y is independently $C_1$-$C_6$ alkyl, $C_2$-$C_6$ alkenyl, $C_2$-$C_6$ alkynyl, $C_3$-$C_6$ cycloalkyl, —($C_1$-$C_2$ alkylene)-($C_3$-$C_6$ cycloalkyl), 3-6 membered heterocyclyl, —($C_1$-$C_2$ alkylene)-(3-6 membered heterocyclyl), phenyl, —($C_1$-$C_2$ alkylene)-phenyl, 5-6 membered heteroaryl, —($C_1$-$C_2$ alkylene)-(5-6 membered heteroaryl), $OR^a$, $NR^aR^b$, —($C_1$-$C_2$ alkylene)-$OR^a$ or —($C_1$-$C_2$ alkylene)-$NR^aR^b$; m is 0, 1 or 2.

In another embodiment, W is —$(CH_2)_n$—, —$(CH_2)_nO$— or —$(CH_2)$—NH—, wherein n is 0, 1 or 2.

In another embodiment, each of $R^1$, $R^2$, $R^3$, $R^4$, $R^5$, $R^6$ and $R^7$ is independently H, F, Cl, Me or OMe.

In another embodiment, each of $R^a$, $R^b$ and $R^c$ is independently H, $C_1$-$C_4$ alkyl, $C_1$-$C_4$ haloalkyl, $C_3$-$C_6$ cycloalkyl, —($C_1$-$C_2$ alkylene)-($C_3$-$C_6$ cycloalkyl), 3-6 membered heterocyclyl or —($C_1$-$C_2$ alkylene)-(3-6 membered heterocyclyl), or $R^a$ and $R^b$ taken together with the nitrogen atom to which they are attached form a 3-8 membered heterocyclic ring, wherein each of the $C_1$-$C_4$ alkyl, $C_1$-$C_4$ haloalkyl, $C_3$-$C_6$ cycloalkyl, —($C_1$-$C_2$ alkylene)-($C_3$-$C_6$ cycloalkyl), 3-6 membered heterocyclyl, —($C_1$-$C_2$ alkylene)-(3-6 membered heterocyclyl) and 3-8 membered heterocyclic ring is optionally substituted with 1, 2, 3 or 4 substituents independently selected from F, Cl, CN, $N_3$, OH, $NH_2$, $C_1$-$C_3$ haloalkyl, $C_1$-$C_3$ alkoxy and $C_1$-$C_3$ alkylamino.

In one embodiment, $R^d$ is H, $C_1$-$C_4$ alkyl, $C_3$-$C_6$ cycloalkyl, —($C_1$-$C_2$ alkylene)-($C_3$-$C_6$ cycloalkyl), 3-6 membered heterocyclyl or —($C_1$-$C_2$ alkylene)-(3-6 membered heterocyclyl), wherein each of the $C_1$-$C_4$ alkyl, $C_3$-$C_6$ cycloalkyl, —($C_1$-$C_2$ alkylene)-($C_3$-$C_6$ cycloalkyl), 3-6 membered heterocyclyl and —($C_1$-$C_2$ alkylene)-(3-6 membered heterocyclyl) is optionally substituted with 1, 2, 3 or 4 substituents independently selected from F, CN, $OR^a$, $NR^aR^b$, $C_1$-$C_4$ alkyl, $C_2$-$C_4$ alkenyl, $C_2$-$C_4$ alkynyl, —($C_1$-$C_2$ alkylene)-$OR^a$ and —($C_1$-$C_2$ alkylene)-$NR^aR^b$.

In another embodiment, Q is:

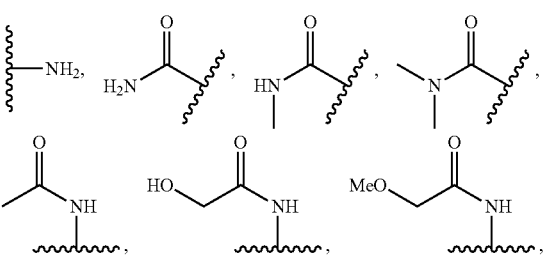

-continued
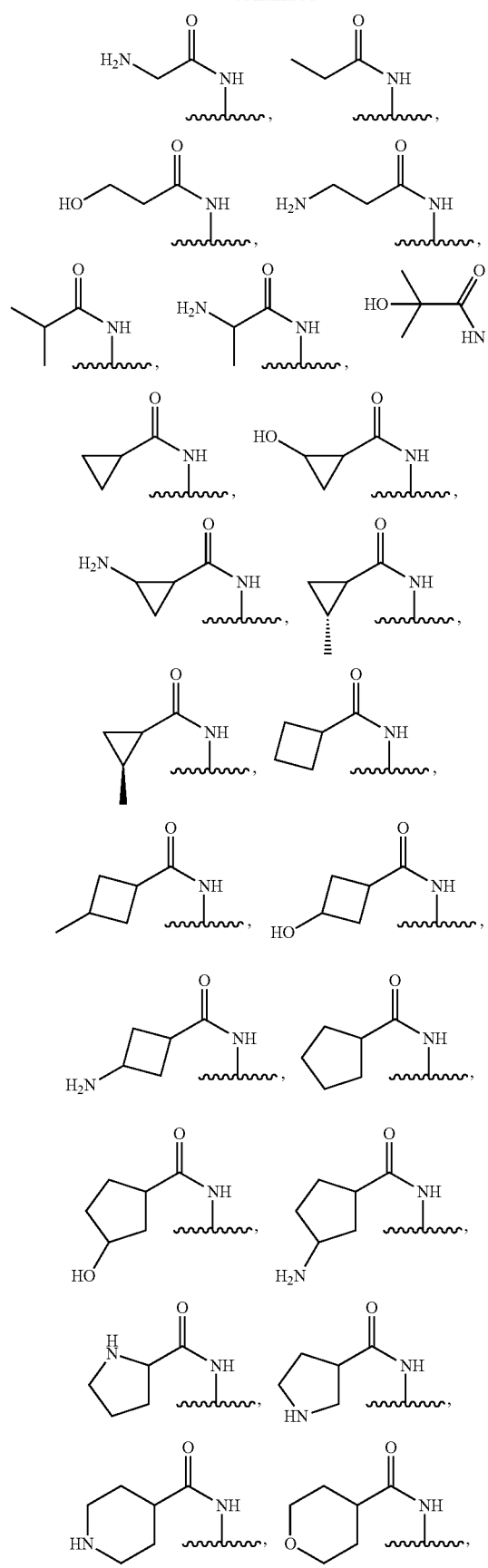
-continued
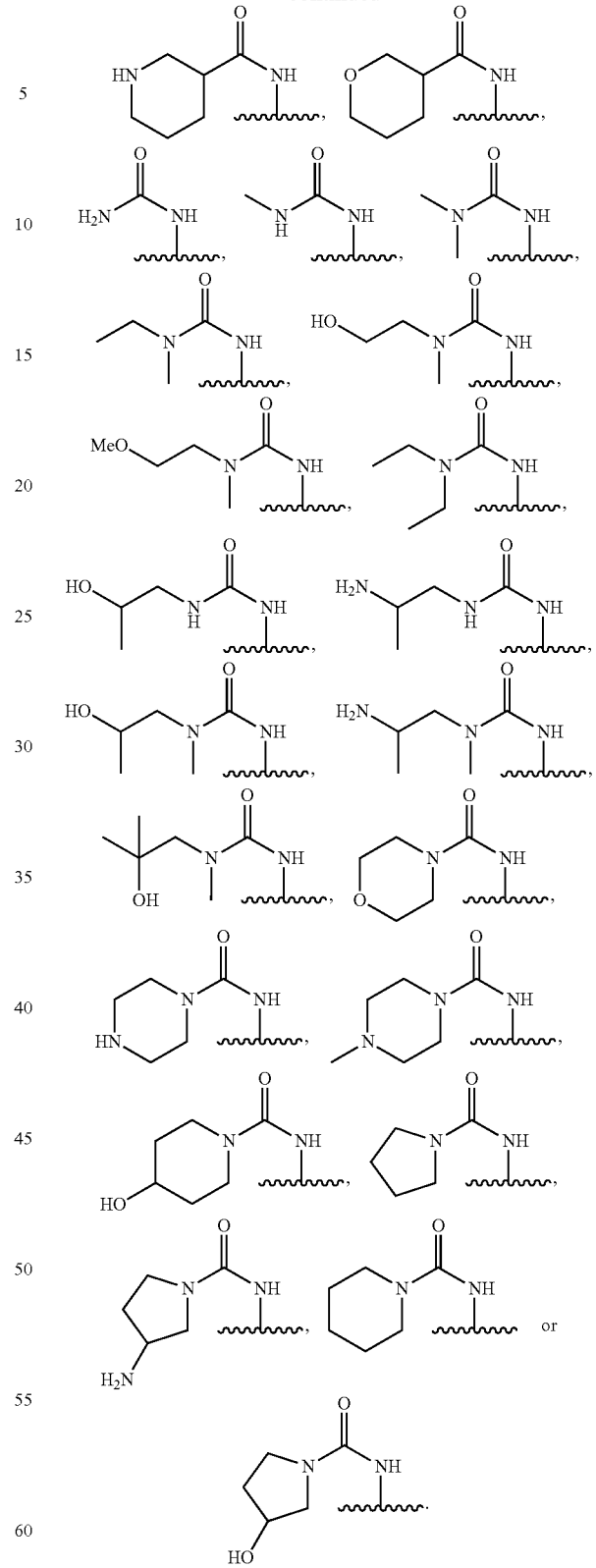
In another aspect, provided herein is a pharmaceutical composition comprising the compound disclosed herein, and a pharmaceutically acceptable excipient, carrier, adjuvant, vehicle or a combination thereof In one embodiment, the pharmaceutical composition disclosed herein further comprising therapeutic selected from the group consisting of chemotherapeutic agents, anti-proliferative agents, agents for treating atherosclerosis, agents for treating lung fibrosis and combinations thereof.

In one embodiment, the pharmaceutical composition disclosed herein is chlorambucil, melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednisone, dexamethasone, methylprednisolone, thalidomide, interferon alfa, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximabvedotin, catumaxomab, cetuximab, denosumab, gemtuzumab, ipilimumab, nimotuzumab, ofatumumab, panitumumab, ramucirumab, rituximab, tositumomab, trastuzumab or a combination thereof.

In another aspect, provided herein is a method of preventing, treating or lessening the severity of a proliferative disease in a patient by administering to the patient with a therapeutically effective amount of the compound or the pharmaceutical composition disclosed herein.

In one embodiment, the proliferative disease is colon cancer, rectal cancer, gastric cancer, gastric adenocarcinoma, pancreatic cancer, bladder cancer, gallbladder cancer, breast cancer, kidney cancer, renal cell carcinoma, liver cancer, hepatocellular carcinoma, lung cancer, skin cancer, melanoma, thyroid cancer, osteosarcoma, soft tissue sarcoma, a cancer of the head and neck, a cancer of the central nervous system, glioma, glioblastomas, ovarian cancer, uterine cancer, endometrial carcinoma, prostate cancer, acute myeloid leukemia or acute lymphoblastic leukemia, or metastasis thereof.

In another embodiment, the proliferative disease is atherosclerosis or lung fibrosis.

In another aspect, provided herein is the compound or the pharmaceutical composition disclosed herein for use in preventing, treating or lessening the severity of a proliferative disease in a patient.

In another aspect, provided herein is the use of the compound or the pharmaceutical composition disclosed herein in the manufacture of a medicament for preventing, treating or lessening the severity of a proliferative disease in a patient.

In another aspect, provided herein is a method of inhibiting or modulating the activity of a protein kinase in a biological sample with the compound and the pharmaceutical composition disclosed herein.

In one embodiment, the protein kinase is a receptor tyrosine kinase.

In one embodiment, the receptor tyrosine kinase is Axl, Mer, c-Met, Ron or a combination thereof.

In another aspect, provided herein are methods for preparation, separation and purification of the compounds represented by Formula (I).

Biological test results indicate that the compounds provided herein can be used as preferable inhibitors of Axl, Mer, c-Met and Ron.

Any embodiment disclosed herein can be combined other embodiments as long as they are not contradictory to one another, even though the embodiments are described under different aspects of the invention. In addition, any technical feature in one embodiment can be applied to the corresponding technical feature in other embodiment as long as they are not contradictory to one another, even though the embodiments are described under different aspects of the invention.

The foregoing merely summarizes certain aspects of the invention and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in Sorrell et al., "Organic Chemistry", University Science Books, Sausalito: 1999, and Smith et al., "March's Advanced Organic Chemistry", John Wiley & Sons, New York: 2007, all of which are incorporated by reference in their entireties.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

A weight percent (wt. %) of a component, unless specifically stated to the contrary, is based on the total weight of the formulation or composition in which the component is included.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "comprising" is meant to be open ended, including the indicated component but not excluding other elements.

The term "stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

The term "chiral" refers to molecules which have the property of non-superimposability of the mirror image partner, while the term "achiral" refers to molecules which are superimposable on their mirror image partner.

The term "enantiomers" refers to two stereoisomers of a compound which are non-superimposable mirror images of one another.

The term "diastereomer" refers to a stereoisomer with two or more centers of chirality and whose molecules are not mirror images of one another. Diastereomers have different physical properties, e.g. melting points, boiling points, spectral properties or biological activities. Mixture of diastereomers may separate under high resolution analytical procedures such as electrophoresis and chromatography such as HPLC.

Stereochemical definitions and conventions used herein generally follow Parker et al., McGraw-Hill Dictionary of Chemical Terms (1984) McGraw-Hill Book Company, New York and Eliel et al., "Stereochemistry of Organic Compounds", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); *Principles of Asymmetric Synthesis* ($2^{nd}$ Ed. Robert et al., Elsevier, Oxford, U K, 2012); Eliel et al., Stereochemistry of Carbon Compounds (McGraw-Hill, N Y, 1962); and Wilen et al., Tables of Resolving Agents and Optical Resolutions p. 268 (E. L. Eliel, Ed., Univ. of Notre Dame Press, Notre Dame, Ind., 1972). Chiral Separation Techniques: A Practical Approach (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) includes interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pridin-4(1H)-one tautomers. Unless otherwise state, all tautomeric forms of the compounds disclosed herein are within the scope of the invention.

The term "prodrug" as used herein, represents a compound that is transformed in vivo into a compound of Formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., Pro-drugs as Novel Delivery Systems, Vol. 14, A.C.S. Symposium Series; Roche et al., Bioreversible Carriers in Drug Design, American Pharmaceutical Association and Pergamon Press, 1987; Rautio et al., Prodrugs: Design and Clinical Applications, *Nat. Rev. Drug Discovery*, 2008, 7, 255-270, and Hecker et al., Prodrugs of Phosphates and Phosphonates, *J. Med. Chem.*, 2008, 51, 2328-2345, all of which are incorporated herein by reference.

A "metabolite" refers to a product produced through metabolism in the body of a specified compound or salt thereof. The metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

A "pharmaceutically acceptable salt" refers to organic or inorganic salts of a compound disclosed herein. The pharmaceutically acceptable salts are well known in the art. For example, Berge et al., describe pharmaceutically acceptable salts in detail in *J. Pharm. Sci.*, 1977, 66, 1-19, which is incorporated herein by reference. Some non-limiting examples of the pharmaceutically acceptable salt include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid.

Other examples of the pharmaceutically acceptable salt include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Pharmaceutically acceptable salts derived from appropriate bases include alkali metal, alkaline earth metal, ammonium and $N^+(C_1\text{-}C_4\text{ alkyl})_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further examples of the pharmaceutically acceptable salt include, when appropriate, nontoxic ammonium, quaternary ammonium, and amine cations formed using counterions such as halide, hydroxide, carboxylate, sulfate, phosphate, nitrate, $C_1\text{-}C_8$ sulfonate and aryl sulfonate.

A "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As described herein, compounds disclosed herein may optionally be substituted with one or more substituents, such as those illustrated below, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

At various places in the present specification, substituents of compounds disclosed herein are disclosed in groups or in ranges. It is specifically intended that the invention include each and every individual subcombination of the members of such groups and ranges. For example, the term "$C_1\text{-}C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms, wherein the alkyl radical may be optionally substituted independently with one or more substituents described below. Unless otherwise specified, the alkyl group contains 1-20 carbon atoms. In one embodiment, the alkyl group contains 1-12 carbon atoms. In another embodiment, the alkyl group contains 1-6 carbon atoms. In still another embodiment, the alkyl group contains 1-4 carbon atoms. In yet another embodiment, the alkyl group contains 1-3 carbon atoms.

Some non-limiting examples of the alkyl group include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In one embodiment, the alkylene group contains 1-6 carbon atoms. In another embodiment, the alkylene group contains 1-4 carbon atoms. In still another embodiment, the alkylene group contains 1-3 carbon atoms. In yet another embodiment, the alkylene group contains 1-2 carbon atoms. The alkylene group is exemplified by methylene (—$CH_2$—), ethylene (—$CH_2CH_2$—), isopropylene (—$CH(CH_3)CH_2$—), and the like.

The term "alkenyl" refers to a linear or branched-chain monovalent hydrocarbon radical of 2 to 12 carbon atoms with at least one site of unsaturation, i.e., a carbon-carbon, sp2 double bond, wherein the alkenyl radical may be optionally substituted independently with one or more substituents described herein, and includes radicals having "cis" and "trans" orientations, or alternatively, "E" and "Z" orientations. In one embodiment, the alkenyl group contains 2-8 carbon atoms. In another embodiment, the alkenyl group contains 2-6 carbon atoms. In still another embodiment, the alkenyl group contains 2-4 carbon atoms. Some non-limiting examples of the alkenyl group include ethylenyl or vinyl (—CH=$CH_2$), allyl (—$CH_2$CH=$CH_2$), and the like.

The term "alkynyl" refers to a linear or branched-chain monovalent hydrocarbon radical of 2 to 12 carbon atoms with at least one site of unsaturation, i.e., a carbon-carbon, sp triple bond, wherein the alkynyl radical may be optionally substituted independently with one or more substituents described herein. In one embodiment, the alkynyl group contains 2-8 carbon atoms. In another embodiment, the alkynyl group contains 2-6 carbon atoms. In still another embodiment, the alkynyl group contains 2-4 carbon atoms. Some non-limiting examples of the alkynyl group include ethynyl (—C≡CH), propynyl (propargyl, —$CH_2$C≡CH), —C≡C—$CH_3$, and the like.

The term "alkoxy" refers to an alkyl group, as previously defined, attached to the principal carbon atom through an oxygen atom. Unless otherwise specified, the alkoxy group contains 1-12 carbon atoms. In one embodiment, the alkoxy group contains 1-6 carbon atoms. In another embodiment, the alkoxy group contains 1-4 carbon atoms. In still another embodiment, the alkoxy group contains 1-3 carbon atoms. The alkoxy radical may be optionally substituted independently with one or more substituents described herein.

Some non-limiting examples of alkoxy groups include methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), 1-pentoxy (n-pentoxy, —$OCH_2CH_2CH_2CH_2CH_3$), 2-pentoxy (—$OCH(CH_3)CH_2CH_2CH_3$), 3-pentoxy (—$OCH(CH_2CH_3)_2$), 2-methyl-2-butoxy (—$OC(CH_3)_2CH_2CH_3$), 3-methyl-2-butoxy (—$OCH(CH_3)CH(CH_3)_2$), 3-methyl-1-butoxy (—$OCH_2CH_2CH(CH_3)_2$), 2-methyl-1-butoxy (—$OCH_2CH(CH_3)CH_2CH_3$), and the like.

The term "haloalkyl", "haloalkenyl" or "haloalkoxy" refers to alkyl, alkenyl, or alkoxy, as the case may be, substituted with one or more halogen atoms.

The term "carbocycle", "carbocyclyl" or "carbocyclic ring" refers to a monovalent or multivalent non-aromatic, saturated or partially unsaturated ring having 3 to 12 carbon atoms as a monocyclic, bicyclic or tricyclic ring system. A carbobicyclyl system includes a spiro carbobicyclyl or a fused carbobicyclyl. Suitable carbocyclyl groups include, but are not limited to, cycloalkyl, cycloalkenyl, and cycloalkynyl. Further non-limiting examples of carbocyclyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, and the like.

The term "cycloalkyl" refers to a monovalent or multivalent saturated ring having 3 to 12 carbon atoms as a monocyclic, bicyclic, or tricyclic ring system. In one embodiment, the cycloalkyl contains 3-12 carbon atoms. In another embodiment, the cycloalkyl contains 3-8 carbon atoms. In still another embodiment, the cycloalkyl contains 3-6 carbon atoms. The cycloalkyl radical may be optionally substituted independently with one or more substituents disclosed herein.

The term "heterocycle", "heterocyclyl", or "heterocyclic ring" as used interchangeably herein refers to a saturated or partially unsaturated monocyclic, bicyclic or tricyclic ring containing 3-12 ring atoms of which at least one ring atom is selected from nitrogen, sulfur and oxygen, and which may, unless otherwise specified, be carbon or nitrogen linked, and of which a —$CH_2$— group can optionally be replaced by a —C(=O)— group. Ring sulfur atoms may be optionally oxidized to form S-oxides. Ring nitrogen atoms maybe optionally oxidized to form N-oxides. In one embodiment, heterocyclyl may be 3-8 membered heterocyclyl, which refers to a saturated or partially unsaturated monocyclic ring containing 3-8 ring atoms. In another embodiment, heterocyclyl may be 3-6 membered heterocyclyl, which refers to a saturated or partially unsaturated monocyclic ring containing 3-6 ring atoms. In still another embodiment, heterocyclyl refers to a 7-12 membered heterocyclyl, which refers to a saturated or partially unsaturated spiro or fused bicyclyl ring containing 7-12 ring atoms.

Examples of heterocyclyl include, but are not limited to, oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, dithianyl, homopiperazinyl, homopiperidinyl, oxepanyl, thiepanyl, oxazepinyl, diazepinyl, thiazepinyl, indolinyl, 1,2,3,4-tetrahydroisoquinolinyl, 1,3-benzodioxolyl, 2-oxa-5-azabicyclo [2.2.1]hept-5-yl. Some non-limited examples of heterocyclyl wherein —$CH_2$— group is replaced by —C(=O)— moiety are 2-oxopyrrolidinyl, oxo-1,3-thiazolidinyl, 2-piperidinonyl, 3,5-dioxopiperidinyl and pyrimidinedionyl. Some non-limited examples of heterocyclyl wherein the ring sulfur atom is oxidized are sulfolanyl, 1,1-dioxo-thiomorpholinyl. The heterocyclyl group may be optionally substituted with one or more substituents disclosed herein.

The terms "fused bicyclic ring", "fused cyclic", "fused bicyclyl" and "fused cyclyl" are used interchangeably and refer to a monovalent or multivalent, saturated or partially unsaturated bridged ring system, which refers to a bicyclic ring system that is not aromatic. Such a system may contain isolated or conjugated unsaturation, but not aromatic or heteroaromatic rings in its core structure (but may have aromatic substitution thereon).

The terms "spirocyclyl", "spirocyclic", "spiro bicyclyl" and "spiro bicyclic" are used interchangeably and refer to a monovalent or multivalent, saturated or partially unsaturated ring system wherein a ring originating from a particular annular carbon of another ring. For example, as depicted below in Figure a, a saturated bridged ring system (ring B and B') is termed as "fused bicyclyl", whereas ring A and ring B share an atom between the two saturated ring system, which terms as a "spirocyclyl" or "spiro bicyclyl". Each ring in the fused bicyclyl or the spiro bicyclyl can be either a carbocyclyl or a heterocyclyl, and each ring is optionally substituted independently with one or more substituents disclosed herein.

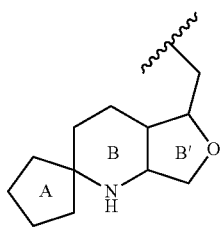

Figure a

The term "heterocycloalkyl" refers to a monovalent or multivalent saturated ring having 3 to 12 ring atoms as a monocyclic, bicyclic, or tricyclic ring system in which at least one ring atom is selected from nitrogen, sulfur and oxygen.

The term "n membered" where n is an integer typically describes the number of ring-forming atoms in a moiety where the number of ring-forming atoms is n. For example, piperidinyl is an example of a 6 membered heterocycloalkyl and 1,2,3,4-tetrahydronaphthyl is an example of a 10 membered cycloalkyl group.

The term "unsaturated" refers to a moiety having one or more units of unsaturation.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" refers to Fluoro (F), Chloro (Cl), Bromo (Br), or Iodo (I).

The term "azido" or "$N_3$" refers to an azide moiety. This radical may be attached, for example, to a methyl group to form azidomethane (methyl azide, $MeN_3$); or attached to a phenyl group to form phenyl azide ($PhN_3$).

The term "aryl" refers to monocyclic, bicyclic, and tricyclic carbocyclic ring systems having a total of 6 to 14 ring members, preferably, 6 to 12 ring members, and more preferably 6 to 10 ring members, wherein at least one ring in the system is aromatic and each ring in the system contains 3 to 7 ring members. An aryl radical is commonly, but not necessarily, attached to the rest of the molecule via an aromatic ring of the aryl radical. The term "aryl" may be used interchangeably with the term "aryl ring" or "aromatic ring". Some non-limiting examples of the aryl group would include phenyl, naphthyl, and anthryl. The aryl radical is optionally substituted independently with one or more substituents described herein.

The term "heteroaryl" or "heteroaromatic ring" refers to monocyclic, bicyclic, and tricyclic ring systems having a total of 5 to 14 ring members, preferably 5 to 10 ring members, and more preferably 5 to 6 ring members, wherein at least one ring in the system is aromatic, at least one ring in the system contains one or more heteroatoms, and each ring in the system contains 5 to 7 ring members. A heteroaryl radical is commonly, but not necessarily, attached to the rest of the molecule via an aromatic ring of the heteroaryl radical. The term "heteroaryl" may be used interchangeably with the term "heteroaryl ring" or the term "heteroaromatic ring". The heteroaryl radicals are optionally substituted independently with one or more substituents described herein. In one embodiment, a 5-10 membered heteroaryl comprises 1, 2, 3 or 4 heteroatoms independently selected from O, S and N. The heteroaryl radical is optionally substituted independently with one or more substituents described herein.

Some non-limiting examples of the heteroaryl group include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl and [1,2,4]triazolo[1,5-a]pyridyl.

The term "carboxy" or "carboxyl", whether used alone or with other terms, such as "carboxyalkyl", refers to —$CO_2H$. The term "carbonyl", whether used alone or with other terms, such as "aminocarbonyl", denotes —(C=O)—.

The term "alkylamino" embraces "N-alkylamino" and "N,N-dialkylamino" where amino groups are independently substituted with one alkyl radical or with two alkyl radicals, respectively. Some non-limiting examples of alkylamino radicals are "lower alkylamino" radicals having one or two alkyl radicals of one to six carbon atoms, attached to a nitrogen atom. Suitable alkylamino radicals may be mono or dialkylamino such as N-methylamino, N-ethylamino, N,N-dimethylamino, N,N-diethylamino and the like. The term "arylamino" refers to amino groups, which have been substituted with one or two aryl radicals, such as N-phenylamino. The arylamino radicals may be further substituted on the aryl ring portion of the radical.

The term "aminoalkyl" refers to linear or branched alkyl radicals having one to about ten carbon atoms any one of which may be substituted with one or more amino radicals. More preferred aminoalkyl radicals are "lower aminoalkyl" radicals having 1-6 carbon atoms and one or more amino radicals. Examples of such radicals include aminomethyl, aminoethyl, aminopropyl, aminobutyl and aminohexyl.

The term "protecting group" or "PG" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethyl silyl)ethoxy-methyl, 2-(p-toluenesulfonyl)-ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The terms "metastasis" or "metastasis disease" refer to a spread of a cancer or disease from one organ or part to another not directly connected with it. The new occurrences of disease thus generated are referred to as metastases. For example, someone with melanoma may have a metastasis in their brain.

Description of Compounds of the Invention

The present invention provides substituted bicyclic pyrazolone compounds which are potentially useful in the treatment of diseases associated with inappropriate kinase activity, in particular inappropriate Axl, Mer (MERTK), c-Met (HGFR) and/or Ron (MST1R) kinase activity.

Specifically, in one aspect, provided herein is a compound having Formula (I):

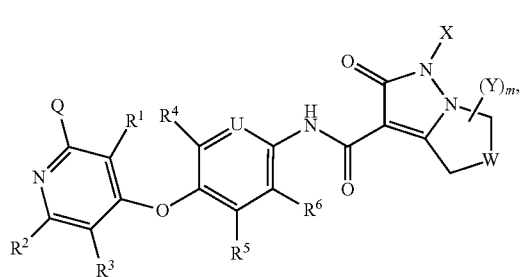

(I)

or a stereoisomer, a tautomer, an N-oxide, a solvate, a metabolite, a pharmaceutically acceptable salt or a prodrug thereof, wherein:

Q is H, OR$^a$, NR$^a$R$^b$, —C(=O)NR$^a$R$^b$, —N(R$^c$)C(=O)R$^d$, —N(R$^c$)C(=O)OR$^a$ or —N(R$^c$)C(=O)NR$^a$R$^b$;

U is CR$^7$ or N, provided that when U is N, the compound is not 2-oxo-1-phenyl-N-(5-((2-(pyrrolidine-1-carboxamido)pyridin-4-yl)oxy)pyridin-2-yl)-2,4,6,7-tetrahydro-1H-pyrazolo[5,1-c][1,4]oxazine-3-carboxamide or 1-(buta-1,3-dien-2-yl)-2-oxo-N-(5-((2-(pyrrolidine-1-carboxamido)pyridin-4-yl)oxy)pyridin-2-yl)-1,2,4,5,6,7-hexahydropyrazolo[1,5-a]pyrazine-3-carboxamide;

X is H, C$_1$-C$_6$ alkyl, C$_3$-C$_8$ alkenyl, C$_3$-C$_8$ alkynyl, C$_3$-C$_8$ cycloalkyl, —(C$_1$-C$_4$ alkylene)-(C$_3$-C$_8$ cycloalkyl), 3-8 membered heterocyclyl, —(C$_1$-C$_4$ alkylene)-(3-8 membered heterocyclyl), C$_6$-C$_{10}$ aryl, —(C$_1$-C$_4$ alkylene)-(C$_6$-C$_{10}$ aryl), 5-10 membered heteroaryl or —(C$_1$-C$_4$ alkylene)-(5-10 membered heteroaryl), wherein each of the C$_1$-C$_6$ alkyl, C$_3$-C$_8$ alkenyl, C$_3$-C$_8$ alkynyl, C$_3$-C$_8$ cycloalkyl, —(C$_1$-C$_4$ alkylene)-(C$_3$-C$_8$ cycloalkyl), 3-8 membered heterocyclyl, —(C$_1$-C$_4$ alkylene)-(3-8 membered heterocyclyl), C$_6$-C$_{10}$ aryl, —(C$_1$-C$_4$ alkylene)-(C$_6$-C$_{10}$ aryl), 5-10 membered heteroaryl and —(C$_1$-C$_4$ alkylene)-(5-10 membered heteroaryl) is optionally substituted with 1, 2, 3, 4 or 5 substituents independently selected from F, Cl, Br, CN, C$_1$-C$_6$ alkyl, C$_2$-C$_6$ alkenyl, C$_2$-C$_6$ alkynyl, OR$^a$, NR$^a$R$^b$, —(C$_1$-C$_4$ alkylene)-OR$^a$ and —(C$_1$-C$_4$ alkylene)-NR$^a$R$^b$;

each Y is independently C$_1$-C$_6$ alkyl, C$_2$-C$_6$ alkenyl, C$_2$-C$_6$ alkynyl, C$_3$-C$_8$ cycloalkyl, —(C$_1$-C$_4$ alkylene)-(C$_3$-C$_8$ cycloalkyl), 3-8 membered heterocyclyl, —(C$_1$-C$_4$ alkylene)-(3-8 membered heterocyclyl), C$_6$-C$_{10}$ aryl, —(C$_1$-C$_4$ alkylene)-(C$_6$-C$_{10}$ aryl), 5-10 membered heteroaryl, —(C$_1$-C$_4$ alkylene)-(5-10 membered heteroaryl), OR$^a$, NR$^a$R$^b$, —(C$_1$-C$_4$ alkylene)-OR$^a$ or —(C$_1$-C$_4$ alkylene)-NR$^a$R$^b$;

m is 0, 1, 2, 3, 4;

W is —(CH$_2$)$_n$—, —(CH$_2$)$_n$O—, —(CH$_2$)—NH— or —(CH$_2$)—S—, wherein n is 0, 1, 2, 3 or 4;

each of R$^1$, R$^2$, R$^3$, R$^4$, R$^5$, R$^6$ and R$^7$ is independently H, F, Cl, Br, CN, N$_3$, OR$^a$, C$_1$-C$_6$ alkyl, C$_1$-C$_6$ haloalkyl, C$_2$-C$_6$ alkenyl or C$_2$-C$_6$ alkynyl;

each of R$^a$, R$^b$ and R$^c$ is independently H, C$_1$-C$_6$ alkyl, C$_1$-C$_6$ haloalkyl, C$_3$-C$_6$ cycloalkyl, —(C$_1$-C$_4$ alkylene)-(C$_3$-C$_6$ cycloalkyl), 3-6 membered heterocyclyl, —(C$_1$-C$_4$ alkylene)-(3-6 membered heterocyclyl), C$_6$-C$_{10}$ aryl, —(C$_1$-C$_4$ alkylene)-(C$_6$-C$_{10}$ aryl), 5-10 membered heteroaryl or —(C$_1$-C$_4$ alkylene)-(5-10 membered heteroaryl), or R$^a$ and R$^b$ taken together with the nitrogen atom to which they are attached form a 3-8 membered heterocyclic ring, wherein each of the C$_1$-C$_6$ alkyl, C$_1$-C$_6$ haloalkyl, C$_3$-C$_6$ cycloalkyl, —(C$_1$-C$_4$ alkylene)-(C$_3$-C$_6$ cycloalkyl), 3-6 membered heterocyclyl, —(C$_1$-C$_4$ alkylene)-(3-6 membered heterocyclyl), C$_6$-C$_{10}$ aryl, —(C$_1$-C$_4$ alkylene)-(C$_6$-C$_{10}$ aryl), 5-10 membered heteroaryl, —(C$_1$-C$_4$ alkylene)-(5-10 membered heteroaryl) and 3-8 membered heterocyclic ring is optionally substituted with 1, 2, 3 or 4 substituents independently selected from F, Cl, CN, N$_3$, OH, NH$_2$, C$_1$-C$_6$ haloalkyl, C$_1$-C$_6$ alkoxy and C$_1$-C$_6$ alkylamino; and R$^d$ is H, C$_1$-C$_6$ alkyl, C$_3$-C$_8$ cycloalkyl, —(C$_1$-C$_4$ alkylene)-(C$_3$-C$_8$ cycloalkyl), 3-8 membered heterocyclyl, —(C$_1$-C$_4$ alkylene)-(3-8 membered heterocyclyl), C$_6$-C$_{10}$ aryl, —(C$_1$-C$_4$ alkylene)-(C$_6$-C$_{10}$ aryl), 5-10 membered heteroaryl or —(C$_1$-C$_4$ alkylene)-(5-10 membered heteroaryl), wherein each of the C$_1$-C$_6$ alkyl, C$_3$-C$_8$ cycloalkyl, —(C$_1$-C$_4$ alkylene)-(C$_3$-C$_8$ cycloalkyl), 3-8 membered heterocyclyl, —(C₁-C₄ alkylene)-(3-8 membered heterocyclyl), C₆-C₁₀ aryl, —(C₁-C₄ alkylene)-(C₆-C₁₀ aryl), 5-10 membered heteroaryl and —(C₁-C₄ alkylene)-(5-10 membered heteroaryl) is optionally substituted with 1, 2, 3 or 4 substituents independently selected from F, Cl, Br, CN, OR$^a$, NR$^a$R$^b$, C₁-C₆ alkyl, C₂-C₆ alkenyl, C₂-C₆ alkynyl, —(C₁-C₄ alkylene)-OR$^a$ and —(C₁-C₄ alkylene)-NR$^a$R$^b$.

In one embodiment, Q is NR$^a$R$^b$, —C(=O)NR$^a$R$^b$, —N(R$^c$)C(=O)R$^d$ or —N(R$^c$)C(=O)NR$^a$R$^b$.

In another embodiment, X is C₁-C₄ alkyl, C₃-C₆ alkenyl, C₃-C₆ alkynyl, C₃-C₆ cycloalkyl, —(C₁-C₂ alkylene)-(C₃-C₆ cycloalkyl), phenyl or —(C₁-C₂ alkylene)-phenyl, wherein each of the C₁-C₄ alkyl, C₃-C₆ alkenyl, C₃-C₆ alkynyl, C₃-C₆ cycloalkyl, —(C₁-C₂ alkylene)-(C₃-C₆ cycloalkyl), phenyl and —(C₁-C₂ alkylene)-phenyl is optionally substituted with 1, 2, 3, 4 or 5 substituents independently selected from F, Cl, Br, CN, C₁-C₄ alkyl, C₂-C₄ alkenyl, C₂-C₄ alkynyl, OR$^a$, NR$^a$R$^b$, —(C₁-C₂ alkylene)-OR$^a$ and —(C₁-C₂ alkylene)-NR$^a$R$^b$.

In another embodiment, each Y is independently C₁-C₆ alkyl, C₂-C₆ alkenyl, C₂-C₆ alkynyl, C₃-C₆ cycloalkyl, —(C₁-C₂ alkylene)-(C₃-C₆ cycloalkyl), 3-6 membered heterocyclyl, —(C₁-C₂ alkylene)-(3-6 membered heterocyclyl), phenyl, —(C₁-C₂ alkylene)-phenyl, 5-6 membered heteroaryl, —(C₁-C₂ alkylene)-(5-6 membered heteroaryl), OR$^a$, NR$^a$R$^b$, —(C₁-C₂ alkylene)-OR$^a$ or —(C₁-C₂ alkylene)-NR$^a$R$^b$; m is 0, 1 or 2.

In another embodiment, W is —(CH₂)$_n$—, —(CH₂)$_n$O— or —(CH₂)—NH—, wherein n is 0, 1 or 2.

In another embodiment, each of R¹, R², R³, R⁴, R⁵, R⁶ and R⁷ is independently H, F, Cl, Me or OMe.

In another embodiment, each of R$^a$, R$^b$ and R$^c$ is independently H, C₁-C₄ alkyl, C₁-C₄ haloalkyl, C₃-C₆ cycloalkyl, —(C₁-C₂ alkylene)-(C₃-C₆ cycloalkyl), 3-6 membered heterocyclyl or —(C₁-C₂ alkylene)-(3-6 membered heterocyclyl), or R$^a$ and R$^b$ taken together with the nitrogen atom to which they are attached form a 3-8 membered heterocyclic ring, wherein each of the C₁-C₄ alkyl, C₁-C₄ haloalkyl, C₃-C₆ cycloalkyl, —(C₁-C₂ alkylene)-(C₃-C₆ cycloalkyl), 3-6 membered heterocyclyl, —(C₁-C₂ alkylene)-(3-6 membered heterocyclyl) and 3-8 membered heterocyclic ring is optionally substituted with 1, 2, 3 or 4 substituents independently selected from F, Cl, CN, N₃, OH, NH₂, C₁-C₃ haloalkyl, C₁-C₃ alkoxy and C₁-C₃ alkylamino.

In one embodiment, R$^d$ is H, C₁-C₄ alkyl, C₃-C₆ cycloalkyl, —(C₁-C₂ alkylene)-(C₃-C₆ cycloalkyl), 3-6 membered heterocyclyl or —(C₁-C₂ alkylene)-(3-6 membered heterocyclyl), wherein each of the C₁-C₄ alkyl, C₃-C₆ cycloalkyl, —(C₁-C₂ alkylene)-(C₃-C₆ cycloalkyl), 3-6 membered heterocyclyl and —(C₁-C₂ alkylene)-(3-6 membered heterocyclyl) is optionally substituted with 1, 2, 3 or 4 substituents independently selected from F, CN, C₁-C₄ alkyl, C₂-C₄ alkenyl, C₂-C₄ alkynyl, —(C₁-C₂ alkylene)-OR$^a$ and —(C₁-C₂ alkylene)-NR$^a$R$^b$.

In another embodiment, Q is:

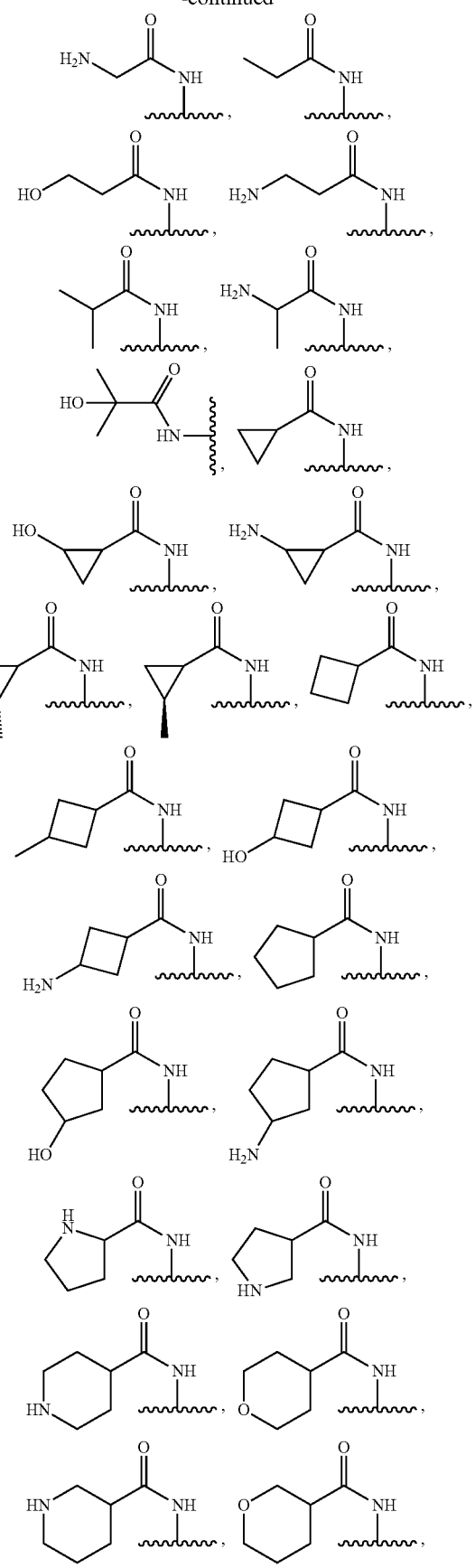

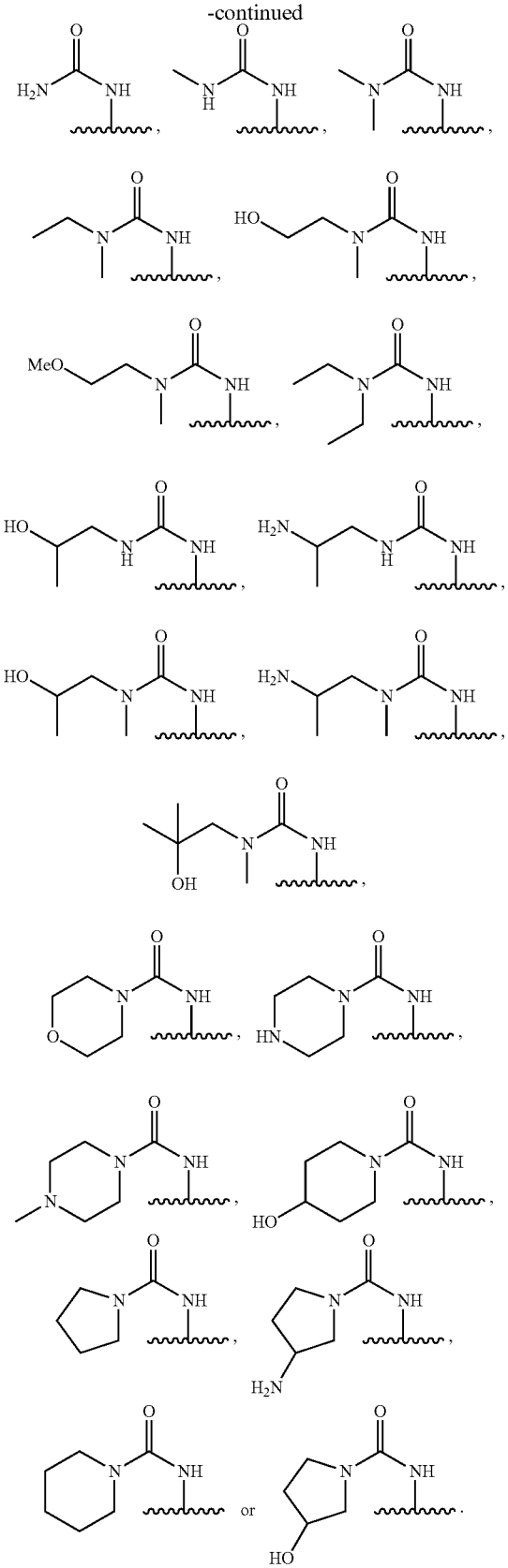
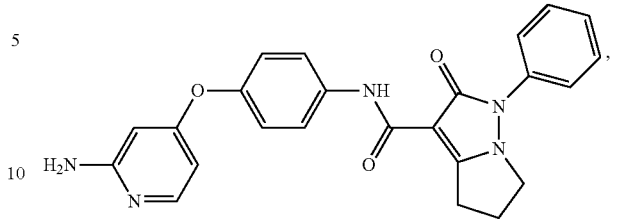
(1)
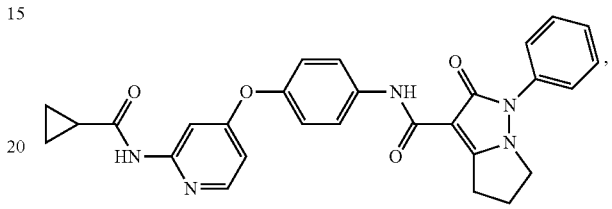
(2)
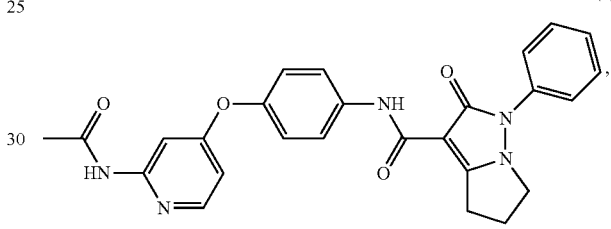
(3)
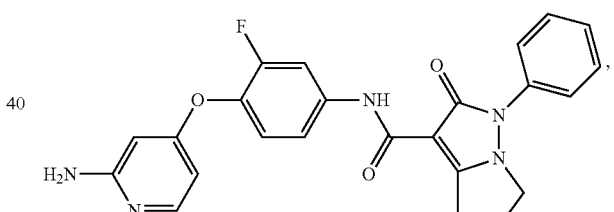
(4)
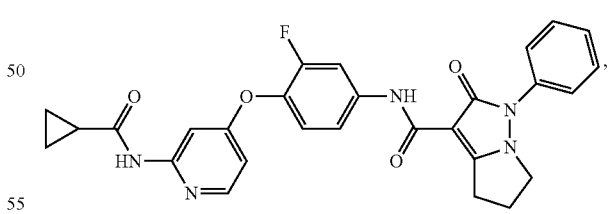
(5)
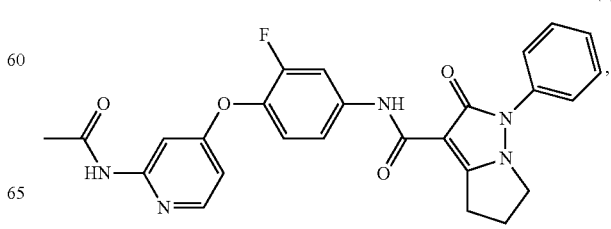
(6)
In another embodiment, the compound disclosed herein having one of the following structure:

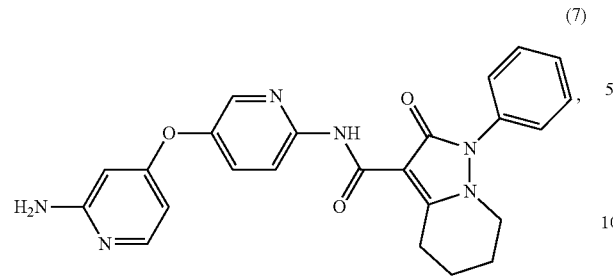
(7)
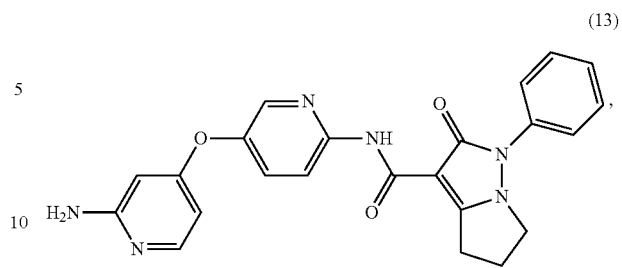
(13)
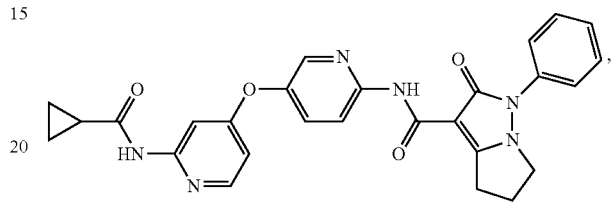
(8), (14)
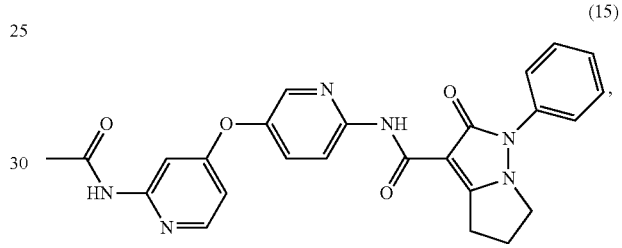
(9), (15)
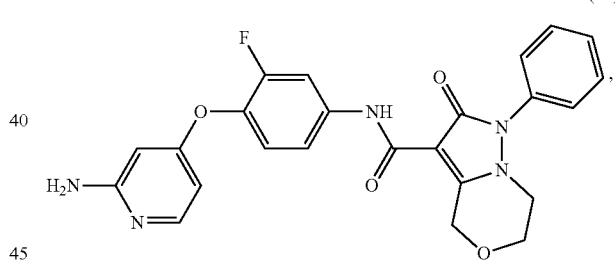
(10), (16)
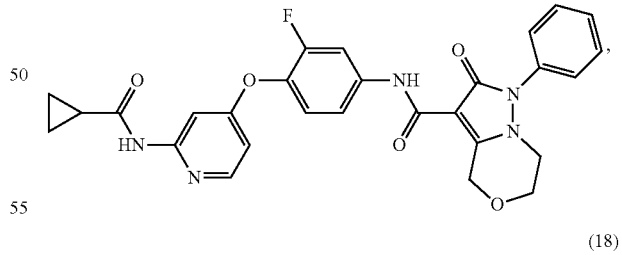
(11), (17)
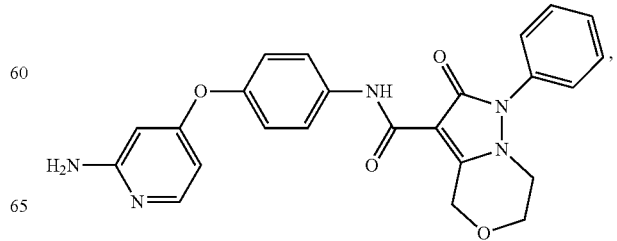
(12), (18)

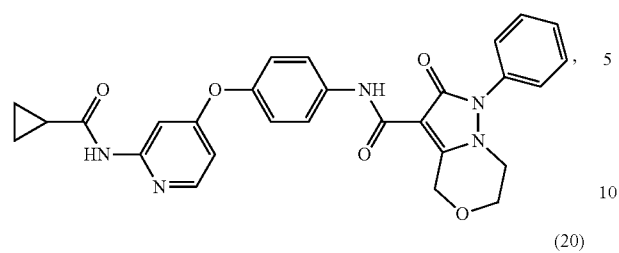
(19)
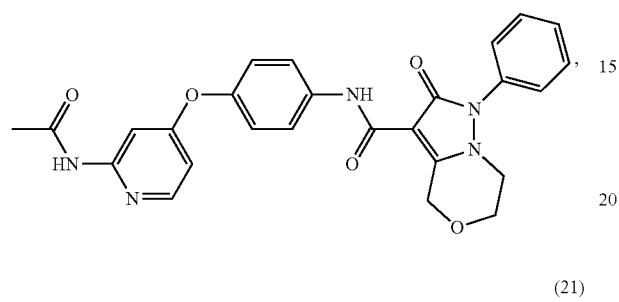
(20)
(21)
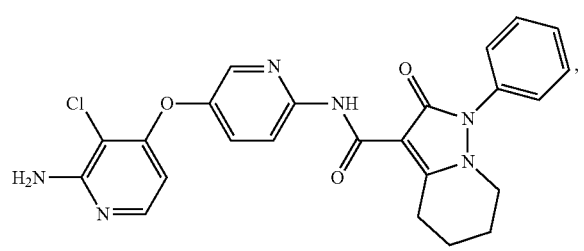
(22)
(23)
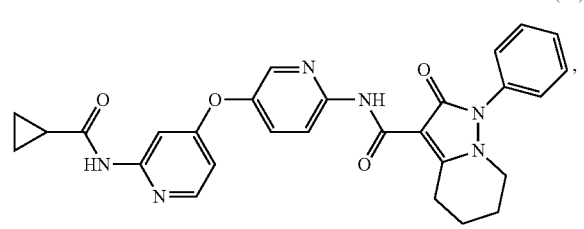
(24)
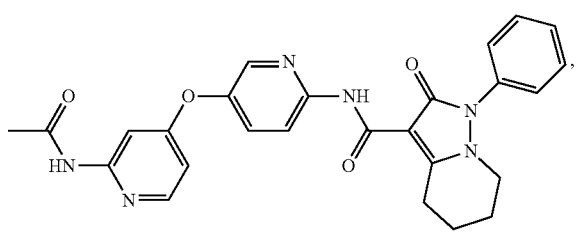
(25)
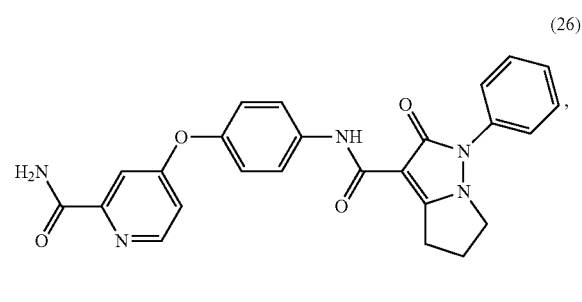
(26)
(27)
(28)
(29)
(30)

Unless otherwise stated, all stereoisomers, tautomers, solvates, metabolites, salts, and pharmaceutically acceptable prodrugs of the compounds of Formula (I) are within the scope of the invention.

The compounds disclosed herein may contain asymmetric or chiral centers, and therefore exist in different stereoisomeric forms. It is intended that all stereoisomeric forms of compounds of Formula (I), including but not limited to, diastereomers, enantiomers, atropisomers, conformers (rotamers) and geometric (cis/trans) isomers as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of Formula (I) may exist in different tautomeric forms, and all such forms are embraced within the scope of the invention, as defined by the claims.

The compounds of Formula (I) can be in the form of salts. In one embodiment, the salts are pharmaceutically acceptable salts. The phrase "pharmaceutically acceptable" indicates that the substance or composition must be compatible chemically and/or toxicologically, with the other ingredients comprising a formulation, and/or the mammal being treated therewith. In another embodiment, the salts are not necessarily pharmaceutically acceptable salts, and which may be useful as intermediates for preparing and/or purifying compounds of Formula (I) and/or for separating enantiomers of compounds of Formula (I).

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, lauryl sulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H (deuterium, D), $^3$H, $^{11}$C, $^{13}$C, $^{14}$C, $^{15}$N, $^{17}$O, $^{18}$O, $^{18}$F, $^{31}$P, $^{32}$P, $^{35}$S, $^{36}$Cl, $^{125}$I, respectively.

In another aspect, the compounds of the invention include isotopically enriched compounds as defined herein, for example those into which radioactive isotopes, such as $^3$H, $^{14}$C and $^{18}$F, or those into which non-radioactive isotopes, such as $^2$H and $^{13}$C are present. Such isotopically enriched compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, acetone-$d_6$, DMSO-$d_6$.

In another aspect, provided herein are intermediates for preparing the compounds disclosed herein.

In another aspect, provided herein are methods of preparing, methods of separating, and methods of purifying the compounds disclosed herein.

Pharmaceutical Composition, Formulations and Administration of the Compounds of the Invention The present invention provides a pharmaceutical composition that include a compound of disclosed herein, or a compound listed in Table 1; and a pharmaceutically acceptable excipient, carrier, adjuvant, vehicle or a combination thereof. The amount of compound in the pharmaceutical composition disclosed herein is such that is effective to detectably inhibit a protein kinase in a biological sample or in a patient.

It will also be appreciated that certain compounds disclosed herein can exist in free form for treatment, or where appropriate, as a pharmaceutically acceptable derivative thereof. Some non-limiting examples of pharmaceutically acceptable derivative include pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

The pharmaceutical compositions disclosed herein may be prepared and packaged in bulk form wherein a safe and effective amount of the compound disclosed herein can be extracted and then given to the patient such as with powders or syrups. Alternatively, the pharmaceutical compositions disclosed herein may be prepared and packaged in unit dosage form wherein each physically discrete unit contains the compound disclosed herein. When prepared in unit dosage form, the pharmaceutical compositions of the invention typically may contain, for example, from 0.5 mg to 1 g, or from 1 mg to 700 mg, or from 5 mg to 100 mg of the compound disclosed herein.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound disclosed herein when administered to a patient and interactions which would result in pharmaceutical compositions that are not pharmaceutically acceptable are avoided. In addition, each excipient must be pharmaceutically-acceptable, e.g., of sufficiently high purity.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds disclosed herein once administered to the patient from one organ, or portion of the body, to another organ, or portion of the body. Certain pharmaceutically acceptable excipients may be chosen for their ability to enhance patient compliance.

Suitable pharmaceutically acceptable excipients comprise the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

The pharmaceutical compositions disclosed herein are prepared using techniques and methods known to those skilled in the art. Some of the methods commonly used in the art are described in Remington's Pharmaceutical Sciences (Mack Publishing Company).

Accordingly, in another aspect the invention is directed to process for the preparation of a pharmaceutical composition comprising the compound disclosed herein and a pharmaceutically acceptable excipient, carrier, adjuvant, vehicle or a combination thereof, which comprises mixing the ingredients. A pharmaceutical composition comprising the compound disclosed herein may be prepared by, for example, admixture at ambient temperature and atmospheric pressure.

The compounds disclosed herein will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

In one embodiment, the compounds disclosed herein will be formulated for oral administration. In another embodiment, the compounds disclosed herein will be formulated for inhaled administration. In a further embodiment, the compounds disclosed herein will be formulated for intranasal administration. In another embodiment, the compounds disclosed herein will be formulated for transdermal administration. In a further embodiment, the compounds disclosed herein will be formulated for topical administration.

The pharmaceutical compositions provided herein can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable nonaqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

Where appropriate, dosage unit formulations for oral administration can be microencapsulated. The composition can also be prepared to prolong or sustain the release as for example by coating or embedding particulate material in polymers, wax or the like.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The compounds disclosed herein may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds disclosed herein may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The pharmaceutical compositions provided herein can be formulated as immediate or modified release dosage forms, including delayed-, sustained-, pulsed-, controlled-, targeted-, and programmed-release forms.

The pharmaceutical compositions provided herein can be co-formulated with other active ingredients which do not impair the desired therapeutic action, or with substances that supplement the desired action.

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein can be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein can be formulated as immediate or modified release dosage forms, including delayed-, sustained-, pulsed-, controlled-, targeted-, and programmed-release forms.

The pharmaceutical compositions can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In another aspect, The pharmaceutical compositions disclosed herein can be formulated in any dosage forms that are adapted for administration to a patient by inhalation, for example as a dry powder, an aerosol, a suspension, or a solution composition. In one embodiment, the pharmaceutical compositions disclosed herein can be formulated in a dosage form adapted for administration to a patient by inhalation as a dry powder. In a further embodiment, the pharmaceutical compositions disclosed herein can be formulated in a dosage form adapted for administration to a patient by inhalation via a nebulizer. Dry powder compositions for delivery to the lung by inhalation typically comprise the compounds disclosed herein as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

Aerosols may be formed by suspending or dissolving the compound disclosed herein in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising the compound disclosed herein will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilizing agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound disclosed herein may be employed with either a paraffinic or a water-miscible ointment base. Alternatively, the compound disclosed herein may be formulated in a cream with an oil-in-water cream base or a water-in-oil base.

Use of the Compounds and Compositions of the Invention

The present invention provides a method of using the compound disclosed herein, or the pharmaceutical composition comprising the compound disclosed herein for the treatment, prevention, or amelioration of a disease that are mediated or otherwise affected via receptor tyrosine kinase, especially Axl, Mer, c-Met and/or Ron kinase activity.

In one embodiment, provided herein is a method of using the compound or the pharmaceutical composition disclosed herein for the treatment, prevention or amelioration of a disease that is mediated or otherwise affected via inappropriate Axl kinase activity. In another embodiment, a disease is related to the inappropriate activity of Mer kinase. In still another embodiment, a disease is related to the inappropriate activity of c-Met kinase. In yet another embodiment, a disease is related to the inappropriate activity of Ron kinase.

The compound disclosed herein would be useful for, but not limited to, the prevention or treatment of proliferative diseases, condition, or disorder in a patient by administering to the patient a compound or a composition disclosed herein in an effective amount. Such diseases, conditions, or disorders include cancer, particularly metastatic cancer, atherosclerosis, and lung fibrosis.

The compounds disclosed herein would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xeroderma pigmentosum, keratoacanthoma, thyroid follicular cancer and Kaposi's sarcoma).

The compounds disclosed herein also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

The compounds are also useful for the treatment of edema, and conditions of vascular hyperpermeability.

The compounds disclosed herein are also useful in the treatment of diabetic conditions such as diabetic retinopathy and microangiopathy. The compounds disclosed herein are also useful in the reduction of blood flow in a tumor in a subject. The compounds disclosed herein are also useful in the reduction of metastasis of a tumor in a subject.

Besides being useful for human treatment, the compounds disclosed herein are also useful for veterinary treatment of companion animals, exotic animals and farm animals, including mammals, rodents, and the like. More preferred animals include horses, dogs, and cats. As used herein, the compounds disclosed herein include the pharmaceutically acceptable derivatives thereof.

Combination Therapy

A compound disclosed herein can be administered as the sole active agent or it can be administered in combination with other therapeutic agents, including other compounds that demonstrate the same or a similar therapeutic activity and that are determined to be safe and efficacious for such combined administration.

In one aspect, provided herein is a method of treating, preventing, or ameliorating a disease or disorder comprising administering a safe and effective amount of a combination comprising the compound disclosed herein together with one or more other therapeutically active agents. In one embodiment, the combinations comprising one or two other therapeutic agents.

In another aspect, provided herein is a product comprising a compound disclosed herein and at least one other therapeutic agent as a combined preparation for simultaneous, separate or sequential use in therapy. In one embodiment, the therapy is the treatment of a disease or disorder mediated by the activity of the Axl, Mer, c-Met and/or Ron kinase. Products provided as a combined preparation include a composition comprising the compound disclosed herein and the other therapeutic agent(s) together in the same pharmaceutical composition, or the compound disclosed herein and the other therapeutic agent(s) in separate form, e.g. in the form of a kit.

In another aspect, provided herein is a pharmaceutical composition comprising a compound disclosed herein and another therapeutic agent(s). In one embodiment, the pharmaceutical composition may comprise a pharmaceutically acceptable excipient, carrier, adjuvant or vehicle as described above.

In another aspect, provided herein is a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

The invention also provides the use of a compound disclosed herein for treating a disease or condition mediated by the activity of the Axl, Mer, c-Met and/or Ron kinase, wherein the patient has previously (e.g. within 24 hours) been treated with another therapeutic agent. The invention also provides the use of another therapeutic agent for treating a disease or condition mediated by the activity of the Axl, Mer, c-Met and/or Ron kinase, wherein the patient has previously (e.g. within 24 hours) been treated with a compound disclosed herein.

The therapeutic agents which can be used in combination with the compound disclosed herein include, but not limited to, chemotherapeutic agents or other anti-proliferative agents, agents for treating atherosclerosis, agents for treating lung fibrosis. Where the compound disclosed herein is administered in conjunction with other therapeutic agent will of course vary depending on the type of co-drug employed, on the specific drug employed, on the condition being treated and so forth.

The chemotherapeutic agents or other anti-proliferative agents may refer to aromatase inhibitors; antiestrogens; topoisomerase I inhibitors; topoisomerase II inhibitors; microtubule active agents; alkylating agents; histone deacetylase inhibitors; compounds that induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; antiandrogens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, nonsteroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g., under the trademark AROMASIN®. Formestane can be administered, e.g., in the form as it is marketed, e.g., under the trademark LENTARON®. Fadrozole can be administered, e.g., in the form as it is marketed, e.g., under the trademark AFEMA®. Anastrozole can be administered, e.g., in the form as it is marketed, e.g., under the trademark ARIMIDEX®. Letrozole can be administered, e.g., in the form as it is marketed, e.g., under the trademark FEMARA® or FEMAR®. Aminoglutethimide can be administered, e.g., in the form as it is marketed, e.g., under the trademark ORIMETEN®. A combination of the invention comprising a chemotherapeutic agent which is an aromatase inhibitor is particularly useful for the treatment of hormone receptor positive tumors, e.g., breast tumors.

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, nonsteroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g., under the trademark AROMASIN®. Formestane can be administered, e.g., in the form as it is marketed, e.g., under the trademark LENTARON®. Fadrozole can be administered, e.g., in the form as it is marketed, e.g., under the trademark AFEMA®. Anastrozole can be administered, e.g., in the form as it is marketed, e.g., under the trademark ARIMIDEX®. Letrozole can be administered, e.g., in the form as it is marketed, e.g., under the trademark FEMARA® or FEMAR®. Aminoglutethimide can be administered, e.g., in the form as it is marketed, e.g., under the trademark ORIMETEN®. A combination of the invention comprising a chemotherapeutic agent which is an aromatase inhibitor is particularly useful for the treatment of hormone receptor positive tumors, e.g., breast tumors.

The term "anti-estrogen", as used herein, relates to a compound which antagonizes the effect of estrogens at the estrogen receptor level. The term includes, but is not limited to, tamoxifen, fulvestrant, raloxifene and raloxifene hydrochloride. Tamoxifen can be administered, e.g., in the form as it is marketed, e.g., under the trademark NOLVADEX®. Raloxifene hydrochloride can be administered, e.g., in the form as it is marketed, e.g., under the trademark EVISTA®. Fulvestrant can be formulated as disclosed in U.S. Pat. No. 4,659,516 or it can be administered, e.g., in the form as it is marketed, e.g., under the trademark FASLODEX®. A combination of the invention comprising a chemotherapeutic agent which is an antiestrogen is particularly useful for the treatment of estrogen receptor positive tumors, e.g., breast tumors.

The term "anti-androgen", as used herein, relates to any substance which is capable of inhibiting the biological effects of androgenic hormones and includes, but is not limited to, bicalutamide (CASODEX®), which can be formulated, e.g., as disclosed in U.S. Pat. No. 4,636,505.

The term "gonadorelin agonist", as used herein, includes, but is not limited to, abarelix, goserelin and goserelin acetate. Goserelin is disclosed in U.S. Pat. No. 4,100,274 and can be administered, e.g., in the form as it is marketed, e.g., under the trademark ZOLADEX®. Abarelix can be formulated, e.g., as disclosed in U.S. Pat. No. 5,843,901.

The term "topoisomerase I inhibitor", as used herein, includes, but is not limited to, topotecan, gimatecan, irinotecan, camptothecian and its analogues, 9-nitrocamptothecin and the macromolecular camptothecin conjugate PNU-166148 (compound A1 in WO 99/17804). Irinotecan can be administered, e.g., in the form as it is marketed, e.g., under the trademark CAMPTOSAR®. Topotecan can be administered, e.g., in the form as it is marketed, e.g., under the trademark HYCAMTIN®.

The term "topoisomerase II inhibitor", as used herein, includes, but is not limited to, the anthracyclines, such as doxorubicin, including liposomal formulation, e.g., CAELYX®; daunorubicin; epirubicin; idarubicin; nemorubicin; the anthraquinones mitoxantrone and losoxantrone; and the podophillotoxines etoposide and teniposide. Etoposide can be administered, e.g., in the form as it is marketed, e.g., under the trademark ETOPOPHOS®. Teniposide can be administered, e.g., in the form as it is marketed, e.g., under the trademark VM 26-BRISTOL®. Doxorubicin can be administered, e.g., in the form as it is marketed, e.g., under the trademark ADRIBLASTIN® or ADRIAMYCIN®.

Epirubicin can be administered, e.g., in the form as it is marketed, e.g., under the trademark FARIVIORUBICIN®. Idarubicin can be administered, e.g., in the form as it is marketed, e.g., under the trademark ZAVEDOS®. Mitoxantrone can be administered, e.g., in the form as it is marketed, e.g., under the trademark NOVANTRON®.

The term "microtubule active agent" relates to microtubule stabilizing, microtubule destabilizing agents and microtublin polymerization inhibitors including, but not limited to, taxanes, e.g., paclitaxel and docetaxel; vinca alkaloids, e.g., vinblastine, especially vinblastine sulfate; vincristine, especially vincristine sulfate and vinorelbine; discodermolides; cochicine; and epothilones and derivatives thereof, e.g., epothilone B or D or derivatives thereof. Paclitaxel may be administered, e.g., in the form as it is marketed, e.g., TAXOL®. Docetaxel can be administered, e.g., in the form as it is marketed, e.g., under the trademark TAXOTERE®. Vinblastine sulfate can be administered, e.g., in the form as it is marketed, e.g., under the trademark VINBLASTIN R.P®. Vincristine sulfate can be administered, e.g., in the form as it is marketed, e.g., under the trademark FARMISTIN®. Discodermolide can be obtained, e.g., as disclosed in U.S. Pat. No. 5,010,099. Also included are epothilone derivatives which are disclosed in WO 98/10121, U.S. Pat. No. 6,194,181, WO 98/25929, WO 98/08849, WO 99/43653, WO 98/22461 and WO 00/31247. Especially preferred are epothilone A and/or B.

The term "alkylating agent", as used herein, includes, but is not limited to, cyclophosphamide, ifosfamide, melphalan or nitrosourea (BCNU or Gliadel). Cyclophosphamide can be administered, e.g., in the form as it is marketed, e.g., under the trademark CYCLOSTIN®. Ifosfamide can be administered, e.g., in the form as it is marketed, e.g., under the trademark HOLOXAN®.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes suberoylanilide hydroxamic acid (SAHA).

The term "antineoplastic antimetabolite" includes, but is not limited to, 5-fluorouracil or 5-FU; capecitabine; gemcitabine; DNA demethylating agents, such as 5-azacytidine and decitabine; methotrexate and edatrexate; and folic acid antagonists, such as pemetrexed. Capecitabine can be administered, e.g., in the form as it is marketed, e.g., under the trademark XELODA®. Gemcitabine can be administered, e.g., in the form as it is marketed, e.g., under the trademark GEMZAR®. Also included is the monoclonal antibody trastuzumab which can be administered, e.g., in the form as it is marketed, e.g., under the trademark HERCEPTIN®.

The term "platin compound", as used herein, includes, but is not limited to, carboplatin, cis-platin, cisplatinum and oxaliplatin. Carboplatin can be administered, e.g., in the form as it is marketed, e.g., under the trademark CARBOPLAT®. Oxaliplatin can be administered, e.g., in the form as it is marketed, e.g., under the trademark ELOXATIN®.

The term "compounds targeting/decreasing a protein or lipid kinase activity; or a protein or lipid phosphatase activity; or further anti-angiogenic compounds", as used herein, includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GFB-111;
b) compounds targeting, decreasing or inhibiting the activity of the fibroblast growth factor-receptors (FGFR);
c) compounds targeting, decreasing or inhibiting the activity of the insulin-like growth factor receptor I (IGF-IR), such as compounds which target, decrease or inhibit the activity of especially compounds which inhibit the IGF-IR receptor, such as those compounds disclosed in WO 02/092599;

d) compounds targeting, decreasing or inhibiting the activity of the Trk receptor tyrosine kinase family;
e) compounds targeting, decreasing or inhibiting the activity of the Axl receptor tyrosine kinase family;
f) compounds targeting, decreasing or inhibiting the activity of the c-Met receptor;
g) compounds targeting, decreasing or inhibiting the activity of the Kit/SCFR receptor tyrosine kinase;
h) compounds targeting, decreasing or inhibiting the activity of the c-kit receptor tyrosine kinases—(part of the PDGFR family), such as compounds which target, decrease or inhibit the activity of the c-Kit receptor tyrosine kinase family, especially compounds which inhibit the c-Kit receptor, e.g., imatinib;
i) compounds targeting, decreasing or inhibiting the activity of members of the c-Abl family and their gene-fusion products, e.g., BCR-Abl kinase, such as compounds which target decrease or inhibit the activity of c-Abl family members and their gene fusion products, e.g., a N-phenyl-2-pyrimidine-amine derivative, e.g., imatinib, PD180970, AG957, NSC 680410 or PD173955 from ParkeDavis;
j) compounds targeting, decreasing or inhibiting the activity of members of the protein kinase C (PKC) and Raf family of serine/threonine kinases, members of the MEK, SRC, JAK, FAK, PDK and RastMAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; limofosine; RO 31822 and RO 320432; GO 6976; Isis 3521; LY333531/LY379196; isochinoline compounds, such as those disclosed in WO 00/09495; FTIs; PD184352; or QAN697 (a PI3K inhibitor);
k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC®) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555 AG 494, Tyrphostin AG 556, AG957 and adaphostin (4-{[(2,5-dihydroxyphenyl) methyl]amino}-benzoic acid adamantyl ester, NSC 680410, adaphostin; and
l) compounds targeting, decreasing or inhibiting the activity of the epidermal growth factor family of receptor tyrosine kinases (EGFR, ErbB2, ErbB3, ErbB4 as homo- or hetero-dimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF related ligands, and are in particular those compounds, proteins or monoclonal antibodies generically and specifically disclosed in WO 97/02266, e.g., the compound of Example 39, or in EP 0564409; WO 99/03854; EP 0520722; EP 0566226; EP 0787722; EP 0837063; U.S. Pat. No. 5,747,498; WO 98/10767; WO 97/30034; WO 97/49688; WO 97/38983 and, especially, WO 96/30347, e.g., compound known as CP 358774; WO 96/33980, e.g., compound ZD 1839; and WO 95/03283, e.g., compound ZM105180, e.g., trastuzumab (HERCEPTIN), cetuximab, Nessa, Tarceva, OSI-774, CI-1033, EKB-569, GW-2016, E1.1, E2.4, E2.5, E6.2, E6.4, E2.11, E6.3 or E7.6.3; and 7H-pyrrolo-[2,3-d]pyrimidine derivatives which are disclosed in WO 03/013541.

Further anti-angiogenic compounds include compounds having another mechanism for their activity, e.g., unrelated to protein or lipid kinase inhibition, e.g., thalidomide (THALOMID®) and TNP-470.

Compounds which target, decrease or inhibit the activity of a protein or lipid phosphatase are, e.g., inhibitors of phosphatase 1, phosphatase 2A, PTEN or CDC25, e.g., okadaic acid or a derivative thereof.

Compounds that induce cell differentiation processes are e.g. retinoic acid, α-, γ- or δ-tocopherol or α-, γ- or δ-tocotrienol.

The term cyclooxygenase inhibitor, as used herein, includes, but is not limited to, e.g., Cox-2 inhibitors, 5-alkyl substituted 2-arylaminophenylacetic acid and derivatives, such as celecoxib (CELEBREX®), rofecoxib (VIOXX®), etoricoxib, valdecoxib or a 5-alkyl-2-aryl aminophenylacetic acid, e.g., 5-methyl-2-(2'-chloro-6'-fluoroanilino) phenyl acetic acid or lumiracoxib.

The term "bisphosphonates", as used herein, includes, but is not limited to, etridonic, clodronic, tiludronic, pamidronic, alendronic, ibandronic, risedronic and zoledronic acid. "Etridonic acid" can be administered, e.g., in the form as it is marketed, e.g., under the trademark DIDRONEL®. "Clodronic acid" can be administered, e.g., in the form as it is marketed, e.g., under the trademark BONEFOS®. "Tiludronic acid" can be administered, e.g., in the form as it is marketed, e.g., under the trademark SKELID®. "Pamidronic acid" can be administered, e.g., in the form as it is marketed, e.g., under the trademark AREDIA™. "Alendronic acid" can be administered, e.g., in the form as it is marketed, e.g., under the trademark FOSAMAX®. "Ibandronic acid" can be administered, e.g., in the form as it is marketed, e.g., under the trademark BONIDRANAT®. "Risedronic acid" can be administered, e.g., in the form as it is marketed, e.g., under the trademark ACTONEL®. "Zoledronic acid" can be administered, e.g., in the form as it is marketed, e.g., under the trademark ZOMETA®.

The term "mTOR inhibitors" relates to compounds which inhibit the mammalian target of rapamycin (mTOR) and which possess antiproliferative activity, such as sirolimus (Rapamune®), everolimus (Certican™), CCI-779 and ABT578.

The term "heparanase inhibitor", as used herein, refers to compounds which target, decrease or inhibit heparin sulphate degradation. The term includes, but is not limited to, PI-88.

The term "biological response modifier", as used herein, refers to a lymphokine or interferons, e.g., interferon γ.

The term "inhibitor of Ras oncogenic isoforms", e.g., H-Ras, K-Ras or N-Ras, as used herein, refers to compounds which target, decrease or inhibit the oncogenic activity of Ras, e.g., a "farnesyl transferase inhibitor", e.g., L-744832, DK8G557 or R1 15777 (Zarnestra).

The term "telomerase inhibitor", as used herein, refers to compounds which target, decrease or inhibit the activity of telomerase. Compounds which target, decrease or inhibit the activity of telomerase are especially compounds which inhibit the telomerase receptor, e.g., telomestatin.

The term "methionine aminopeptidase inhibitor", as used herein, refers to compounds which target, decrease or inhibit the activity of methionine aminopeptidase. Compounds which target, decrease or inhibit the activity of methionine aminopeptidase are, e.g., bengamide or a derivative thereof.

The term "proteasome inhibitor", as used herein, refers to compounds which target, decrease or inhibit the activity of the proteasome. Compounds which target, decrease or inhibit the activity of the proteasome include, e.g., PS-341 and MLN 341.

The term "matrix metalloproteinase inhibitor" or "MMP inhibitor", as used herein, includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies", as used herein, includes, but is not limited to, FMS-like tyrosine kinase inhibitors, e.g., compounds targeting, decreasing or inhibiting the activity of FMS-like tyrosine kinase receptors (Flt-3R); interferon, 1-b-D-arabinofuransylcytosine (ara-c) and bisulfan; and ALK inhibitors, e.g., compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g., PKC412, midostaurin, a staurosporine derivative, SU1 1248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90, e.g., 17-allylamino, 17-demethoxygeldanamycin (17AAG), a geldanamycin derivative, other geldanamycin related compounds, radicicol and HDAC inhibitors.

The term "antiproliferative antibodies", as used herein, includes, but is not limited to, trastuzumab (HERCEPTIN™), Trastuzumab-DM1, erlotinib (TARCEVA™), bevacizumab (AVASTIN™), rituximab (RITUXAN®), PR064553 (anti-CD40) and 2C4 antibody. By antibodies is meant, e.g., intact monoclonal antibodies, polyclonal antibodies, multispecific antibodies formed from at least two intact antibodies, and antibodies fragments so long as they exhibit the desired biological activity. For the treatment of acute myeloid leukemia (AML), compounds disclosed herein can be used in combination with standard leukemia therapies, especially in combination with therapies used for the treatment of AML. In particular, compounds disclosed herein can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g., Patents International, e.g., IMS World Publications.

The above-mentioned compounds, which can be used in combination with a compound disclosed herein, can be prepared and administered as described in the art, such as in the documents cited above.

A compound disclosed herein may also be used to advantage in combination with known therapeutic processes, e.g., surgery, the administration of hormones or especially radiation (in but a few examples, gamma radiation, neutron beam radiotherapy, electron beam radiotherapy, proton therapy, brachytherapy, and systemic radioactive isotopes, to name a few). A compound disclosed herein may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound disclosed herein and a combination partner may be administered independently at the same time or separately within time intervals that especially allow that the combination partners show a cooperative, e.g., synergistic, effect or any combination thereof. The terms "coadministration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound disclosed herein and a combination partner, are both administered to a patient simultaneously in the form of a single entity or dosage. The term "non-fixed combination" means that the active ingredients, e.g. a compound disclosed herein and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

Methods of Treatment

In one embodiment, the methods of treatment disclosed herein comprise administering a safe and effective amount of a compound or a pharmaceutically composition disclosed herein to a patient in need thereof. Individual embodiments disclosed herein include methods of treating any one of the above-mentioned disorders by administering a safe and effective amount of a compound disclosed herein or a pharmaceutical composition containing a compound disclosed herein to a patient in need thereof.

In one embodiment, the compounds disclosed herein or pharmaceutically compositions containing the compounds disclosed herein may be administered by any suitable route of administration, including both systemic administration and topical administration. Systemic administration includes oral administration, parenteral administration, transdermal administration and rectal administration. Parenteral administration is typically by injection or infusion, including intravenous, intramuscular, and subcutaneous injection or infusion. Topical administration includes application to the skin as well as intraocular, otic, intravaginal, inhaled and intranasal administration. In one embodiment, the compounds disclosed herein or pharmaceutical compositions containing the compounds disclosed herein may be administered orally. In another embodiment, the compounds disclosed herein or pharmaceutically compositions containing the compounds disclosed herein may be administered by inhalation. In a further embodiment, the compounds disclosed herein or pharmaceutical compositions containing the compounds disclosed herein may be administered intranasally.

In another embodiment, the compounds disclosed herein or pharmaceutically compositions containing the compounds disclosed herein may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound disclosed herein or a pharmaceutical composition containing a compound disclosed herein depend on the pharmacokinetic properties of that compound, such as absorption, distribution, and half-life, which can be determined by the skilled artisan. In addition, suitable dosing regimens, including the duration such regimens are administered, for a compound disclosed herein or a pharmaceutical composition containing a compound disclosed herein depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compound of the present invention may be administered either simultaneously with, or before or after, one or more other therapeutic agent. The compound of the present invention may be administered separately, by the same or different route of administration, or together in the same pharmaceutical composition as the other agents.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease. The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution.

In one embodiment, the therapeutically effective dose is from about 0.1 mg to about 2,000 mg per day of a compound provided herein. The pharmaceutical compositions therefore should provide a dosage of from about 0.1 mg to about 2000 mg of the compound. In certain embodiments, pharmaceutical dosage unit forms are prepared to provide from about 1 mg to about 2000 mg, from about 10 mg to about 1000 mg, from about 20 mg to about 500 mg or from about 25 mg to about 250 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

Additionally, the compounds disclosed herein may be administered as prodrugs. As used herein, a "prodrug" of a compound disclosed herein is a functional derivative of the compound which, upon administration to a patient, eventually liberates the compound disclosed herein in vivo. Administration of a compound disclosed herein as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

General Synthetic Procedures

In order to illustrate the invention, the following examples are included. However, it is to be understood that these examples do not limit the invention and are only meant to suggest a method of practicing the invention.

Generally, the compounds in this invention may be prepared by methods described herein, wherein the substituents are as defined for Formula (I), above, except where further noted. The following non-limiting schemes and examples are presented to further exemplify the invention. Persons skilled in the art will recognize that the chemical reactions described herein may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Arco Chemical Company and Alfa Chemical Company, Shanghai Medpep. Co Ltd, Aladdin-Shanghai Jinchun Reagents, Ltd, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tainjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexanes, DMA and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

$^1$H NMR spectra were recorded with a Bruker 400 MHz or 600 MHz spectrometer at ambient temperature. $^1$H NMR spectra were obtained as $CDCl_3$, DMSO-$d_6$, $CD_3OD$ or acetone-$d_6$ solutions (reported in ppm), using TMS (0 ppm) or chloroform (7.26 ppm) as the reference standard. When peak multiplicities are reported, the following abbreviations are used: s (singlet), d (doublet), t (triplet), m (multiplet), br (broadened), dd (doublet of doublets), dt (doublet of triplets), td (triplet of doublets). Coupling constants, when given, are reported in Hertz (Hz).

Low-resolution mass spectral (MS) data were generally determined on an Agilent 6120 quadrupole HPLC-MS (Zorbax SB-C18, 2.1×30 mm, 3.5 micron, 6 minutes run, 0.6 mL/min flow rate, 5% to 95% (0.1% formic acid in $CH_3CN$) in (0.1% formic acid in $H_2O$)) with UV detection at 210/254 nm and electrospray ionization (ESI).

Purities of compounds were assessed by Agilent 1260 pre-HPLC or Calesep pump 250 pre-HPLC (column: NOVASEP 50/80 mm DAC) with UV detection at 210 nm and 254 nm.

The following abbreviations are used throughout the specification:
AcOH, HAc, $CH_3COOH$ acetic acid
$Ac_2O$ acetic anhydride
BOC, Boc butyloxycarbonyl
n-BuOH butyl alcohol
Cbz-Cl benzyl chloroformate
$CDCl_3$ chloroform deuterated
DCM, $CH_2Cl_2$ methylene chloride
DIEA, DIPEA, i-$Pr_2$ NEt N,N-diisopropylethylamine
DMF dimethylformamide
DMAP 4-dimethylaminopyridine
DMSO dimethylsulfoxide
EDC, EDCI 1-(3-dimethylaminopropyl)-3-ethylcarbodiimide hydrochloride
EDTA ethylenediaminetetraacetic acid
$Et_3N$, TEA triethylamine
EtOAc, EA ethyl acetate
EtOH, $CH_3CH_2OH$ ethanol
g gram
h hour
hex hexane
HCl hydrochloric acid
HOAT 1-hydroxy-7-azabenzotriazole
MeCN, $CH_3CN$ acetonitrile
MeOH, $CH_3OH$ methanol
mL, ml milliliter
NaClO sodium hypochlorite
$Na_2CO_3$ sodium carbonate
NaH sodium hydride
$NaH_2PO_4$ sodium dihydrogen phosphate
NaOH sodium hydroxide
$Na_2SO_4$ sodium sulfate
Pd/C palladium on carbon
PE petroleum ether (60-90° C.)
RT, rt, r.t. room temperature
Rt retention time
$SOCl_2$ thionyl chloride
TFA trifluoroacetic acid Representative synthetic procedure for the preparation of the compound disclosed herein is outlined below in following Scheme 1. Unless otherwise indicated, each of W, $R^1$, $R^2$, $R^3$, $R^4$, $R^5$, $R^6$ and U carries the definition disclosed herein. X is Cl, Br, OH or $-OC(=O)C_1-C_4$alkyl.

Scheme 1:

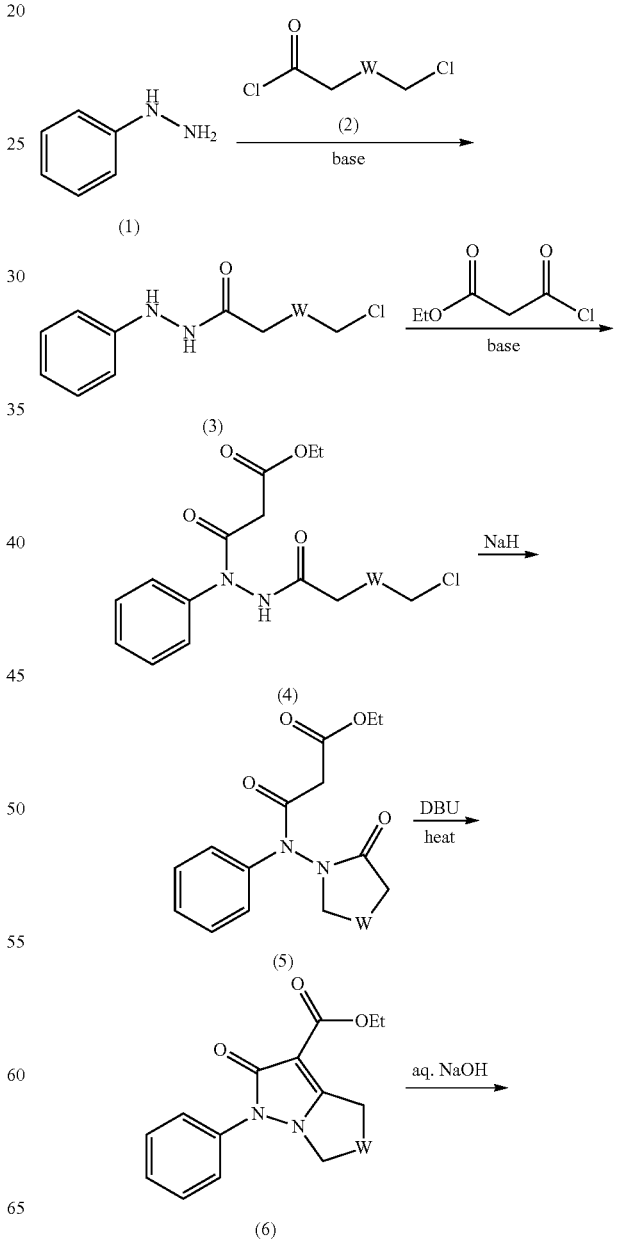

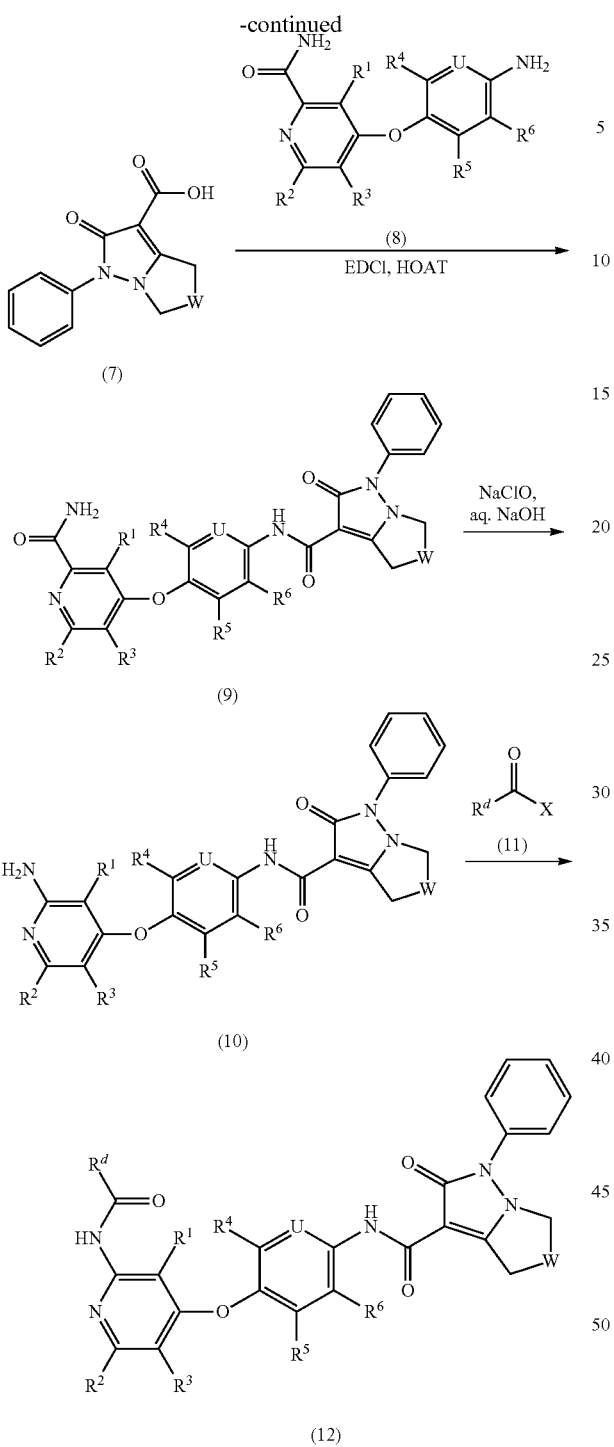

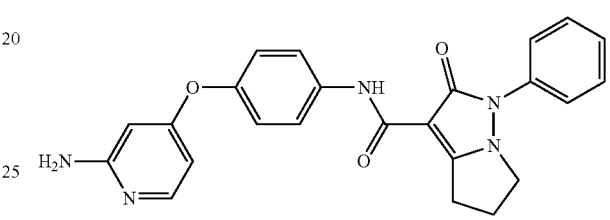

carboxyl through basic hydrolysis. Coupling of carboxylic acid (2) with compound (1) in the presence of coupling reagent such as EDCI/HOAT furnishes carbamoyl compound (2). The amide group in compound (2) is transformed to amine (7) with the aid of NaClO in aq. NaOH solution. Finally, condensation of compound (10) with compound (11) affords compound (1).

EXAMPLES

Example 1

N-(4-((2-aminopyridin-4-yl)oxy)phenyl)-2-oxo-1-phenyl-2,4,5,6-tetrahydro-1H-pyrrolo[1,2-b]pyrazole-3-carboxamide Step 1) 4-chloro-N'-phenylbutanehydrazide To a mixture of phenylhydrazine (16.0 g, 148.0 mmol) and 10% $Na_2CO_3$ (aq) (250 mL) in DCM (250 mL) was added 4-chlorobutanoyl chloride (20.9 g, 148.0 mmol) via a syringe at 0° C. The reaction was warmed up to r.t. and stirred overnight, then diluted with DCM (150 mL). The separated organic phase was washed with 2 M HCl (aq) (300 mL×3) followed with brine (150 mL), then dried over anhydrous $Na_2SO_4$, filtered and concentrated in vacuo. The resulted residue was recrystallized in EtOAc/n-hexane (50 mL/100 mL) to afford the title compound as a pale solid (14.7 g, 47%).

LC-MS (ESI, pos, ion) m/z: 213.1 $[M+H]^+$;
$^1$H NMR (400 MHz, $CDCl_3$) δ (ppm): 2.19-2.20 (m, 2H), 2.49 (t, J=7.1 Hz, 14.2 Hz, 2H), 3.54-3.67 (m, 2H), 5.79 (s, 1H), 6.87-6.80 (m, 2H), 6.92-6.95 (m, 1H), 7.24-7.32 (m, 2H), 7.38 (s, 1H).

Step 2) ethyl 3-(2-(4-chlorobutanoyl)-1-phenylhydrazinyl)-3-oxopropanoate

To a solution of 3-ethoxy-3-oxopropanoic acid (14.9 g, 112.8 mmol) in toluene (226 mL) was added $SOCl_2$ (26.6 g, 225.6 mmol). The reaction was heated at 110° C. for 4 h, and then concentrated in vacuo to give ethyl 3-chloro-3-oxopropanoate as brown oil, which was used for the next step immediately without further purification.

To a suspension of 4-chloro-N'-phenylbutanehydrazide (12 g, 56.4 mmol) and $Na_2CO_3$ (26.9 g, 253.8 mmol) in DCM (226 mL) was added a solution of ethyl 3-chloro-3-oxopropanoate in DCM (30 mL) slowly. The reaction was stirred at r.t. overnight, and then filtered through a pad of Celite®. The filtrate was diluted with DCM/water (100 mL/50 mL). The organic phase was separated and the aqueous phase was extracted with EtOAc (200 mL). The combined organic phases were dried over anhydrous $Na_2SO_4$, filtered and concentrated in vacuo. The resulted The compound disclosed herein can be prepared according to the general synthetic methods illustrated in Scheme 1 and described in details in the examples. As showing in Scheme 1, phenylhydrazine (1) is acylated with compound (2) under basic conditions to give compound (3). Compound (3) is then treated with ethyl 3-chloro-3-oxopropanoate to furnish compound (4). Subsequent self-cyclization of compound (4) can be accomplished with the aid of a base, such as NaH, to afford compound (5), which is then transformed to compound (6) via intramolecular condensation under basic conditions. The ester group in (6) is converted to residue was purified by a silica gel column chromatography (n-hexane/EtOAc (v/v)=3/2) to give the title compound as brown oil (6.2 g, 34%).

LC-MS (ESI, pos, ion) m/z: 327.2 [M+H]+;

1H NMR (400 MHz, CDCl3) δ (ppm): 8.41 (s, 1H), 7.44 (m, 5H), 4.13 (t, J=6.7 Hz, 2H), 3.59 (m, 2H), 3.36 (s, 2H), 2.44 (d, J=13.3 Hz, 2H), 2.12 (d, J=12.9 Hz, 2H), 1.27 (t, J=14.3 Hz, 3H).

Step 3) ethyl 3-oxo-3-((2-oxopyrrolidin-1-yl)(phenyl)amino)propanoate

To a solution of ethyl 3-(2-(4-chlorobutanoyl)-1-phenylhydrazinyl)-3-oxopropanoate (6.2 g, 19 mmol) in DMF (48 mL) was added NaH (60% dispersion in mineral oil, 2.3 g, 57 mmol) in portions at 0° C. The reaction was warmed up to r.t. and stirred for 4 h. The mixture was adjusted to pH=7 with saturated NaH2PO4 (aq), and then filtered. The organic phase was separated and the aqueous phase was extracted with EtOAc (200 mL×3). The combined organic phases were washed with brine (100 mL), dried over anhydrous Na2SO4, filtered and concentrated in vacuo. The resulted residue was purified by a silica gel column chromatography (EtOAc/PE (v/v)=4/5) to give the title compound as brown oil (5.0 g, 91%).

LC-MS (ESI, pos, ion) m/z: 290.1 [M+H]+;

1H NMR (400 MHz, CDCl3) δ (ppm): 7.38-7.52 (m, 5H), 4.17-4.25 (m, 2H), 3.48-3.55 (m, 2H), 3.31 (s, 2H), 2.37-2.54 (m, 2H), 2.01-2.18 (m, 2H), 1.25-1.33 (m, 3H).

Step 4) ethyl 2-oxo-1-phenyl-2,4,5,6-tetrahydro-1H-pyrrolo[1,2-b]pyrazole-3-carboxylate A solution of ethyl 3-oxo-3-((2-oxopyrrolidin-1-yl)(phenyl)amino)propanoate (3.3 g, 11.4 mmol) in DBU (10.0 mL) was stirred at 50° C. for 5 h, then cooled to r.t. and diluted with water (20 mL). The mixture was adjust to pH 7 with saturated NaH2PO4 (aq), and then extracted with DCM (20 mL×3). The combined organic phases were washed with brine (20 mL), dried over anhydrous Na2SO4, filtered and concentrated in vacuo. The resulted residue was purified by a silica gel column chromatography (EtOAc/n-hexane (v/v)=4/5) to give the title compound as a white solid (2.45 g, 79%).

LC-MS (ESI, pos, ion) m/z: 273.2 [M+H]+;

1H NMR (400 MHz, CDCl3) δ (ppm): 7.46 (t, J=7.8 Hz, 2H), 7.41-7.37 (m, 2H), 7.32 (d, J=7.3 Hz, 1H), 4.33 (q, J=7.1 Hz, 2H), 3.69 (t, J=6.9 Hz, 2H), 3.21 (t, J=7.4 Hz, 2H), 2.51-2.44 (m, 2H), 1.38 (d, J=7.1 Hz, 3H).

Step 5) 2-oxo-1-phenyl-2,4,5,6-tetrahydro-1H-pyrrolo[1,2-b]pyrazole-3-carboxylic acid To a solution of ethyl 2-oxo-1-phenyl-2,4,5,6-tetrahydro-1H-pyrrolo[1,2-b]pyrazole-3-carboxylate (2.0 g, 7.3 mmol) in EtOH (10 mL) was added 1.6 M NaOH (aq) (10 mL). The reaction was stirred at r.t. overnight, then concentrated in vacuo to remove EtOH. The resulted residue was washed with DCM (10 mL×2), and then adjust to pH 2 with 2 M HCl (aq). The precipitate was collected by filtration to give the title compound as a white solid (1.5 g, 84%).

LC-MS (ESI, pos, ion) m/z: 245.1 [M+H]+;

1H NMR (400 MHz, CDCl3) δ (ppm): 7.55 (t, J=7.7 Hz, 2H), 7.43 (t, J=9.1 Hz, 3H), 3.82 (t, J=6.9 Hz, 2H), 3.29 (t, J=7.4 Hz, 2H), 2.57 (m, 2H).

Step 6) N-(4-((2-carbamoylpyridin-4-yl)oxy)phenyl)-2-oxo-1-phenyl-2,4,5,6-etrahydro-1H-pyrrolo[1,2-b]pyrazole-3-carboxamide To a solution of 4-(4-aminophenoxy)picolinamide (450 mg, 1.96 mmol), 2-oxo-1-phenyl-2,4,5,6-tetrahydro-1H-pyrrolo[1,2-b]pyrazole-3-carboxylic acid (503 mg, 2.06 mmol) and HOAT (53.4 mg, 0.39 mmol) in DCM (10 mL) was added EDCI (564 mg, 2.94 mmol) in portions. The reaction was heated at 45° C. overnight, then cooled to r.t. and diluted with EtOAc/water (6 mL/6 mL). The mixture was continued to stir at r.t. for 1 h, and then filtered. The solid was collected and dried in vacuo at 60° C. for 5 h to afford the title compound as a pale-yellow solid (667 mg, 75%).

LC-MS (ESI, pos, ion) m/z: 456.2 [M+H]+;

1H NMR (400 MHz, CDCl3) δ (ppm): 10.26 (s, 1H), 8.41 (d, J=5.6 Hz, 1H), 7.85 (s, 1H), 7.79-7.74 (m, 3H), 7.55 (t, J=7.8 Hz, 2H), 7.47-7.38 (m, 3H), 7.07 (d, J=8.9 Hz, 2H), 6.98 (dd, J=5.6 Hz, 2.6 Hz, 1H), 5.54 (s, 1H), 3.74 (t, J=6.9 Hz, 2H), 3.35 (t, J=7.4 Hz, 2H), 2.56 (m, 2H).

Step 7) N-(4-((2-aminopyridin-4-yl)oxy)phenyl)-2-oxo-1-phenyl-2,4,5,6-tetrahydro-1H-pyrrolo[1,2-b]pyrazole-3-carboxamide To a solution of N-(4-((2-carbamoylpyridin-4-yl)oxy)phenyl)-2-oxo-1-phenyl-2,4,5,6-tetrahydro-1H-pyrrolo[1,2-b]pyrazole-3-carboxamide (667 mg, 1.94 mmol) in dioxane/MeOH (16 mL, v/v=1/1) was added a mixed solution of NaOCl (5.5% free Cl ion, 5 mL) and aq. NaOH (2.5 M, 5 mL) dropwise at 0° C. The reaction was stirred at 0° C. for 2 h, then heated to 80° C. and stirred for 3 h. The mixture was cooled down to 0° C., followed by an addition of water (15 mL). The precipitate was collected by filtration to give the title compound as a pale solid (300 mg, 48%).

LC-MS (ESI, pos, ion) m/z: 428.2 [M+H]+;

Q-TOF (ESI, pos, ion) m/z: 428.1717 [M+H]+;

1H NMR (600 MHz, CDCl3) δ (ppm): 10.22 (s, 1H), 7.93 (d, J=5.7 Hz, 1H), 7.72 (d, J=8.8 Hz, 2H), 7.55 (t, J=7.8 Hz, 2H), 7.48-7.43 (m, 2H), 7.40 (t, J=7.4 Hz, 1H), 7.06 (d, J=8.8 Hz, 2H), 6.32 (dd, J=5.8, 1.9 Hz, 1H), 5.96 (s, 1H), 4.47 (s, 2H), 3.74 (t, J=6.9 Hz, 2H), 3.34 (t, J=7.4 Hz, 2H), 2.56 (m, 2H);

13C NMR (150 MHz, CDCl3) δ (ppm): 166.9, 166.3, 162.4, 160.8, 160.0, 149.7, 149.3, 135.8, 134.6, 129.5, 127.5, 123.1, 121.5, 121.2, 104.2, 98.8, 95.0, 49.6, 29.7, 25.6, 22.2.

Example 2

N-(4-((2-(cyclopropanecarboxamido)pyridin-4-yl)oxy)phenyl)-2-oxo-1-phenyl-2,4,5,6-tetrahydro-1H-pyrrolo[1,2-b]pyrazole-3-carboxamide

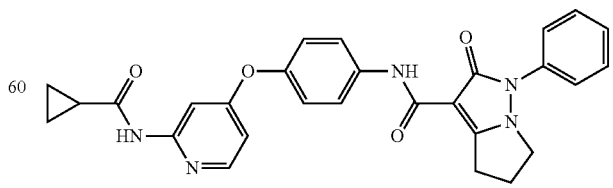

To a solution of N-(4-((2-aminopyridin-4-yl)oxy)phenyl)-2-oxo-1-phenyl-2,4,5,6-tetrahydro-1H-pyrrolo[1,2-b]pyrazole-3-carboxamide (150 mg, 0.35 mmol) and pyridine (1.4 mL) in MeCN (2 mL) was added a solution of cyclopropanecarbonyl chloride (110 mg, 1.05 mmol) and DMAP (128.3 mg, 1.05 mmol) in MeCN (1.4 mL). The reaction was heated at 60° C. overnight, then cooled to r.t. and diluted with DCM/water (10 mL/15 mL). The separated organic phase was washed with water (6 mL×3), dried over anhydrous Na$_2$SO$_4$, filtered and concentrated in vacuo. The resulted residue was recrystallized in EtOAc/PE (8 mL, v/v=1/3) to give the title compound as a pale solid (109 mg, 60%).

LC-MS (ESI, pos, ion) m/z: 496.3 [M+H]$^+$;

Q-TOF (ESI, pos, ion) m/z: 496.1981 [M+H]$^+$;

$^1$H NMR (600 MHz, CDCl$_3$) δ (ppm): 10.21 (s, 1H), 8.44 (s, 1H), 8.09 (d, J=5.8 Hz, 1H), 7.83 (s, 1H), 7.74 (d, J=8.8 Hz, 2H), 7.54 (t, J=7.8 Hz, 2H), 7.45 (d, J=7.6 Hz, 2H), 7.40 (t, J=7.4 Hz, 1H), 7.06 (d, J=8.8 Hz, 2H), 6.56 (dd, J=5.7 Hz, 2.2 Hz, 1H), 3.73 (t, J=6.9 Hz, 2H), 3.34 (t, J=7.4 Hz, 2H), 2.55 (p, J=7.1 Hz, 2H), 1.53 (dt, J=11.9 Hz, 3.9 Hz, 1H), 1.12-1.07 (m, 2H), 0.90-0.84 (m, 2H);

$^{13}$C NMR (150 MHz, CDCl$_3$) δ (ppm): 172.1, 166.9, 166.3, 162.4, 160.7, 153.1, 149.6, 148.9, 136.0, 134.7, 129.5, 127.5, 123.1, 121.2, 108.2, 101.9, 98.9, 49.6, 25.6, 22.2, 15.8, 8.3.

Example 3

N-(4-((2-acetamidopyridin-4-yl)oxy)phenyl)-2-oxo-1-phenyl-2,4,5,6-tetrahydro-1H-pyrrolo[1,2-b]pyrazole-3-carboxamide

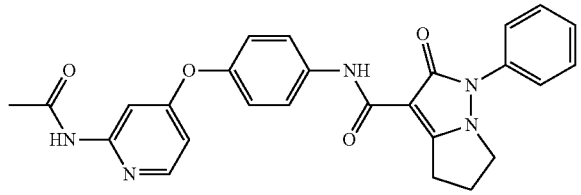 [SMILES: CC(=O)Nc1cc(Oc2ccc(NC(=O)c3c4n(n(-c5ccccc5)c3=O)CCC4)cc2)ccn1]

To a solution of N-(4-((2-aminopyridin-4-yl)oxy)phenyl)-2-oxo-1-phenyl-2,4,5,6-tetrahydro-1H-pyrrolo[1,2-b]pyrazole-3-carboxamide (100 mg, 0.23 mmol) in acetic anhydride (2 mL) was added Et$_3$N (142 mg, 1.4 mmol). The reaction was stirred at 30° C. overnight, and then concentrated in vacuo. The resulted residue was purified by a column chromatography on silica gel (100% EtOAc) to afford the title compound as a pale solid (38 mg, 35%).

LC-MS (ESI, pos, ion) m/z: 470.2 [M+H]$^+$;

Q-TOF (ESI, pos, ion) m/z: 470.1827 [M+H]$^+$;

$^1$H NMR (600 MHz, CDCl$_3$) δ (ppm): 10.22 (s, 1H), 8.27 (s, 1H), 8.08 (d, J=5.8 Hz, 1H), 7.86 (s, 1H), 7.75 (d, J=8.9 Hz, 2H), 7.54 (t, J=7.9 Hz, 2H), 7.44 (d, J=7.5 Hz, 2H), 7.40 (t, J=7.4 Hz, 1H), 7.07 (d, J=8.9 Hz, 2H), 6.56 (dd, J=5.8 Hz, 2.2 Hz, 1H), 3.73 (t, J=6.9 Hz, 2H), 3.34 (t, J=7.4 Hz, 2H), 2.58-2.50 (m, 2H), 2.18 (s, 3H);

$^{13}$C NMR (150 MHz, CDCl$_3$) δ (ppm): 167.0, 166.3, 162.4, 160.8, 153.0, 149.5, 148.9, 136.1, 134.7, 129.5, 127.5, 123.1, 121.3, 121.2, 108.2, 102.1, 98.9, 49.6, 25.6, 24.7, 22.2.

Example 4

N-(4-((2-aminopyridin-4-yl)oxy)-3-fluorophenyl)-2-oxo-1-phenyl-2,4,5,6-tetrahydro-1H-pyrrolo[1,2-b]pyrazole-3-carboxamide

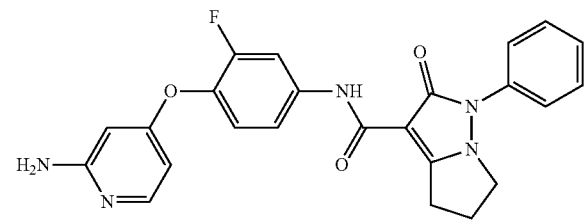 [SMILES: Nc1cc(Oc2ccc(NC(=O)c3c4n(n(-c5ccccc5)c3=O)CCC4)cc2F)ccn1]

Step 1) N-(4-((2-carbamoylpyridin-4-yl)oxy)-3-fluorophenyl)-2-oxo-1-phenyl-2,4,5,6-tetrahydro-1H-pyrrolo[1,2-b]pyrazole-3-carboxamide To a solution of 4-(4-amino-2-fluorophenoxy)picolinamide (322 mg, 1.30 mmol), 2-oxo-1-phenyl-2,4,5,6-tetrahydro-1H-pyrrolo[1,2-b]pyrazole-3-carboxylic acid (325 mg, 1.33 mmol) and HOAT (35.4 mg, 0.26 mmol) in DCM (10 mL) was added EDCI (382 mg, 1.99 mmol) in portions. The reaction was heated at 50° C. overnight, then cooled to r.t. and concentrated in vacuo. The residue was diluted with 1 M HCl and stirred for 30 min. The precipitate was collected by filteration to give the title compound as a pale solid (260 mg, 42%).

LC-MS (ESI, pos, ion) m/z: 474.3 [M+H]$^+$;

$^1$H NMR (400 MHz, DMSO-d$_6$) δ (ppm): 10.40 (s, 1H), 8.55 (d, J=5.6 Hz, 1H), 8.15 (s, 1H), 8.01 (d, J=11.9 Hz, 1H), 7.74 (s, 1H), 7.60-7.51 (m, 4H), 7.45-7.39 (m, 4H), 7.23 (dd, J=5.6 Hz, 2.6 Hz, 1H), 3.83 (t, J=7.0 Hz, 2H), 3.18 (t, J=7.4 Hz, 2H), 2.46-2.42 (m, 2H).

Step 2) N-(4-((2-aminopyridin-4-yl)oxy)-3-fluorophenyl)-2-oxo-1-phenyl-2,4,5,6-tetrahydro-1H-pyrrolo[1,2-b]pyrazole-3-carboxamide To a solution of N-(4-((2-carbamoylpyridin-4-yl)oxy)-3-fluorophenyl)-2-oxo-1-phenyl-2,4,5,6-tetrahydro-1H-pyrrolo[1,2-b]pyrazole-3-carboxamide (261 mg, 0.551 mmol) in dioxane/MeOH (10 mL, v/v=1/1) was added a mixed solution of NaOCl (5.5% free Cl ion, 1.7 mL) and 2.5 M NaOH (aq) (0.3 mL) dropwise at 0° C. The reaction was stirred at 0° C. for 4 h, then heated to 80° C. and stirred further for 1 h. The mixture was cooled down to 0° C., followed by an addition of water (15 mL). The precipitate was collected by filtration to give the title compound as a brown solid (60 mg, 24%).

LC-MS (ESI, pos, ion) m/z: 446.2 [M+H]$^+$;

Q-TOF (ESI, pos, ion) m/z: 446.1627 [M+H]$^+$;

$^1$H NMR (600 MHz, DMSO-d$_6$) δ (ppm): 10.34 (s, 1H), 7.94 (d, J=12.9 Hz, 1H), 7.80 (d, J=5.5 Hz, 1H), 7.59-7.50 (m, 4H), 7.43 (t, J=6.9 Hz, 1H), 7.35 (d, J=8.3 Hz, 1H), 7.28 (t, J=8.8 Hz, 1H), 6.17 (d, J=3.6 Hz, 1H), 5.96 (s, 2H), 5.80 (s, 1H), 3.82 (s, 2H), 3.17 (d, J=6.9 Hz, 2H), 2.47-2.40 (m, 2H);

$^{13}$C NMR (150 MHz, DMSO-d$_6$) δ (ppm): 165.6, 165.6, 162.1, 161.6, 160.9, 153.3, 150.0, 135.9, 134.7, 129.8, 127.8, 124.6, 123.9, 116.0, 108.3, 108.2, 101.5, 96.5, 92.8, 49.9, 26.0, 22.2.

Example 5

N-(4-((2-(cyclopropanecarboxamido)pyridin-4-yl)oxy)-3-fluorophenyl)-2-oxo-1-phenyl-2,4,5,6-tetrahydro-1H-pyrrolo[1,2-b]pyrazole-3-carboxamide

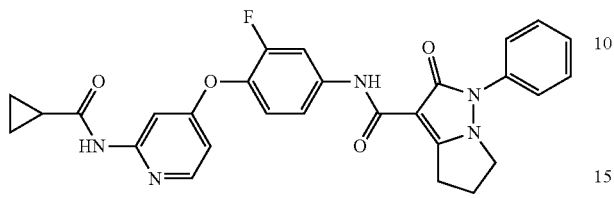

To a solution of N-(4-((2-aminopyridin-4-yl)oxy)-3-fluorophenyl)-2-oxo-1-phenyl-2,4,5,6-tetrahydro-1H-pyrrolo[1,2-b]pyrazole-3-carboxamide (22 mg, 0.05 mmol) and pyridine (0.2 mL) in MeCN (0.3 mL) was added a solution of cyclopropanecarbonyl chloride (15.5 mg, 0.15 mmol) and DMAP (18.3 mg, 0.15 mmol) in MeCN (0.2 mL). The reaction was heated at 60° C. overnight, then cooled to r.t. and diluted with DCM/water (6 mL/15 mL). The separated organic phase was washed with water (6 mL×3), dried over anhydrous $Na_2SO_4$, filtered and concentrated in vacuo. The resulted residue was purified by a column chromatography on silica gel (EtOAc/PE (v/v)=5/1) to afford the title compound as a pale-yellow solid (20 mg, 67%).

LC-MS (ESI, pos, ion) m/z: 514.3 [M+H]$^+$;
Q-TOF (ESI, pos, ion) m/z: 514.1883 [M+H]$^+$;
$^1$H NMR (600 MHz, CDCl$_3$) δ (ppm): 10.31 (s, 1H), 8.38 (s, 1H), 8.11 (d, J=5.8 Hz, 1H), 7.90 (dd, J=12.4 Hz, 2.2 Hz, 1H), 7.82 (s, 1H), 7.55 (t, J=7.8 Hz, 2H), 7.46-7.39 (m, 3H), 7.12 (t, J=8.7 Hz, 1H), 6.58 (dd, J=5.7 Hz, 2.2 Hz, 1H), 4.14 (q, J=7.1 Hz, 1H), 3.75 (t, J=6.9 Hz, 2H), 3.34 (t, J=7.4 Hz, 2H), 2.59-2.52 (m, 2H), 1.56-1.50 (m, 1H), 1.09 (dt, J=7.9 Hz, 4.0 Hz, 2H), 0.90-0.86 (m, 2H).

Example 6

N-(4-((2-acetamidopyridin-4-yl)oxy)-3-fluorophenyl)-2-oxo-1-phenyl-2,4,5,6-tetrahydro-1H-pyrrolo[1,2-b]pyrazole-3-carboxamide

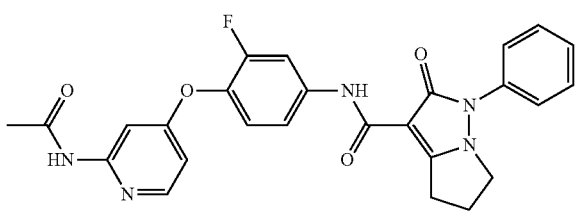 [SMILES: CC(=O)Nc1cc(Oc2ccc(NC(=O)c3c4n(n(-c5ccccc5)c3=O)CCC4)cc2F)ccn1]

To a solution of N-(4-((2-aminopyridin-4-yl)oxy)-3-fluorophenyl)-2-oxo-1-phenyl-2,4,5,6-tetrahydro-1H-pyrrolo[1,2-b]pyrazole-3-carboxamide (22 mg, 0.05 mmol) in acetic anhydride (1 mL) was added Et$_3$N (30 mg, 0.3 mmol). The reaction was stirred at 30° C. for 4 h, and then concentrated in vacuo. The resulted residue was purified by a column chromatography on silica gel (100% EtOAc) to afford the title compound as a pale-yellow solid (20 mg, 74%).

LC-MS (ESI, pos, ion) m/z: 488.3 [M+H]$^+$;
Q-TOF (ESI, pos, ion) m/z: 488.1733 [M+H]$^+$;
$^1$H NMR (600 MHz, CDCl$_3$) δ (ppm): 10.32 (s, 1H), 8.32 (s, 1H), 8.10 (d, J=5.6 Hz, 1H), 7.96-7.83 (m, 2H), 7.54 (t, J=7.4 Hz, 2H), 7.43 (dd, J=14.1 Hz, 7.7 Hz, 4H), 7.13 (t, J=8.6 Hz, 1H), 6.57 (d, J=3.8 Hz, 1H), 3.75 (t, J=6.6 Hz, 2H), 3.34 (t, J=7.0 Hz, 2H), 2.62-2.50 (m, 2H), 2.18 (s, 3H).

Example 7

N-(5-((2-aminopyridin-4-yl)oxy)pyridin-2-yl)-2-oxo-1-phenyl-1,2,4,5,6,7-hexahydropyrazolo[1,5-a]pyridine-3-carboxamide

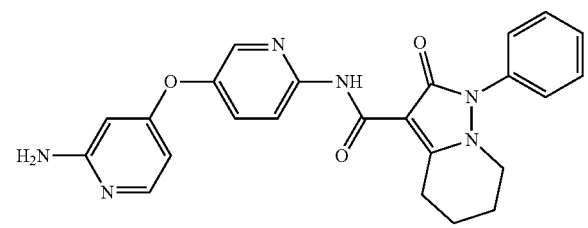 [SMILES: Nc1cc(Oc2ccc(NC(=O)c3c4n(n(-c5ccccc5)c3=O)CCCC4)nc2)ccn1]

Step 1) 5-chloro-N'-phenylpentanehydrazide

To a mixture of phenylhydrazine (21.6 g, 200.0 mmol) and 10% Na$_2$CO$_3$ (aq) (340 mL) in DCM (340 mL) was added 5-chloropentanoyl chloride (31.0 g, 200.0 mmol) via a syringe at 0° C. The reaction was warmed up to r.t., stirred overnight, and then diluted with DCM (150 mL). The separated organic phase was washed with 2 M HCl (aq) (250 mL×5) followed with brine (250 mL), then dried over anhydrous Na$_2$SO$_4$, filtered and concentrated in vacuo. The resulted residue was recrystallized in EtOAc/n-hexane (80 mL/240 mL) to afford the title compound as a pale solid (19.6 g, 44%).

LC-MS (ESI, pos, ion) m/z: 227.2 [M+H]$^+$;
$^1$H NMR (400 MHz, CDCl$_3$) δ (ppm): 7.44 (s, 1H), 7.27-7.22 (m, 2H), 6.95 (m, 2H), 6.79 (d, J=7.8 Hz, 1H), 5.78 (s, 1H), 3.58 (m, 2H), 2.32 (m, 2H), 1.87 (m, 2H), 1.81 (m, 2H).

Step 2) ethyl 3-(2-(5-chloropentanoyl)-1-phenylhydrazinyl)-3-oxopropanoate

To a solution of 3-ethoxy-3-oxopropanoic acid (38.5 g, 291 mmol) in toluene (290 mL) was added SOCl$_2$ (68.6 g, 582 mmol). The reaction was heated at 110° C. for 6 h, and then concentrated in vacuo to give ethyl 3-chloro-3-oxopropanoate as brown oil, which was used for the next step immediately without further purification.

To a suspension of 5-chloro-N'-phenylpentanehydrazide (22 g, 97 mmol) and Na$_2$CO$_3$ (31 g, 291 mmol) in DCM (582 mL) was added a solution of ethyl 3-chloro-3-oxopropanoate in DCM (50 mL) slowly. The reaction was stirred at r.t. overnight, and then filtered through a pad of Celite®. The filtrate was diluted with DCM/water (100 mL/50 mL). The separated organic phase was washed with water (150 mL×2) followed by brine (150 mL), then dried over anhydrous Na$_2$SO$_4$, filtered and concentrated in vacuo. The resulted residue was purified by a silica gel column chromatography (n-hexane/EtOAc (v/v)=3/2) to give the title compound as brown oil (25 g, 76%).

LC-MS (ESI, pos, ion) m/z: 341.2 [M+H]$^+$;

¹H NMR (400 MHz, CDCl₃) δ (ppm): 8.28 (s, 1H), 7.46-7.38 (m, 5H), 4.31-4.17 (m, 2H), 4.14 (m, 2H), 3.52 (m, 2H), 3.36 (s, 2H), 2.29 (m, 2H), 1.33 (m, 2H), 1.29-1.22 (m, 3H).

Step 3) ethyl 3-oxo-3-((2-oxopiperidin-1-yl)(phenyl)amino)propanoate

To a solution of ethyl 3-(2-(5-chloropentanoyl)-1-phenylhydrazinyl)-3-oxopropanoate (25 g, 73 mmol) in DMF (219 mL) was added NaH (60% dispersion in mineral oil, 8.8 g, 219 mmol) in portions at 0° C. The reaction was warmed up to r.t. and stirred overnight. The mixture was adjusted to pH 7 with saturated NaH₂PO₄ (aq), and then filtered. The organic phase was separated and the aqueous phase was extracted with EtOAc (200 mL×4). The combined organic phases were washed with brine (100 mL), dried over anhydrous Na₂SO₄, filtered and concentrated in vacuo to give the title compound as brown oil (20 g, 90%).

LC-MS (ESI, pos, ion) m/z: 305.2 [M+H]⁺.

Step 4) ethyl 2-oxo-1-phenyl-1,2,4,5,6,7-hexahydropyrazolo[1,5-a]pyridine-3-carboxylate A solution of ethyl 3-oxo-3-((2-oxopiperidin-1-yl)(phenyl)amino)propanoate (20 g, 66 mmol) in DBU (20.0 mL) was stirred at 50° C. overnight, then cooled to r.t. and diluted with water (20 mL). The mixture was adjusted to pH 7 with saturated NaH₂PO₄ (aq), and then extracted with DCM (100 mL×6). The combined organic phases were washed with brine (100 mL), dried over anhydrous Na₂SO₄, filtered and concentrated in vacuo to give the title compound as a yellow solid (17 g, 90%).

LC-MS (ESI, pos, ion) m/z: 287.1 [M+H]⁺;

¹H NMR (600 MHz, CDCl₃) δ (ppm): 7.50-7.47 (m, 2H), 7.40-7.36 (m, 1H), 7.34-7.32 (m, 2H), 4.33 (q, J=7.1 Hz, 2H), 3.53 (t, J=5.9 Hz, 2H), 3.22 (t, J=6.5 Hz, 2H), 2.07-2.04 (m, 2H), 1.93-1.89 (m, 2H), 1.39 (t, J=7.1 Hz, 3H).

Step 5) 2-oxo-1-phenyl-1,2,4,5,6,7-hexahydropyrazolo[1,5-a]pyridine-3-carboxylic acid To a solution of ethyl 2-oxo-1-phenyl-1,2,4,5,6,7-hexahydropyrazolo[1,5-a]pyridine-3-carboxylate (18 g, 62.8 mmol) in EtOH (100 mL) was added 1.6 M NaOH (aq) (100 mL). The reaction was stirred at r.t. overnight, and then concentrated in vacuo to remove EtOH. The resulted residue was washed with DCM (20 mL×2), and adjusted to pH 2 with 2 M HCl (aq). The precipitate was collected by filtration to give the title compound as a pale yellow solid (10.7 g, 66%).

LC-MS (ESI, pos, ion) m/z: 259.1 [M+H]⁺;

¹H NMR (600 MHz, CDCl₃) δ (ppm): 7.58-7.55 (m, 2H), 7.52-7.49 (m, 1H), 7.39-7.36 (m, 2H), 3.60 (t, J=6.0 Hz, 2H), 3.28 (t, J=6.5 Hz, 2H), 2.13-2.08 (m, 2H), 1.96-1.92 (m, 2H).

Step 6) N-(5-hydroxypyridin-2-yl)-2-oxo-1-phenyl-1,2,4,5,6,7-hexahydropyrazolo[1,5-a]pyridine-3-carboxamide To a solution of 6-aminopyridin-3-ol hydrochloride (2.55 g, 17.4 mmol) in DMF (23 mL) was added KOH (1.624 g, 29 mmol). The mixture was stirred at r.t. for 30 min, followed by an addition of 2-oxo-1-phenyl-1,2,4,5,6,7-hexahydropyrazolo[1,5-a]pyridine-3-carboxylic acid (3.0 g, 11.6 mmol), HOAT (316 mg, 2.32 mmol) and EDCI (4.48 g, 23.2 mmol). The reaction was heated at 60° C. overnight, then cooled to r.t., diluted with water (230 mL) and extracted with DCM (100 mL×3). The combined organic phases were washed with brine (100 mL), dried over anhydrous Na₂SO₄, filtered and concentrated in vacuo. The resulted residue was recrystallized in DCM/EtOAc/PE (30 mL/30 mL/30 mL) to give the title compound as a yellow solid (2.8 g, 69%).

LC-MS (ESI, pos, ion) m/z: 351.1 [M+H]⁺;

¹H NMR (400 MHz, CDCl₃) δ (ppm): 10.72 (s, 1H), 8.05 (d, J=8.9 Hz, 1H), 7.82 (d, J=2.8 Hz, 1H), 7.57 (d, J=7.7 Hz, 2H), 7.50 (dd, J=8.5 Hz, 6.2 Hz, 1H), 7.47-7.43 (m, 2H), 7.19 (dd, J=8.9 Hz, 2.9 Hz, 1H), 3.55 (t, J=5.8 Hz, 2H), 3.19 (d, J=6.3 Hz, 2H), 1.97 (d, J=5.7 Hz, 2H), 1.81 (d, J=5.8 Hz, 2H).

Step 7) N-(5-((2-carbamoylpyridin-4-yl)oxy)pyridin-2-yl)-2-oxo-1-phenyl-1,2,4,5,6,7-hexahydropyrazolo[1,5-a]pyridine-3-carboxamide To a solution of 4-chloropicolinamide (1.44 g, 9.2 mmol) and N-(5-hydroxypyridin-2-yl)-2-oxo-1-phenyl-1,2,4,5,6,7-hexahydropyrazolo[1,5-a]pyridine-3-carboxamide (2.80 g, 8.0 mmol) in DMF (16 mL) was added t-BuOK (1.80 g, 16.0 mmol). The reaction was heated at 130° C. overnight, then cooled to r.t. and diluted with water (160 mL). The mixture was continued to stir at r.t. overnight, then filtered. The solid was dried in vacuo to give the title compound as a brown solid (2.9 g, 78%).

LC-MS (ESI, pos, ion) m/z: 471.1 [M+H]⁺;

¹H NMR (400 MHz, CDCl₃) δ (ppm): 11.15 (s, 1H), 8.44 (d, J=5.6 Hz, 1H), 8.38 (d, J=9.1 Hz, 1H), 8.17 (d, J=2.7 Hz, 1H), 7.84 (s, 1H), 7.76 (d, J=2.5 Hz, 1H), 7.55 (t, J=7.6 Hz, 2H), 7.48-7.42 (m, 3H), 7.41-7.38 (m, 2H), 6.98 (dd, J=5.6 Hz, 2.6 Hz, 1H), 5.60 (s, 1H), 3.60 (t, J=5.9 Hz, 2H), 3.41 (t, J=6.4 Hz, 2H), 2.12-2.08 (m, 2H), 1.99-1.94 (m, 2H).

Step 8) N-(5-((2-aminopyridin-4-yl)oxy)pyridin-2-yl)-2-oxo-1-phenyl-1,2,4,5,6,7-hexahydropyrazolo[1,5-a]pyridine-3-carboxamide To a solution of N-(5-((2-carbamoylpyridin-4-yl)oxy)pyridin-2-yl)-2-oxo-1-phenyl-1,2,4,5,6,7-hexahydropyrazolo[1,5-a]pyridine-3-carboxamide (2.9 g, 6.2 mmol) in dioxane/MeOH (62 mL, v/v=1/1) was added a mixed solution of NaOCl (5.5% free Cl ion, 30 mL) and 2.5 M NaOH (aq) (3.1 mL) at 0° C. The reaction was stirred at 0° C. for 4 h, then heated to 60° C. and stirred overnight. The mixture was cooled down to 0° C., followed by an addition of water (360 mL). The precipitate was collected by filtration to give the title compound as a pale-yellow solid (1.02 g, 37%).

LC-MS (ESI, pos, ion) m/z: 443.1 [M+H]⁺;

Q-TOF (ESI, pos, ion) m/z: 443.1840 [M+H]⁺;

¹H NMR (600 MHz, CDCl₃) δ (ppm): 11.05 (s, 1H), 8.29 (d, J=9.0 Hz, 1H), 8.16 (d, J=2.8 Hz, 1H), 7.80 (d, J=5.8 Hz, 1H), 7.64 (dd, J=9.0 Hz, 2.8 Hz, 1H), 7.59 (t, J=7.7 Hz, 2H), 7.51 (t, J=7.4 Hz, 1H), 7.46 (d, J=7.5 Hz, 2H), 6.17 (dd, J=5.8 Hz, 2.2 Hz, 1H), 5.95 (s, 2H), 5.83 (d, J=2.0 Hz, 1H), 3.57 (t, J=5.8 Hz, 2H), 3.21 (t, J=6.3 Hz, 2H), 2.01-1.95 (m, 2H), 1.84-1.79 (m, 2H);

¹³C NMR (150 MHz, CDCl₃) δ (ppm): 165.8, 162.9, 162.1, 161.6, 153.8, 150.1, 149.4, 146.6, 141.5, 133.0, 131.5, 129.9, 129.4, 128.0, 114.4, 102.2, 95.9, 93.8, 46.6, 23.9, 22.2, 18.8.

Example 8

N-(5-((2-(cyclopropanecarboxamido)pyridin-4-yl)oxy)pyridin-2-yl)-2-oxo-1-phenyl-1,2,4,5,6,7-hexahydropyrazolo[1,5-a]pyridine-3-carboxamide

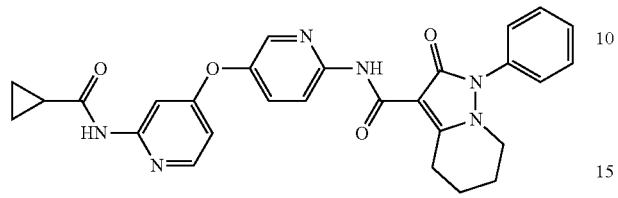

To a solution of N-(5-((2-aminopyridin-4-yl)oxy)pyridin-2-yl)-2-oxo-1-phenyl-1,2,4,5,6,7-hexahydropyrazolo[1,5-a]pyridine-3-carboxamide (100 mg, 0.226 mmol) in pyridine (1 mL) was added cyclopropanecarbonyl chloride (142 mg, 1.36 mmol) dropwise at 0° C. The reaction was warmed up to r.t. and stirred overnight. The mixture was diluted with water (10 mL) and extracted with DCM (6 mL×3). The combined organic phases were washed with brine (10 mL), dried over anhydrous $Na_2SO_4$, filtered and concentrated in vacuo. The resulted residue was purified by a column chromatography on silica gel (DCM/MeOH (v/v)=40/1) to afford the title compound as a pale-yellow solid (37 mg, 32%).

LC-MS (ESI, pos, ion) m/z: 511.1 [M+H]$^+$;
Q-TOF (ESI, pos, ion) m/z: 511.2125 [M+H]$^+$;
$^1$H NMR (600 MHz, CDCl$_3$) δ (ppm): 11.10 (s, 1H), 8.60 (s, 1H), 8.34 (d, J=9.0 Hz, 1H), 8.15 (d, J=2.7 Hz, 1H), 8.11 (d, J=5.8 Hz, 1H), 7.86 (s, 1H), 7.54 (t, J=7.7 Hz, 2H), 7.47-7.41 (m, 2H), 7.39 (d, J=7.8 Hz, 2H), 6.56 (dd, J=5.7 Hz, 2.1 Hz, 1H), 3.59 (t, J=5.9 Hz, 2H), 3.40 (t, J=6.4 Hz, 2H), 2.13-2.07 (m, 2H), 1.97-1.91 (m, 2H), 1.59-1.52 (m, 1H), 1.11-1.07 (m, 2H), 0.90-0.89 (m, 2H).

Example 9

N-(5-((2-acetamidopyridin-4-yl)oxy)pyridin-2-yl)-2-oxo-1-phenyl-1,2,4,5,6,7-hexahydropyrazolo[1,5-a]pyridine-3-carboxamide

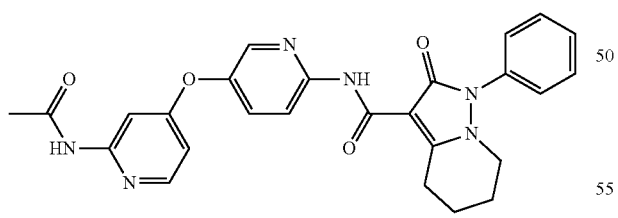

To a solution of N-(5-((2-aminopyridin-4-yl)oxy)pyridin-2-yl)-2-oxo-1-phenyl-1,2,4,5,6,7-hexahydropyrazolo[1,5-a]pyridine-3-carboxamide (100 mg, 0.226 mmol) in acetic anhydride (2 mL) was added Et$_3$N (137 mg, 1.36 mmol). The reaction was stirred at 30° C. overnight, and then concentrated in vacuo. The residue was purified by a column chromatography on silica gel (DCM/MeOH (v/v)=40/1) to afford the title compound as a pale-yellow solid (55 mg, 50%).

LC-MS (ESI, pos, ion) m/z: 485.3 [M+H]$^+$;
$^1$H NMR (600 MHz, CDCl$_3$) δ (ppm): 11.09 (s, 1H), 10.57 (s, 1H), 8.32 (d, J=9.0 Hz, 1H), 8.21 (dd, J=14.2 Hz, 4.3 Hz, 2H), 7.72-7.66 (m, 2H), 7.60 (t, J=7.7 Hz, 2H), 7.52 (t, J=7.4 Hz, 1H), 7.48 (d, J=7.8 Hz, 2H), 6.70 (dd, J=5.7 Hz, 2.3 Hz, 1H), 3.58 (t, J=5.8 Hz, 2H), 3.22 (t, J=6.3 Hz, 2H), 2.01-1.96 (m, 2H), 1.85-1.80 (m, 2H), 1.24 (s, 3H).

Example 10

N-(5-((2-aminopyridin-4-yl)oxy)pyridin-2-yl)-2-oxo-1-phenyl-2,4,6,7-tetrahydro-1H-pyrazolo[5,1-c][1,4]oxazine-3-carboxamide

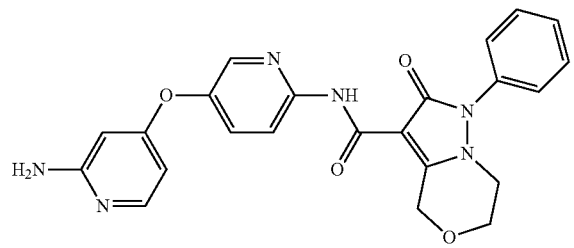 [SMILES: Nc1cc(Oc2ccc(NC(=O)c3c4n(n(-c5ccccc5)c3=O)CCOC4)nc2)ccn1]

Step 1) 2-(2-(2-(tert-butoxycarbonyl)-2-phenylhydrazinyl)-2-oxoethoxy)acetic acid To a solution of tert-butyl 1-phenylhydrazinecarboxylate (25.2 g, 121 mmol) and diglycolic anhydride (16.8 g, 145.2 mmol) in 190 mL DMF was added sodium carbonate (12.8 g, 121 mmol) at room temperature. The reaction was stirred at r.t. overnight, and then filtered through a pad of Celite®, the solid mass was washed with EtOAc (50 mL). The filtrate was concentrated in vacuo. The residue was added H$_2$O (180 mL) and extracted by EtOAc (50 mL×5), the water phase was adjusted to pH 6-7 with NaH$_2$PO$_4$ (aq), and then was extracted with EtOAc (50 mL). The organic phase was dried over anhydrous Na$_2$SO$_4$, filtered and concentrated in vacuo to give the title compound as yellow oil (28.3 g, 73%).

LC-MS (ESI, pos, ion): 225.2 [M-100+H]$^+$;
$^1$H NMR (400 MHz, DMSO-d$_6$) δ (ppm): 10.67 (s, 1H), 7.39-7.30 (m, 4H), 7.20-7.10 (m, 1H), 4.15 (s, 4H), 1.42 (s, 9H).

Step 2) tert-butyl 2-(2-(2-hydroxyethoxy)acetyl)-1-phenylhydrazinecarboxylate To a solution of 2-(2-(2-(tert-butoxycarbonyl)-2-phenylhydrazinyl)-2-oxoethoxy)acetic acid (10.7 g, 33 mmol) in 140 mL THF at 0° C. was added triethylamine (9.24 mL, 66 mmol) followed by isobutyl chlorocarbonate (5.2 mL, 39.6 mmol) via a syringe. The reaction became cloudy due to the formation of Et$_3$N-HCl salt. The reaction was stirred at 0° C. for 2 h and then filtered. The filtrate was cooled to 0° C. and NaBH$_4$ (5 g, 132 mmol) in 60 mL of H$_2$O was added. The reaction was stirred at 0° C. for 1 h, then the mixture was added H$_2$O (100 mL) and extracted with EtOAc (200 mL×2). The combined organic phase was washed with 1 M NaH$_2$PO$_4$ (100 mL) aqueous solution, followed with brine (100 mL), then dried over anhydrous Na$_2$SO$_4$, filtered and the filtrate was concentrated in vacuo to afford title compound as yellow oil (8.7 g, 85%).

LC-MS (ESI, neg, ion): 309.2 [M−H]$^-$;

¹H NMR (400 MHz, DMSO-d₆) δ (ppm): 10.54 (s, 1H), 7.60-7.23 (m, 4H), 7.25-7.04 (m, 1H), 4.07 (s, 2H), 3.61-3.50 (m, 4H), 1.42 (s, 9H).

Step 3) tert-butyl (3-oxomorpholino)(phenyl)carbamate

To a solution of tert-butyl 2-(2-(2-hydroxyethoxy)acetyl)-1-phenylhydrazine carboxylate (27.6 g, 89 mmol) and PPh₃ (35 g, 133.5 mmol) in dry THF (180 mL) at 0° C. under N₂ atmosphere was added a solution of DIAD in THF (120 mL) slowly via a syringe. The reaction was warmed up to r.t. and stirred overnight. The reaction mixture was filtered, the filtrate was added EtOAc (800 mL) and washed with H₂O (300 mL×2), followed with brine (300 mL). The organic phase was dried over anhydrous Na₂SO₄, filtered and concentrated in vacuo. The resulted residue was purified by a silica gel column chromatography (EtOAc/hex (v/v)=1/10-1/5) to afford the title compound as yellow oil (29.7 g, 100%).

LC-MS (ESI, pos, ion): 193.1 [M-100+H]⁺;

¹H NMR (400 MHz, DMSO-d₆) δ (ppm): 7.37 (dd, J=9.8, 3.8 Hz, 4H), 7.25-7.18 (m, 1H), 4.96-4.73 (m, 2H), 4.27 (q, J=16.5 Hz, 2H), 4.01-3.86 (m, 2H), 1.45 (s, 9H).

Step 4) 4-(phenylamino)morpholin-3-one

To a solution of tert-butyl (3-oxomorpholino)(phenyl)carbamate (29.7 g, 102 mmol) in EtOAc (50 mL) was added a saturated solution of HCl in EtOAc (350 mL). The mixture was stirred at r.t. for 2 h. The mixture was cooled to 0° C., and adjusted to pH=7-8 with a solution of NaOH (3 M aq), then the mixture was extracted with EtOAc (100 mL×3), the combined organic phase was dried over anhydrous Na₂SO₄ and concentrated in vacuo to afford the title compound as a yellow solid (12 g, 61%).

LC-MS (ESI, pos, ion): 193.1 [M+H]⁺;

¹H NMR (400 MHz, DMSO-d₆) δ (ppm): 8.24 (s, 1H), 7.19 (dd, J=8.4, 7.4 Hz, 2H), 6.77 (t, J=7.3 Hz, 1H), 6.69 (d, J=7.6 Hz, 2H), 4.20 (s, 2H), 4.01 (dd, J=14.3, 9.3 Hz, 2H), 3.60-3.48 (m, 2H).

Step 5) ethyl 3-oxo-3-((3-oxomorpholino)(phenyl)amino)propanoate

To a solution of 4-(phenylamino)morpholin-3-one (9 g, 46.8 mmol) and Na₂CO₃ (32.3 g, 305 mmol) in DCM (400 mL) was added ethyl malonoyl chloride (42.2 g, 281 mmol). The reaction was stirred at r.t. for 4 h. The reaction was filtered, the filtrate was added H₂O (500 mL). The water phase was extracted by EtOAc (200 mL×2), and the combined organic phase was dried over anhydrous Na₂SO₄ and concentrated in vacuo. The resulted residue was purified by a silica gel column chromatography (EtOAc/hex (v/v)=1/10-1/2) to give the title compound as yellow oil (15 g, 100%).

LC-MS (ESI, pos, ion): 307.2 [M+H]⁺;

¹H NMR (400 MHz, DMSO-d₆) δ (ppm): 7.54-7.53 (m, 2H), 7.45 (m, 3H), 4.38-4.32 (m, 2H), 4.18-4.10 (m, 2H), 3.96-3.84 (m, 2H), 3.72-3.61 (m, 2H), 3.30 (s, 2H), 1.27-1.23 (m, 3H).

Step 6) ethyl 2-oxo-1-phenyl-2,4,6,7-tetrahydro-1H-pyrazolo[5,1-c][1,4]oxazine-3-carboxylate A solution of ethyl 3-oxo-3-((3-oxomorpholino)(phenyl)amino)propanoate (15 g, 49 mmol) in DBU (16 mL) was warmed to 50° C. and stirred overnight. The mixture was cooled to r.t. and adjusted to pH=7 with saturated NaH₂PO₄ aqueous solution. Filtered, and the filtrate was extracted with EtOAc (50 mL×6). The combined organic phase was washed with brine (50 mL), dried over anhydrous Na₂SO₄ and concentrated in vacuo. The residue was purified by a silica gel column chromatography (EtOAc/hex (v/v)=7/10-8/10) to give the title compound as a white solid (13 g, 93%).

LC-MS (ESI, pos, ion): 289.1 [M+H]⁺;

¹H NMR (400 MHz, DMSO-d₆) δ (ppm): 7.55 (t, J=7.6 Hz, 2H), 7.46 (t, J=7.4 Hz, 1H), 7.42-7.36 (m, 2H), 4.98 (s, 2H), 4.15 (q, J=7.1 Hz, 2H), 4.07-4.02 (m, 2H), 3.61 (t, J=5.0 Hz, 2H), 1.23 (t, J=7.1 Hz, 3H).

Step 7) 2-oxo-1-phenyl-2,4,6,7-tetrahydro-1H-pyrazolo[5,1-c][1,4]oxazine-3-carboxylic acid To a solution of ethyl 2-oxo-1-phenyl-2,4,6,7-tetrahydro-1H-pyrazolo[5,1-c][1,4]oxazine-3-carboxylate (13 g, 45 mmol) in EtOH (70 mL) was added 1.6 N NaOH aqueous solution (70 mL). The reaction mixture was stirred at r.t. overnight. The mixture was concentrated in vacuo to remove EtOH, the water phase was washed with DCM (30 mL×3), and then the water phase was acidified with 2 N HCl aqueous solution to pH=2 and stirred at r.t. for 2 h, filtered, the collected solid mass was the title compound as a pale yellow solid (9.2 g, 79%).

LC-MS (ESI, pos, ion): 261.1 [M+H]⁺;

¹H NMR (400 MHz, CDCl₃) δ (ppm): 11.55 (s, 1H), 7.62-7.56 (m, 2H), 7.56-7.50 (m, 1H), 7.40 (dd, J=5.3, 3.3 Hz, 2H), 5.17 (s, 2H), 4.19-4.14 (m, 2H), 3.72-3.68 (m, 2H).

Step 8) N-(5-hydroxypyridin-2-yl)-2-oxo-1-phenyl-2,4,6,7-tetrahydro-1H-pyrazolo[5,1-c][1,4]oxazine-3-carboxamide To a solution of 6-aminopyridin-3-ol hydrochloride (3.2 g, 21.5 mmol) in DMF (25 mL) was added KOH (1.9 g, 33.8 mmol) at r.t., the reaction was stirred at r.t. for 30 min. and then to the solution was added 2-oxo-1-phenyl-2,4,6,7-tetrahydro-1H-pyrazolo [5,1-c][1,4]oxazine-3-carboxylic acid (3.5 g, 13.5 mmol), HOAT (367 mg, 2.7 mmol) and EDCI (5.2 g, 27.0 mmol) in portions. The reaction was allowed to warm up to 60° C. and stirred overnight. The reaction was cooled to r.t. and was added water (250 mL) and stirred for 2 h, filtered, the collected solid was dried in vacuo at 60° C. for 5 h to afford the title compound as a brown solid (2.65 g, 56%).

LC-MS (ESI, pos, ion): 353.2 [M+H]⁺;

¹H NMR (400 MHz, DMSO-d₆) δ (ppm): 10.48 (s, 1H), 9.63 (s, 1H), 8.03 (d, J=8.9 Hz, 1H), 7.84 (d, J=2.7 Hz, 1H), 7.60 (t, J=7.4 Hz, 3H), 7.52 (t, J=7.7 Hz, 4H), 7.20 (dd, J=8.9, 2.8 Hz, 1H), 5.11 (s, 2H), 4.09 (t, J=4.7 Hz, 2H), 3.68 (d, J=4.6 Hz, 2H).

Step 9) N-(5-((2-carbamoylpyridin-4-yl)oxy)pyridin-2-yl)-2-oxo-1-phenyl-2,4,6,7-tetrahydro-1H-pyrazolo[5,1-c][1,4]oxazine-3-carboxamide To a solution of 4-chloropicolinamide (1.07 g, 6.9 mmol) and N-(5-hydroxypyridin-2-yl)-2-oxo-1-phenyl-2,4,6,7-tetrahydro-1H-pyrazolo[5,1-c][1,4]oxazine-3-carboxamide (2.10 g, 6.0 mmol) in DMF (12 mL) was added t-BuOK (1.35 g, 12.0 mmol). The reaction was warmed up to 130° C. and stirred overnight. The reaction was cooled to r.t. and diluted with 120 mL of water, continued to stir at r.t.

overnight, filtered, the collected mass was the title compound as a brown solid (2.2 g, 78%).

LC-MS (ESI, pos, ion): 473.3 [M+H]$^+$;

$^1$H NMR (400 MHz, DMSO-d$_6$) δ (ppm): 10.86 (s, 1H), 8.54 (d, J=5.6 Hz, 1H), 8.33 (d, J=9.0 Hz, 1H), 8.29 (d, J=2.8 Hz, 1H), 8.14 (s, 1H), 7.78 (dd, J=9.0, 2.9 Hz, 1H), 7.72 (s, 1H), 7.60 (d, J=7.3 Hz, 2H), 7.54 (t, J=6.0 Hz, 3H), 7.44 (d, J=2.6 Hz, 1H), 7.22 (dd, J=5.6, 2.6 Hz, 1H), 5.13 (s, 2H), 4.10 (t, J=5.0 Hz, 2H), 3.70 (t, J=4.9 Hz, 2H).

Step 10) N-(5-((2-aminopyridin-4-yl)oxy)pyridin-2-yl)-2-oxo-1-phenyl-2,4,6,7-tetrahydro-1H-pyrazolo[5,1-c][1,4]oxazine-3-carboxamide To a solution of N-(5-((2-carbamoylpyridin-4-yl)oxy)pyridin-2-yl)-2-oxo-1-phenyl-2,4,6,7-tetrahydro-1H-pyrazolo[5,1-c][1,4]oxazine-3-carboxamide (2.1 g, 4.4 mmol) in a mixture solvent of EtOH (35 mL), MeCN (35 mL) and water (17 mL) at 0° C. was added PhI(OAc)$_2$ (1.8 g, 5.6 mmol). The mixture was stirred at 0° C. for 30 min, and then allowed to warm up to r.t. and stirred overnight. The reaction was filtered, the solid was washed with EtOAc (15 mL×2), the filtrate was concentrated in vacuo, and the residue was purified by a column chromatography on silica gel (100% DCM to 1% MeOH/DCM) to afford the title compound as a yellow solid (900 mg, 46%).

LC-MS (ESI, pos, ion): 445.1 [M+H]$^+$;

Q-TOF (ESI, pos, ion): 445.1621 [M+H]$^+$;

$^1$H NMR (600 MHz, CDCl$_3$) δ (ppm): 10.82 (s, 1H), 8.29 (d, J=9.0 Hz, 1H), 8.16 (d, J=2.8 Hz, 1H), 7.95 (d, J=5.7 Hz, 1H), 7.57 (t, J=7.8 Hz, 2H), 7.49 (t, J=7.5 Hz, 1H), 7.46-7.44 (m, 1H), 7.42 (d, J=9.0 Hz, 2H), 6.32-6.30 (m, 1H), 5.96 (s, 1H), 5.28 (s, 2H), 4.53 (s, 2H), 4.19-4.16 (m, 2H), 3.69 (t, J=5.0 Hz, 2H).

Example 11

N-(5-((2-(cyclopropanecarboxamido)pyridin-4-yl)oxy)pyridin-2-yl)-2-oxo-1-phenyl-2,4,6,7-tetrahydro-1H-pyrazolo[5,1-c][1,4]oxazine-3-carboxamide

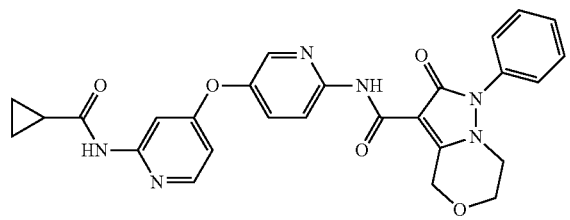 [SMILES: O=C(Nc1ccc(Oc2ccnc(NC(=O)C3CC3)c2)cn1)c1c2n(n(-c3ccccc3)c1=O)CCOC2]

To a solution of N-(5-((2-aminopyridin-4-yl)oxy)pyridin-2-yl)-2-oxo-1-phenyl-2,4,6,7-tetrahydro-1H-pyrazolo[5,1-c][1,4]oxazine-3-carboxamide (150 mg, 0.34 mmol) in a mixture solvent of MeCN (2 mL) and pyridine (1.2 mL) at r.t. was added a solution of cyclopropanecarbonyl chloride (106 mg, 1.01 mmol) and DMAP (123 mg, 1.01 mmol) in MeCN (1.2 mL). The reaction mixture was allowed to warm up to 60° C. and stirred overnight. The reaction was cooled to r.t., then diluted with DCM (15 mL), washed with water (10 mL×3), followed with brine (10 mL), dried over anhydrous Na$_2$SO$_4$ and filtered, the filtrate was concentrated in vacuo, and the residue was recrystallized in a mixture solution of DCM/EtOAc at the ratio of 1/1 (6 mL) to afford the title compound as a pale solid (125 mg, 72%).

LC-MS (ESI, pos, ion): 513.0 [M+H]$^+$;

Q-TOF (ESI, pos, ion): 513.1873 [M+H]$^+$;

$^1$H NMR (400 MHz, CDCl$_3$) δ (ppm): 10.81 (s, 1H), 8.31 (d, J=8.9 Hz, 1H), 8.17 (d, J=2.8 Hz, 2H), 8.13 (d, J=5.8 Hz, 1H), 7.84 (d, J=2.2 Hz, 1H), 7.57 (t, J=7.6 Hz, 2H), 7.49 (d, J=7.4 Hz, 1H), 7.46-7.41 (m, 3H), 6.57 (dd, J=5.7, 2.3 Hz, 1H), 5.28 (s, 2H), 4.19-4.14 (m, 2H), 3.69 (t, J=5.0 Hz, 2H), 1.56-1.50 (m, 1H), 1.28 (t, J=7.1 Hz, 2H), 1.12-1.07 (m, 2H).

Example 12

N-(5-((2-acetamidopyridin-4-yl)oxy)pyridin-2-yl)-2-oxo-1-phenyl-2,4,6,7-tetrahydro-1H-pyrazolo[5,1-c][1,4]oxazine-3-carboxamide

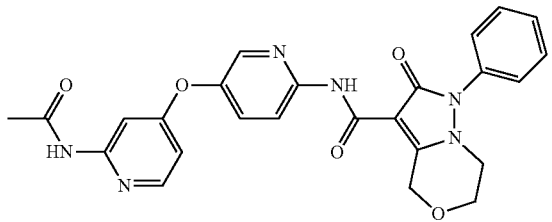 [SMILES: CC(=O)Nc1cc(Oc2ccc(NC(=O)c3c4n(n(-c5ccccc5)c3=O)CCOC4)nc2)ccn1]

To a solution of N-(5-((2-aminopyridin-4-yl)oxy)pyridin-2-yl)-2-oxo-1-phenyl-2,4,6,7-tetrahydro-1H-pyrazolo[5,1-c][1,4]oxazine-3-carboxamide (100 mg, 0.23 mmol) in Ac$_2$O (1 mL) was added Et$_3$N (139 mg, 1.38 mmol). The suspension was warmed up to 30° C. and stirred overnight. The reaction was cooled down to r.t. and concentrated in vacuo, the residue was recrystallized in a mixture solution of DCM/EtOAc/hex at the ratio of 2/2/1 (5 mL) to afford the title compound as a pale solid (55 mg, 50%).

LC-MS (ESI, pos, ion): 487.0 [M+H]$^+$;

Q-TOF (ESI, pos, ion): 487.1730 [M+H]$^+$;

$^1$H NMR (600 MHz, CDCl$_3$) δ (ppm): 10.82 (s, 1H), 8.32 (d, J=9.0 Hz, 1H), 8.17 (d, J=2.6 Hz, 1H), 8.12 (s, 1H), 8.03 (s, 1H), 7.88 (s, 1H), 7.57 (t, J=7.8 Hz, 2H), 7.50-7.45 (m, 2H), 7.42 (d, J=7.5 Hz, 2H), 6.56 (d, J=3.8 Hz, 1H), 5.28 (s, 2H), 4.19-4.15 (m, 2H), 3.69 (t, J=4.9 Hz, 2H), 2.20 (s, 3H).

Example 13

N-(5-((2-aminopyridin-4-yl)oxy)pyridin-2-yl)-2-oxo-1-phenyl-2,4,5,6-tetrahydro-1H-pyrrolo[1,2-b]pyrazole-3-carboxamide

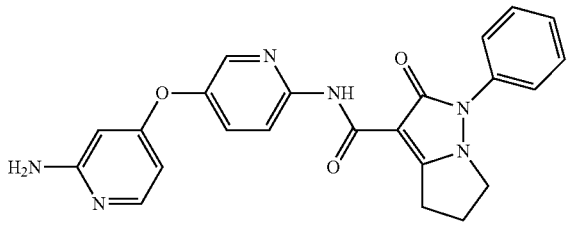 [SMILES: Nc1cc(Oc2ccc(NC(=O)c3c4n(n(-c5ccccc5)c3=O)CCC4)nc2)ccn1]

Step 1) N-(5-hydroxypyridin-2-yl)-2-oxo-1-phenyl-2,4,5,6-tetrahydro-1H-pyrrolo[1,2-b]pyrazole-3-carboxamide To a solution of 6-aminopyridin-3-ol hydrochloride (2.02 g, 13.8 mmol) in DMF (19 mL) was added TEA (2.18 g, 21.5 mmol) at r.t., the reaction was stirred at r.t. for 30 min. and then to the solution was added 2-oxo-1-phenyl-2,4,5,6-tetrahydro-1H-pyrrolo[1,2-b]pyrazole-3-carboxylic acid (2.1 g, 8.6 mmol), HOAT (293 mg, 2.15 mmol) and EDCI (2.06 g, 10.75 mmol) in portions. The reaction was allowed to warm up to 60° C. and stirred overnight. The reaction was cooled down to r.t. and diluted with water (190 mL) and stirred for 4 h, filtered and the solid was washed with water (20 mL×2), dried in vacuo at 60° C. for 4 h to afford the title compound as a brown solid (1.61 g, 56%).

LC-MS (ESI, pos, ion): 337.1 [M+H]+;

$^1$H NMR (600 MHz, DMSO-$d_6$) δ (ppm): 10.34 (s, 1H), 9.65 (s, 1H), 8.05 (d, J=8.9 Hz, 1H), 7.84 (d, J=2.8 Hz, 1H), 7.56 (t, J=7.9 Hz, 2H), 7.52-7.49 (m, 2H), 7.41 (t, J=7.3 Hz, 1H), 7.21 (dd, J=8.9, 2.9 Hz, 1H), 3.79 (t, J=6.9 Hz, 2H), 3.16 (t, J=7.4 Hz, 2H), 2.44-2.39 (m, 2H).

Step 2) N-(5-((2-carbamoylpyridin-4-yl)oxy)pyridin-2-yl)-2-oxo-1-phenyl-2,4,5,6-tetrahydro-1H-pyrrolo[1,2-b]pyrazole-3-carboxamide To a solution of 4-chloropicolinamide (862 mg, 5.5 mmol) and N-(5-hydroxypyridin-2-yl)-2-oxo-1-phenyl-2,4,5,6-tetrahydro-1H-pyrrolo[1,2-b]pyrazole-3-carboxamide (1.61 g, 4.8 mmol) in DMF (10 mL) was added t-BuOK (1.08 g, 9.6 mmol). The reaction was allowed to warm up to 130° C. and stirred overnight. The reaction was cooled to r.t. and diluted with 100 mL of water, continued to stir at r.t. overnight, filtered, the collected mass was dried in vacuo at 60° C. for 4 h to afford the title compound as a brown solid (1.7 g, 79%).

LC-MS (ESI, pos, ion): 457.3 [M+H]+;

$^1$H NMR (400 MHz, CDCl$_3$) δ (ppm): 10.76 (s, 1H), 8.45 (d, J=5.6 Hz, 1H), 8.41 (d, J=9.0 Hz, 1H), 8.19 (d, J=2.8 Hz, 1H), 7.84 (s, 1H), 7.77 (d, J=2.5 Hz, 1H), 7.52 (d, J=7.4 Hz, 2H), 7.46 (d, J=6.8 Hz, 3H), 7.39 (t, J=7.3 Hz, 1H), 7.00 (dd, J=5.6, 2.6 Hz, 1H), 5.57 (s, 1H), 3.76 (t, J=6.9 Hz, 2H), 3.35 (t, J=7.4 Hz, 2H), 2.56 (p, J=7.0 Hz, 2H).

Step 3) N-(5-((2-aminopyridin-4-yl)oxy)pyridin-2-yl)-2-oxo-1-phenyl-2,4,5,6-tetrahydro-1H-pyrrolo[1,2-b]pyrazole-3-carboxamide To a solution of N-(5-((2-carbamoylpyridin-4-yl)oxy)pyridin-2-yl)-2-oxo-1-phenyl-2,4,5,6-tetrahydro-1H-pyrrolo[1,2-b]pyrazole-3-carboxamide (1.72 g, 3.8 mmol) in a mixture solvent of EtOAc (28 mL), CH$_3$CN (28 mL) and water (14 mL) at 0° C. was added PhI(OAc)$_2$ (1.52 g, 4.7 mmol). The reaction mixture was stirred at 0° C. for 30 min and then removed to r.t. and stirred overnight. The reaction was filtered, the solid mass was washed with EtOAc (20 mL) twice, the filtrate was concentrated in vacuo, and the residue was purified by a column chromatography on a silica gel (DCM to DCM/MeOH=100/1) to afford the title compound as a pale yellow solid (450 mg, 28%).

LC-MS (ESI, pos, ion): 429.3 [M+H]+;

Q-TOF (ESI, pos, ion): 429.1678 [M+H]+;

$^1$H NMR (600 MHz, CDCl$_3$) δ (ppm): 10.71 (s, 1H), 8.34 (d, J=9.0 Hz, 1H), 8.16 (d, J=2.8 Hz, 1H), 7.95 (d, J=5.9 Hz, 1H), 7.52 (t, J=7.9 Hz, 2H), 7.46-7.41 (m, 3H), 7.38 (t, J=7.4 Hz, 1H), 6.30 (dd, J=5.9, 2.2 Hz, 1H), 5.96 (d, J=2.1 Hz, 1H), 4.53 (s, 2H), 3.75 (t, J=6.9 Hz, 2H), 3.33 (t, J=7.4 Hz, 2H), 2.55 (p, J=7.1 Hz, 2H).

Example 14

N-(5-((2-(cyclopropanecarboxamido)pyridin-4-yl)oxy)pyridin-2-yl)-2-oxo-1-phenyl-2,4,5,6-tetrahydro-1H-pyrrolo[1,2-b]pyrazole-3-carboxamide

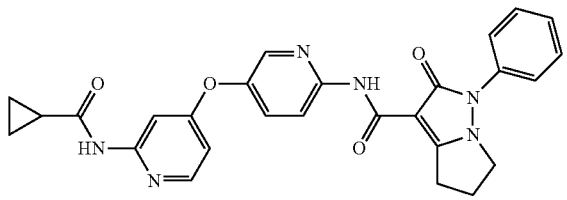 [SMILES: O=C(Nc1ccc(Oc2ccnc(NC(=O)C3CC3)c2)cn1)c1c2n(n(-c3ccccc3)c1=O)CCC2]

To a solution of N-(5-((2-aminopyridin-4-yl)oxy)pyridin-2-yl)-2-oxo-1-phenyl-2,4,5,6-tetrahydro-1H-pyrrolo[1,2-b]pyrazole-3-carboxamide (150 mg, 0.35 mmol) and pyridine (1.3 mL) in CH$_3$CN (2 mL) was added a solution of DMAP (128 mg, 1.05 mmol) and cyclopropanecarbonyl chloride (110 mg, 1.05 mmol) in CH$_3$CN (1.3 mL) at r.t. The reaction mixture was allowed to warm up to 60° C. and stirred overnight. The reaction was cooled down to r.t., and was diluted with 20 mL of DCM and 5 mL of water, the water phase was extracted with DCM (10 mL), the combined organic phase was washed with brine (10 mL), dried over Na$_2$SO$_4$ and filtered, the filtrate was concentrated in vacuo, and the residue was added 5 mL of EtOAc and 5 mL of water then stirred for 4 h, filtered, the collected solid mass was dried in vacuo at 60° C. for 4 h to afford the title compound as a pale yellow solid (120 mg, 61%).

LC-MS (ESI, pos, ion): 497.0 [M+H]+;

Q-TOF (ESI, pos, ion): 497.1915 [M+H]+;

$^1$H NMR (600 MHz, CDCl$_3$) δ (ppm): 10.69 (s, 1H), 8.35 (d, J=8.8 Hz, 2H), 8.15 (d, J=2.7 Hz, 1H), 8.11 (d, J=5.8 Hz, 1H), 7.83 (d, J=1.6 Hz, 1H), 7.50 (t, J=7.8 Hz, 2H), 7.45-7.41 (m, 3H), 7.36 (t, J=7.4 Hz, 1H), 6.55 (dd, J=5.8, 2.3 Hz, 1H), 3.73 (t, J=6.9 Hz, 2H), 3.31 (t, J=7.4 Hz, 2H), 2.53 (p, J=7.1 Hz, 2H), 1.50-1.54 (m, 1H), 1.06-1.09 (m, 2H), 0.86-0.88 (m, 2H).

$^{13}$C NMR (150 MHz, CDCl$_3$) δ (ppm): 172.20, 166.50, 165.94, 162.63, 160.97, 153.22, 149.18, 146.61, 141.07, 134.80, 130.25, 129.46, 127.35, 123.06, 114.79, 108.05, 101.81, 98.64, 49.77, 25.72, 22.14, 15.92, 8.39.

Example 15

N-(5-((2-acetamidopyridin-4-yl)oxy)pyridin-2-yl)-2-oxo-1-phenyl-2,4,5,6-tetrahydro-1H-pyrrolo[1,2-b]pyrazole-3-carboxamide

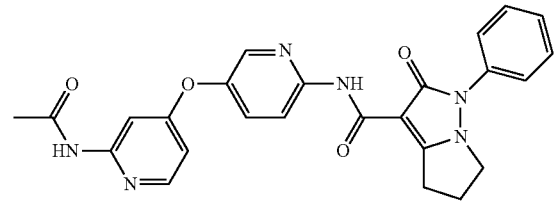 [SMILES: CC(=O)Nc1cc(Oc2ccc(NC(=O)c3c4n(n(-c5ccccc5)c3=O)CCC4)nc2)ccn1]

To a solution of N-(5-((2-aminopyridin-4-yl)oxy)pyridin-2-yl)-2-oxo-1-phenyl-2,4,5,6-tetrahydro-1H-pyrrolo[1,2-b]pyrazole-3-carboxamide (100 mg, 0.23 mmol) in Ac$_2$O (1 mL) was added Et$_3$N (141 mg, 1.40 mmol). The suspension was warmed up to 30° C. and stirred overnight. The reaction was cooled down to r.t. and 4 mL of water and 4 mL of EtOAc was added, the mixture was continued to stir at r.t. for 2 h, filtered, the collected solid was washed with EtOAc (2 mL), then dried in vacuo at 60° C. for 4 h to afford the title compound as a pale solid (60 mg, 55%).

LC-MS (ESI, pos, ion): 471.3 [M+H]⁺;
Q-TOF (ESI, pos, ion): 471.1776 [M+H]⁺;
¹H NMR (600 MHz, CDCl₃) δ (ppm): 10.70 (s, 1H), 8.36 (d, J=9.0 Hz, 1H), 8.16 (d, J=2.8 Hz, 1H), 8.10 (d, J=5.8 Hz, 1H), 8.05 (s, 1H), 7.86 (s, 1H), 7.51 (t, J=7.9 Hz, 2H), 7.46-7.42 (m, 3H), 7.36 (t, J=7.4 Hz, 1H), 6.54 (dd, J=5.8, 2.3 Hz, 1H), 3.73 (t, J=6.9 Hz, 2H), 3.32 (t, J=7.4 Hz, 2H), 2.53 (p, J=7.1 Hz, 2H), 2.18 (s, 3H).

Example 16

N-(4-((2-aminopyridin-4-yl)oxy)-3-fluorophenyl)-2-oxo-1-phenyl-2,4,6,7-tetrahydro-1H-pyrazolo[5,1-c][1,4]oxazine-3-carboxamide

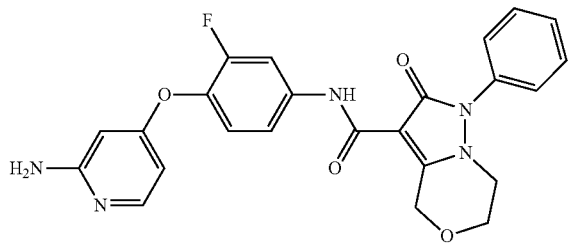 [SMILES: Nc1cc(Oc2ccc(NC(=O)c3c4n(n(-c5ccccc5)c3=O)CCOC4)cc2F)ccn1]

Step 1) N-(4-((2-carbamoylpyridin-4-yl)oxy)-3-fluorophenyl)-2-oxo-1-phenyl-2,4,6,7-tetrahydro-1H-pyrazolo[5,1-c][1,4]oxazine-3-carboxamide To a solution of 2-oxo-1-phenyl-2,4,6,7-tetrahydro-1H-pyrazolo[5,1-c][1,4]oxazine-3-carboxylic acid (500 mg, 1.92 mmol), 4-(4-amino-2-fluorophenoxy)picolinamide (465.6 mg, 1.89 mmol) and HOAT (51.4 mg, 0.38 mmol) in DCM (15 mL) was added EDCI (555 mg, 2.89 mmol). The reaction was allowed to warm up to 50° C. and stirred overnight. The reaction was cooled down to r.t. and concentrated in vacuo, the residue was purified by a column chromatography on silica gel (DCM/MeOH (v/v)=100/1-50/1) to afford the title compound as a white solid (450 mg, 48.7%).

LC-MS (ESI, pos, ion): 490.3 [M+H]⁺;
¹H NMR (400 MHz, DMSO-d₆) δ (ppm): 10.55 (s, 1H), 8.54 (d, J=5.6 Hz, 1H), 8.13 (s, 1H), 8.01-7.94 (m, 1H), 7.73 (s, 1H), 7.65-7.57 (m, 2H), 7.54 (dd, J=7.1, 4.9 Hz, 3H), 7.44-7.35 (m, 3H), 7.22 (dd, J=5.6, 2.7 Hz, 1H), 5.12 (s, 2H), 4.10 (q, J=5.3 Hz, 2H), 3.71 (t, J=4.9 Hz, 2H).

Step 2) N-(4-((2-aminopyridin-4-yl)oxy)-3-fluorophenyl)-2-oxo-1-phenyl-2,4,6,7-tetrahydro-1H-pyrazolo[5,1-c][1,4]oxazine-3-carboxamide N-(4-((2-carbamoylpyridin-4-yl)oxy)-3-fluorophenyl)-2-oxo-1-phenyl-2,4, 6,7-tetrahydro-1H-pyrazolo[5,1-c][1,4]oxazine-3-carboxamide (450 mg, 0.92 mmol) in a mixture of EtOAc (7 mL), MeCN (7 mL) and H₂O (3.5 mL) at 0° C. was added PhI(OAc)₂ (370.4 mg, 1.15 mmol). The mixture was stirred at 0° C. for 0.5 h. Then the reaction was warmed up to r.t. and stirred overnight. The mixture was concentrated in vacuo and the residue was purified by a column chromatography on silica gel (DCM/MeOH (v/v)=100/1-50/1) to afford the title compound as a yellow solid (280 mg, 66%).

LC-MS (ESI, pos, ion): 462.0 [M+H]⁺;
Q-TOF (ESI, pos, ion): 462.1578 [M+H]⁺;
¹H NMR (400 MHz, DMSO-d₆) δ (ppm): 10.55 (s, 1H), 8.54 (d, J=5.6 Hz, 1H), 8.13 (s, 1H), 8.01-7.94 (m, 1H), 7.73 (s, 1H), 7.65-7.57 (m, 2H), 7.54 (dd, J=7.1, 4.9 Hz, 3H), 7.44-7.35 (m, 3H), 7.22 (dd, J=5.6, 2.7 Hz, 1H), 5.12 (s, 2H), 4.10 (q, J=5.3 Hz, 2H), 3.71 (t, J=4.9 Hz, 2H).

Example 17

N-(4-((2-(cyclopropanecarboxamido)pyridin-4-yl)oxy)-3-fluorophenyl)-2-oxo-1-phenyl-2,4,6,7-tetrahydro-1H-pyrazolo[5,1-c][1,4]oxazine-3-carboxamide

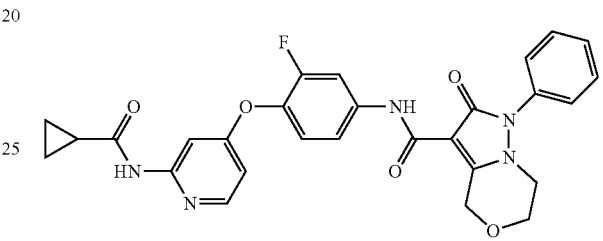

To a solution of N-(4-((2-aminopyridin-4-yl)oxy)-3-fluorophenyl)-2-oxo-1-phenyl-2,4,6,7-tetrahydro-1H-pyrazolo[5,1-c][1,4]oxazine-3-carboxamide (170 mg, 0.37 mmol) and pyridine (1.2 mL) in MeCN (2 mL) was added a solution of cyclopropanecarbonyl chloride (116 mg, 1.1 mmol) and DMAP (134 mg, 1.1 mmol) in MeCN (1.2 mL). The reaction mixture was allowed to warmed up to 60° C. and stirred overnight. The reaction was cooled down to r.t. and concentrated in vacuo, the residue was purified by a column chromatography on silica gel (EtOAc/PE (v/v)=5/2-1/1.5) to afford the title compound as a white solid (100 mg, 51.3%).

LC-MS (ESI, pos, ion): 530.0 [M+H]⁺;
Q-TOF (ESI, pos, ion): 530.1837 [M+H]⁺;
¹H NMR (400 MHz, DMSO-d₆) δ (ppm): 10.86 (s, 1H), 10.52 (s, 1H), 8.20 (d, J=5.7 Hz, 1H), 8.01-7.87 (m, 1H), 7.67-7.56 (m, 3H), 7.54 (t, J=6.3 Hz, 3H), 7.38-7.27 (m, 2H), 6.72 (dd, J=5.7, 2.4 Hz, 1H), 5.12 (s, 2H), 4.09 (dt, J=17.8, 8.8 Hz, 2H), 3.71 (t, J=4.9 Hz, 2H), 2.04-1.90 (m, 1H), 1.32-1.14 (m, 2H), 0.81-0.72 (m, 2H).

Example 18

N-(4-((2-aminopyridin-4-yl)oxy)phenyl)-2-oxo-1-phenyl-2,4,6,7-tetrahydro-1H-pyrazolo[5,1-c][1,4]oxazine-3-carboxamide

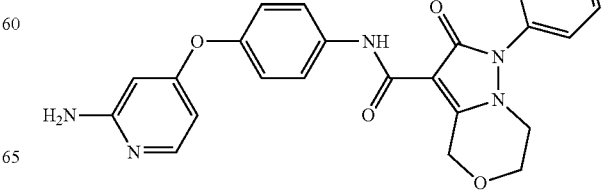

Step 1) N-(4-((2-carbamoylpyridin-4-yl)oxy)phenyl)-2-oxo-1-phenyl-2,4,6,7-tetrahydro-1H-pyrazolo[5,1-c][1,4]oxazine-3-carboxamide To a solution of 2-oxo-1-phenyl-2,4,6,7-tetrahydro-1H-pyrazolo[5,1-c][1,4]oxazine-3-carboxylic acid (500 mg, 1.92 mmol), 4-(4-aminophenoxy)picolinamide (431 mg, 1.89 mmol) and HOAT (51.4 mg, 0.38 mmol) in DCM (15 mL) was added EDCI (555 mg, 2.89 mmol). The reaction was allowed to warmed up to 50° C. and stirred overnight. The reaction was cooled down to r.t. and concentrated in vacuo, the residue was purified by a column chromatography on silica gel (DCM/MeOH (v/v)=100/1-50/1) to afford the title compound as a white solid (680 mg, 74.15%).

LC-MS (ESI, pos, ion): 472.3 [M+H]$^+$;

$^1$H NMR (400 MHz, DMSO-d$_6$) δ (ppm): 10.43 (s, 1H), 8.51 (d, J=5.6 Hz, 1H), 8.11 (s, 1H), 7.72 (t, J=11.1 Hz, 3H), 7.64-7.57 (m, 2H), 7.56-7.48 (m, 3H), 7.40 (d, J=2.5 Hz, 1H), 7.23-7.14 (m, 3H), 5.13 (s, 2H), 4.09 (dd, J=10.9, 5.5 Hz, 2H), 3.70 (t, J=4.8 Hz, 2H).

Step 2) N-(4-((2-aminopyridin-4-yl)oxy)phenyl)-2-oxo-1-phenyl-2,4,6,7-tetrahydro-1H-pyrazolo[5,1-c][1,4]oxazine-3-carboxamide To a solution of N-(4-((2-carbamoylpyridin-4-yl)oxy)phenyl)-2-oxo-1-phenyl-2,4,6,7-tetrahydro-1H-pyrazolo[5,1-c][1,4]oxazine-3-carboxamide (650 mg, 1.38 mmol) in a mixture of EtOAc (16 mL), MeCN (16 mL) and H$_2$O (8 mL) at 0° C. was added PhI(OAc)$_2$ (666.76 mg, 2.07 mmol). The mixture was stirred at 0° C. for 0.5 h. Then the reaction was warmed up to r.t. and stirred overnight. The mixture was concentrated in vacuo and the residue was purified by a column chromatography on silica gel (DCM/MeOH (v/v) =100/1-50/1) to afford the title compound as a yellow solid (561 mg, 91.8%).

LC-MS (ESI, pos, ion): 444.3 [M+H]$^+$;
Q-TOF (ESI, pos, ion): 444.1861 [M+H]$^+$;

$^1$H NMR (400 MHz, DMSO-d$_6$) δ (ppm): 10.37 (s, 1H), 7.79 (d, J=5.8 Hz, 1H), 7.67 (d, J=8.8 Hz, 2H), 7.64-7.57 (m, 2H), 7.53 (t, J=6.3 Hz, 3H), 7.10 (d, J=8.8 Hz, 2H), 6.14 (dd, J=5.8, 2.1 Hz, 1H), 5.92 (s, 2H), 5.82 (d, J=1.9 Hz, 1H), 5.12 (s, 2H), 4.10 (t, J=4.8 Hz, 2H), 3.69 (t, J=4.8 Hz, 2H).

Example 19

N-(4-((2-(cyclopropanecarboxamido)pyridin-4-yl)oxy)phenyl)-2-oxo-1-phenyl-2,4,6,7-tetrahydro-1H-pyrazolo[5,1-c][1,4]oxazine-3-carboxamide

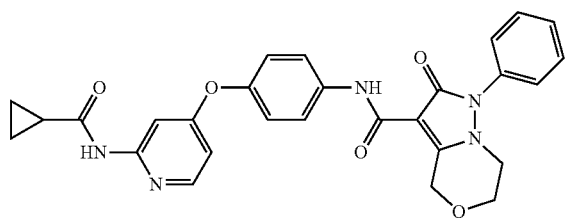 [SMILES: O=C(Nc1ccc(Oc2ccnc(NC(=O)C3CC3)c2)cc1)c1c2n(n(-c3ccccc3)c1=O)CCOC2]

To a solution of N-(4-((2-aminopyridin-4-yl)oxy)-3-phenyl)-2-oxo-1-phenyl-2,4,6,7-tetrahydro-1H-pyrazolo[5,1-c][1,4]oxazine-3-carboxamide (222 mg, 0.5 mmol) and pyridine (1.6 mL) in MeCN (2.7 mL) was added a solution of cyclopropanecarbonyl chloride (157 mg, 1.5 mmol) and DMAP (183 mg, 1.5 mmol) in MeCN (1.6 mL). The reaction mixture was allowed to warmed up to 60° C. and stirred overnight. The reaction was cooled down to r.t. and concentrated in vacuo, the residue was purified by a column chromatography on silica gel (DCM/MeOH (v/v)=100/0-100/1) to afford the title compound as a white solid (100 mg, 39.1%).

LC-MS (ESI, pos, ion): 512.3 [M+H]$^+$;
Q-TOF (ESI, pos, ion): 512.1884 [M+H]$^+$;

$^1$H NMR (600 MHz, DMSO-d$_6$) δ (ppm): 10.81 (s, 1H), 10.40 (s, 1H), 8.18 (d, J=5.7 Hz, 1H), 7.72-7.67 (m, 2H), 7.64 (d, J=2.3 Hz, 1H), 7.60 (dd, J=9.6, 5.9 Hz, 2H), 7.55-7.50 (m, 3H), 7.16-7.10 (m, 2H), 6.67 (dd, J=5.7, 2.4 Hz, 1H), 5.12 (s, 2H), 4.10 (t, J=5.0 Hz, 2H), 3.70 (t, J=5.0 Hz, 2H), 1.98 (m, 1H), 1.27-1.23 (m, 2H), 0.77 (m, 2H).

Example 20

N-(4-((2-acetamidopyridin-4-yl)oxy)phenyl)-2-oxo-1-phenyl-2,4,6,7-tetrahydro-1H-pyrazolo[5,1-c][1,4]oxazine-3-carboxamide

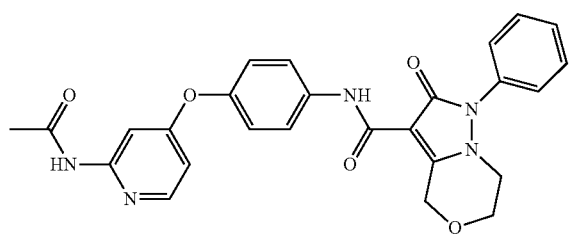 [SMILES: CC(=O)Nc1cc(Oc2ccc(NC(=O)c3c4n(n(-c5ccccc5)c3=O)CCOC4)cc2)ccn1]

To a solution of N-(4-((2-aminopyridin-4-yl)oxy)-phenyl)-2-oxo-1-phenyl-2,4,6,7-tetrahydro-1H-pyrazolo[5,1-c][1,4]oxazine-3-carboxamide (1.2 g, 2.7 mmol) in acetyl acetate (20 mL) was added Et$_3$N (1.63 g, 16.1 mmol). The reaction mixture was allowed to warm up to 50° C. and stirred overnight. The reaction was cooled down to r.t. and concentrated in vacuo, the residue was added a solution of DCM/EtOAc/PE=2/2/1 (30 mL) and stirred for 2 h. The mixture was filtered to afford the title compound as a white solid (800 mg, 60%).

LC-MS (ESI, pos, ion): 486.3 [M+H]$^+$;

$^1$H NMR (400 MHz, DMSO-d$_6$) δ (ppm): 10.51 (s, 1H), 10.40 (s, 1H), 8.17 (d, J=5.7 Hz, 1H), 7.69 (d, J=8.9 Hz, 2H), 7.65 (d, J=1.7 Hz, 1H), 7.63-7.57 (m, 2H), 7.56-7.49 (m, 3H), 7.14 (d, J=8.9 Hz, 2H), 6.64 (dd, J=5.7, 2.3 Hz, 1H), 5.12 (s, 2H), 4.10 (t, J=4.9 Hz, 2H), 3.69 (t, J=4.8 Hz, 2H), 2.04 (s, 3H).

Example 21

N-(5-((2-amino-3-chloropyridin-4-yl)oxy)pyridin-2-yl)-2-oxo-1-phenyl-1,2,4,5,6,7-hexahydropyrazolo[1,5-a]pyridine-3-carboxamide

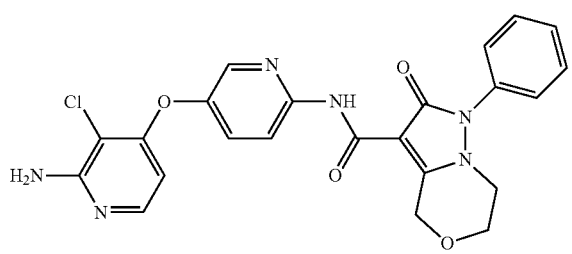 [SMILES: Nc1nccc(Oc2ccc(NC(=O)c3c4n(n(-c5ccccc5)c3=O)CCOC4)nc2)c1Cl]

Step 1) N-(5-((2-carbamoyl-3-chloropyridin-4-yl)oxy)pyridin-2-yl)-2-oxo-1-phenyl-1,2,4,5,6,7-hexahydropyrazolo[1,5-a]pyridine-3-carboxamide To a solution of 3,4-dichloropicolinamide (263 mg, 1.38 mmol) and N-(5-hydroxypyridin-2-yl)-2-oxo-1-phenyl-1,2,4,5,6,7-hexahydropyrazolo[1,5-a]pyridine-3-carboxamide (420 mg, 1.20 mmol) in DMF (2.4 mL) was added t-BuOK (269 mg, 2.40 mmol). The reaction was allowed to warm up to 130° C. and stirred overnight. The reaction was cooled down to r.t. and diluted with 24 mL of water, continued to stir at r.t. overnight, filtered, and the collected mass was dried in vacuo at 60° C. for 5 h to afford the title compound as a brown solid (489 mg, 81%).

LC-MS (ESI, pos, ion): 505.2 [M+H]$^+$;

$^1$H NMR (600 MHz, DMSO-d$_6$) δ (ppm): 11.13 (s, 1H), 8.35 (dd, J=7.5, 3.0 Hz, 2H), 8.27 (d, J=2.9 Hz, 1H), 8.04 (s, 1H), 7.75 (dd, J=9.0, 2.8 Hz, 2H), 7.60 (t, J=7.7 Hz, 2H), 7.53 (t, J=7.4 Hz, 1H), 7.49-7.46 (m, 2H), 6.93 (d, J=5.6 Hz, 1H), 3.58 (t, J=5.9 Hz, 2H), 3.22 (t, J=6.3 Hz, 2H), 2.00-1.97 (m, 2H), 1.85-1.80 (m, 2H).

Step 2) N-(5-((2-amino-3-chloropyridin-4-yl)oxy)pyridin-2-yl)-2-oxo-1-phenyl-1,2,4,5,6,7-hexahydropyrazolo[1,5-a]pyridine-3-carboxamide To a solution of N-(5-((2-carbamoyl-3-chloropyridin-4-yl)oxy)pyridin-2-yl)-2-oxo-1-phenyl-1,2,4,5,6,7-hexahydropyrazolo[1,5-a]pyridine-3-carboxamide (489 mg, 0.97 mmol) in a mixture solvent of EtOAc (7.2 mL), CH$_3$CN (7.2 mL) and H$_2$O (3.6 mL) at 0° C. was added PhI(OAc)$_2$ (390 mg, 1.21 mmol). The mixture was continued to stir at 0° C. for 30 min, then was allowed to warm up to r.t. and stirred overnight. The reaction was filtered, and the filtrate was concentrated in vacuo, the residue was purified by a column chromatography on silica gel (DCM to MeOH/DCM=1/100) to afford the title compound as a pale yellow solid (260 mg, 56%).

LC-MS (ESI, pos, ion): 476.9 [M+H]$^+$;
Q-TOF (ESI, pos, ion): 477.1391 [M+H]$^+$;

$^1$H NMR (600 MHz, CDCl$_3$) δ (ppm): 11.12 (s, 1H), 8.34 (d, J=9.0 Hz, 1H), 8.17 (d, J=2.7 Hz, 1H), 7.82 (d, J=5.7 Hz, 1H), 7.54 (t, J=7.7 Hz, 2H), 7.48-7.41 (m, 2H), 7.38 (d, J=7.5 Hz, 2H), 6.08 (d, J=5.7 Hz, 1H), 5.00 (s, 2H), 3.59 (t, J=5.9 Hz, 2H), 3.40 (t, J=6.4 Hz, 2H), 2.13-2.07 (m, 2H), 1.98-1.91 (m, 2H).

$^{13}$C NMR (150 MHz, CDCl$_3$) δ (ppm): 163.53, 161.81, 160.77, 156.67, 155.51, 149.52, 146.87, 146.60, 140.85, 133.00, 129.98, 129.64, 128.80, 126.56, 114.68, 103.09, 102.85, 98.21, 47.42, 23.77, 22.60, 19.72.

Example 22

N-(4-((2-amino-3-chloropyridin-4-yl)oxy)phenyl)-2-oxo-1-phenyl-1,2,4,5,6,7-hexahydropyrazolo[1,5-a]pyridine-3-carboxamide

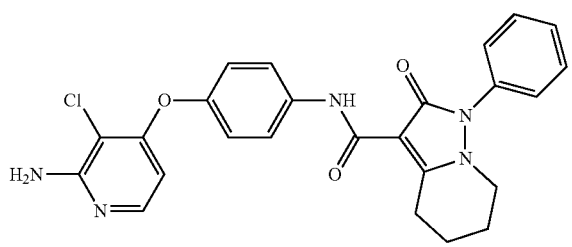 [SMILES: Nc1nccc(Oc2ccc(NC(=O)c3c4n(n(-c5ccccc5)c3=O)CCCC4)cc2)c1Cl]

Step 1) 3,4-dichloropicolinamide

To a solution of 2,2,6,6-tetramethylpiperidine (12.4 mL, 74.4 mmol) in diethylether (100 mL) at 0° C. was added n-BuLi in hexane (2.5 M, 46 mL, 115 mmol) via a syringe over 15 min. The resulting solution was stirred at 0° C. for 0.5 h and at −78° C. for 0.5 h. To this mixture was added a mixture of 3,4-dichloropyridine (10.00 g, 67.6 mmol) in diethylether (40 mL) via a syringe over 15 min. The resulting mixture was stirred at −78° C. for 2 h before the addition of isocyanatotrimethylsilane (94% pure, 13.4 mL, 101.4 mmol). After the addition, the cooling bath was removed and the reaction mixture was allowed to warm to room temperature for 2 h. The reaction mixture was quenched with acetic acid (13.52 g, 225.2 mmol) and 70 mL of water. The mixture was allowed to stir overnight, and the white solid that formed was collected through filtration and washed with water. The filtrate was extracted with EtOAc (50 mL×3). The combined organic phase was washed with brine and dried over anhydrous Na$_2$SO$_4$, then concentrated in vacuo. The residue was beaten by PE/EtOAc=2/1 (100 mL) to give a white solid. The two parts of solid was got together to give the title compound (6.95 g, 53.9%).

LC-MS (ESI, pos, ion): 191 [M+H]$^+$;

$^1$H NMR (400 MHz, CDCl$_3$) δ (ppm): 8.38 (d, J=5.0 Hz, 1H), 7.59 (d, J=5.0 Hz, 1H).

Step 2) 4-(4-aminophenoxy)-3-chloropicolinamide

To a solution of 4-aminophenol hydrochloride (436.8 mg, 3 mmol) in DMF (6 mL) was added t-BuOK (841 mg, 7.5 mmol) at 0° C. The mixture was stirred at 0° C. for 15 min before 3,4-dichloropicolinamide (570 mg, 3 mmol) was added. The reaction mixture was allowed to warm up to 80° C. and stirred overnight. The reaction mixture was concentrated in vacuo. The residue was added H$_2$O (10 mL) and filtered. The filter cake was washed with 2 mL of H$_2$O and dried in vacuo. The filtrate was extracted by EtOAc (10 mL×2). The organic phase was washed with brine dried over anhydrous Na$_2$SO$_4$ and concentrated in vacuo. The residue was beaten by PE/EtOAc (15 mL/5 mL) to give a yellow solid. Two parts of solid was collected together to give the title compound (510 mg, 64.3%).

LC-MS (ESI, pos, ion): 264.2 [M+H]$^+$;

$^1$H NMR (400 MHz, DMSO-d$_6$) δ (ppm): 8.28 (d, J=5.6 Hz, 1H), 7.97 (d, J=12.5 Hz, 1H), 7.70 (s, 1H), 6.87 (d, J=8.7 Hz, 2H), 6.67 (dd, J=12.5, 7.2 Hz, 3H), 5.21 (s, 2H).

Step 3) N-(4-((2-carboyl-3-chloropyridin-4-yl)oxy)phenyl)-2-oxo-1-phenyl-1,2,4,5,6,7-hexahydropyrazolo[1,5-a]pyridine-3-carboxamide To a solution of 2-oxo-1-phenyl-1,2,4,5,6,7-hexahydropyrazolo[1,5-a]pyridine-3-carboxylic acid (510 mg, 1.98 mmol), 4-(4-aminophenoxy)-3-chloropicolinamide (510 mg, 1.94 mmol) and HOAT (52 mg, 0.39 mmol) in DCM (15 mL) was added EDCI (558 mg, 2.91 mmol). The reaction was allowed to warm up to 50° C. and stirred overnight. The reaction was cooled down to r.t. and concentrated in vacuo. the residue was beaten by DCM/EtOAc/H$_2$O (20 mL/10 mL/10 mL) for 1 h. The mixture was filtered and the filter cake was dried in vacuo to afford the title compound as a white solid (539 mg, 55.3%).

LC-MS (ESI, pos, ion): 504.3 [M+H]$^+$;

$^1$H NMR (600 MHz, DMSO-d$_6$) δ (ppm): 10.66 (s, 1H), 7.76 (d, J=5.8 Hz, 1H), 7.66 (t, J=10.3 Hz, 2H), 7.58 (t, J=7.7 Hz, 2H), 7.51 (t, J=7.4 Hz, 1H), 7.46 (d, J=7.4 Hz, 2H), 7.11

(d, J=8.9 Hz, 2H), 6.48 (s, 2H), 5.98 (d, J=5.7 Hz, 1H), 3.57 (t, J=5.8 Hz, 2H), 3.21 (t, J=6.3 Hz, 2H), 1.98 (dd, J=7.6, 4.3 Hz, 2H), 1.85-1.77 (m, 2H).

Step 4) N-(4-((2-amino-3-chloropyridin-4-yl)oxy)phenyl)-2-oxo-1-phenyl-1,2,4,5,6,7-hexahydropyrazolo[1,5-a]pyridine-3-carboxamide N-(4-((2-carboyl-3-chloropyridin-4-yl)oxy)phenyl)-2-oxo-1-phenyl-1,2,4,5,6,7-hexahydropyrazolo[1,5-a]pyridine-3-carboxamide (539 mg, 1.03 mmol) in a mixture solvent of EtOAc (8 mL), MeCN (8 mL) and H₂O (4 mL) at 0° C. was added PhI(OAc)₂ (500 mg, 1.55 mmol). The mixture was stirred at 0° C. for 0.5 h. Then the reaction was warmed up to r.t. and stirred overnight. The mixture was filtered. The filtrate was concentrated in vacuo. The residue was beaten by PE/EtOAc (4 mL/4 mL) for 1 h. The mixture was filtered and the filter cake was dried in vacuo to afford the title compound as a yellow solid (254 mg, 51.9%).

LC-MS (ESI, pos, ion): 476.0 [M+H]$^+$;

Q-TOF (ESI, pos, ion): 476.1447 [M+H]$^+$;

$^1$H NMR (600 MHz, DMSO-$d_6$) δ (ppm): 10.66 (s, 1H), 7.76 (d, J=5.8 Hz, 1H), 7.66 (t, J=10.3 Hz, 2H), 7.58 (t, J=7.7 Hz, 2H), 7.51 (t, J=7.4 Hz, 1H), 7.46 (d, J=7.4 Hz, 2H), 7.11 (d, J=8.9 Hz, 2H), 6.48 (s, 2H), 5.98 (d, J=5.7 Hz, 1H), 3.57 (t, J=5.8 Hz, 2H), 3.21 (t, J=6.3 Hz, 2H), 1.98 (dd, J=7.6, 4.3 Hz, 2H), 1.85-1.77 (m, 2H).

Example 23

N-(4-((2-amino-3-chloropyridin-4-yl)oxy)-3-fluorophenyl)-2-oxo-1-phenyl-1,2,4,5,6,7-hexahydropyrazolo[1,5-a]pyridine-3-carboxamide

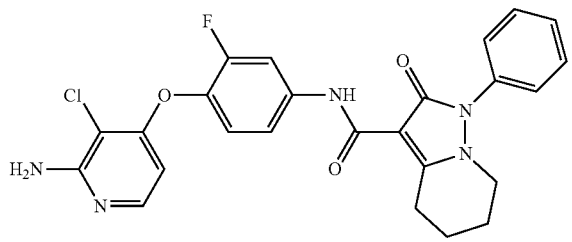 [SMILES: Nc1nccc(Oc2ccc(NC(=O)c3c4n(n(-c5ccccc5)c3=O)CCCC4)cc2F)c1Cl]

Step 1) 4-amino-2-fluorophenol

To a solution of 2-fluoro-4-nitrophenol (1.57 g, 10 mmol) in EtOH (50 mL) and H₂O (18 mL) was added Fe (2.24 g, 40 mmol) and NH₄Cl (4.24 g, 80 mmol). The reaction mixture was stirred at r.t. overnight. The mixture was filtered through a pad of celite. The filtrate was concentrated in vacuo. The residue was added H₂O (50 mL) and extracted by EtOAc (60 mL×2). The combined organic phase was washed with brine, dried over anhydrous Na₂SO₄ and concentrated in vacuo. The residue was beaten by PE/EtOAc (v/v, 10 mL/15 mL), filtered to give the title compound as a brown solid (700 mg, 55.1%).

LC-MS (ESI, pos, ion): 128.3 [M+H]$^+$;

$^1$H NMR (400 MHz, DMSO-$d_6$) δ (ppm): 8.56 (s, 1H), 6.62 (dd, J=10.0, 8.6 Hz, 1H), 6.34 (dd, J=13.4, 2.6 Hz, 1H), 6.24-6.15 (m, 1H), 4.66 (s, 2H).

Step 2) 4-(4-amino-2-fluorophenoxy)-3-chloropicolinamide

To a solution of 4-amino-2-fluorophenol (381 mg, 3 mmol) and 3,4-dichloropicolinamide (570 mg, 3 mmol) in DMF (4 mL) was added t-BuOK (404 mg, 3.6 mmol). The reaction mixture was allowed to warm up to 80° C. and stirred overnight. The mixture was added H₂O (15 mL) and filtered. The filter cake was washed with 2 mL of H₂O and dried in vacuo to give the title compound as a black solid (508 mg, 60.2%).

LC-MS (ESI, pos, ion): 282.0 [M+H]$^+$;

$^1$H NMR (400 MHz, DMSO-$d_6$) δ (ppm): 8.31 (d, J=5.6 Hz, 1H), 8.03 (s, 1H), 7.73 (s, 1H), 7.04 (t, J=9.0 Hz, 1H), 6.73 (d, J=5.5 Hz, 1H), 6.54 (dd, J=13.2, 2.4 Hz, 1H), 6.45 (dd, J=8.7, 2.0 Hz, 1H), 5.55 (s, 2H).

Step 3) N-(4-((2-carbamoyl-3-chloropyridin-4-yl)oxy)-3-fluorophenyl)-2-oxo-1-phenyl-1,2,4,5,6,7-hexahydropyrazolo[1,5-a]pyridine-3-carboxamide To a solution of 2-oxo-1-phenyl-1,2,4,5,6,7-hexahydropyrazolo[1,5-a]pyridine-3-carboxylic acid (476 mg, 1.84 mmol), 4-(4-amino-2-fluorophenoxy)-3-chloropicolinamide (508 mg, 1.8 mmol) and HOAT (49 mg, 0.36 mmol) in DCM (15 mL) was added EDCI (518 mg, 2.7 mmol). The reaction was allowed to warm up to 50° C. and stirred overnight. The reaction was cooled down to r.t. and concentrated in vacuo. The residue was beaten by DCM/EtOAc/H₂O (20 mL/10 mL/10 mL) for 1 h. The mixture was filtered and the filter cake was dried in vacuo to afford the title compound as a yellow solid (318 mg, 33.9%).

LC-MS (ESI, pos, ion): 521.9 [M+H]$^+$;

$^1$H NMR (400 MHz, DMSO-$d_6$) δ (ppm): 10.83 (s, 1H), 8.34 (d, J=5.6 Hz, 1H), 8.06 (s, 1H), 8.02-7.92 (m, 1H), 7.75 (s, 1H), 7.59 (t, J=7.5 Hz, 2H), 7.55-7.44 (m, 3H), 7.43-7.32 (m, 2H), 6.85 (d, J=5.5 Hz, 1H), 3.58 (t, J=5.7 Hz, 2H), 3.20 (t, J=6.2 Hz, 2H), 1.98 (d, J=5.5 Hz, 2H), 1.83 (d, J=5.7 Hz, 2H).

Step 4) N-(4-((2-amino-3-chloropyridin-4-yl)oxy)-3-fluorophenyl)-2-oxo-1-phenyl-1,2,4,5,6,7-hexahydropyrazolo[1,5-a]pyridine-3-carboxamide N-(4-((2-carbamoyl-3-chloropyridin-4-yl)oxy)-3-fluorophenyl)-2-oxo-1-phenyl-1,2,4,5,6,7-hexahydropyrazolo[1,5-a]pyridine-3-carboxamide (318 mg, 0.61 mmol) in a mixture of EtOAc (8 mL), MeCN (8 mL) and H₂O (4 mL) at 0° C. was added PhI(OAc)₂ (295 mg, 0.915 mmol). The mixture was stirred at 0° C. for 0.5 h. Then the reaction was warmed up to r.t. and stirred overnight. The mixture was filtered. The filtrate was concentrated in vacuo. The residue was purified by a silica gel column chromatography (DCM/MeOH (v/v)=50/1) to give the title compound as a white solid (203.3 mg, 67.6%).

LC-MS (ESI, pos, ion): 493.9 [M+H]$^+$;

Q-TOF (ESI, pos, ion): 494.1395 [M+H]$^+$;

$^1$H NMR (600 MHz, DMSO-$d_6$) δ (ppm): 10.78 (s, 1H), 7.93 (d, J=13.3 Hz, 1H), 7.75 (d, J=5.7 Hz, 1H), 7.59 (t, J=7.7 Hz, 2H), 7.51 (t, J=7.3 Hz, 1H), 7.46 (d, J=7.8 Hz, 2H), 7.28 (t, J=6.8 Hz, 2H), 6.40 (s, 2H), 5.93 (d, J=5.7 Hz, 1H), 3.57 (t, J=5.8 Hz, 2H), 3.20 (t, J=6.3 Hz, 2H), 1.99 (dd, J=14.5, 9.1 Hz, 2H), 1.85-1.76 (m, 2H).

Biological Testing

The LC/MS/MS system used in the analysis consists of an Agilent 1200 Series vacuum degasser, binary pump, well-plate autosampler, thermostatted column compartment, the Agilent G6430 Triple Quadrupole Mass Spectrometer with an electrospray ionization (ESI) source. Quantitative analysis was carried out using MRM mode. The parameters for MRM transitions are in the Table A.

TABLE A

| MRM | 490.2→383.1 |
|---|---|
| Fragmentor | 230 V |
| CE | 55 V |
| Drying Gas Temp | 350° C. |
| Nebulize | 40 psi |
| Drying Gas Flow | 10 L/min |

An Agilent XDB-C18, 2.1×30 mm, 3.5 µM column was used for the analysis. 5 µL of the samples were injected. Analysis condition: The mobile phase was 0.1% formic acid in water (A) and 0.1% formic acid in methanol (B). The flow rate was 0.4 mL/min. And the gradient of Mobile phase was in the Table B.

TABLE B

| Time | Gradient of Mobile Phase B |
|---|---|
| 0.5 min | 5% |
| 1.0 min | 95% |
| 2.2 min | 95% |
| 2.3 min | 5% |
| 5.0 min | stop |

Alternatively, an Agilent 6330 series LC/MS/MS spectrometer equipped with G1312A binary pumps, a G1367A autosampler and a G1314C UV detector were used in the analysis. An ESI source was used on the LC/MS/MS spectrometer. The analysis was done in positive ion mode as appropriate and the MRM transition for each analyte was optimized using standard solution. A Capcell MP-C18 100× 4.6 mm I.D., 5 µM column (Phenomenex, Torrance, Calif., USA) was used during the analysis. The mobile phase was 5 mM ammonia acetate, 0.1% MeOH in water (A): 5 mM ammonia acetate, 0.1% MeOH in acetonitrile (B) (70/30, v/v). The flow rate was 0.6 mL/min. Column was maintained at ambient temperature. 20 µL of the samples were injected.

Example A

Compound Stability in Human and Rat Liver Microsomes

Human or rat liver microsomes incubations were conducted in duplicate in polypropylene tubes. The typical incubation mixtures consisted of human or rat liver microsomes (0.5 mg protein/mL), compounds of interest (5 µM) and NADPH (1.0 mM) in a total volume of 200 µL potassium phosphate buffer (PBS, 100 mM, pH 7.4). Compounds were dissolved in DMSO and diluted with PBS such that the final concentration of DMSO was 0.05%. The enzymatic reactions were commenced with the addition of protein after a 3-min preincubation and incubated in a water bath open to the air at 37° C. Reactions were terminated at various time points (0, 5, 10, 15, 30, 60 min) by adding equal volume of ice-cold acetonitrile. The samples were stored at −80° C. until LC/MS/MS assays.

The concentrations of compounds in the incubation mixtures of human or rat liver microsomes were determined by a LC/MS/MS method. The ranges of the linearity in the concentration range were determined for each tested compounds.

A parallel incubation was performed using denatured microsomes as the negative control, and reactions were terminated at various time points (0, 15, 60 min) after incubation at 37° C.

Dextromethorphan (70 µM) was selected as the positive control, and reactions were terminated at various time points (0, 5, 10, 15, 30, 60 min) after incubation at 37° C. Both positive and negative control samples were included in each assay to ensure the integrity of the microsomal incubation system.

Alternatively, the stability of some of the compounds disclosed herein in human (or rat) liver microsomes were also conducted in the following protocol. The incubations were conducted in duplicate in polypropylene tubes. The typical incubation mixtures consisted of liver microsomes (final concentration: 0.5 mg protein/mL), compounds (final concentration: 1.5 µM) in a total volume of 30 µL K-buffer (contain 1.0 mM EDTA, 100 mM, pH7.4). Compounds were dissolved in DMSO and diluted with K-buffer such that the final concentration of DMSO was 0.2%. The enzymatic reactions were commenced with the addition of 15 µL of NADPH(final concentration: 2 mM) after 10 min preincubation and incubated in a 37° C. incubator. Reactions were terminated at various time points (0, 15, 30, 60 min) by adding 135 µL acetonitrile (contain IS). Protein is removed by centrifugation with 4000 rpm, 10 min. Supernatant was collected for LCMS/MS analysis In the above protocol, ketanserin (1 µM) was selected as the positive control, and reactions were terminated at various time points (0, 15, 30, 60 min) after incubation at 37° C. The positive control sample was included in each assay to ensure the integrity of the microsomal incubation system.

Data Analysis

The concentrations of compounds in human or rat liver microsome incubations were plotted as a percentage of the relevant zero time point control for each reaction. The in vivo $CL_{int}$ were extrapolated (ref: Naritomi, Y.; Terashita, S.; Kimura, S.; Suzuki, A.; Kagayama, A.; and Sugiyama, Y.; Prediction of human hepatic clearance from in vivo animal experiments and in vitro metabolic studies with liver microsomes from animals and humans. *Drug Metab. Dispos.*, 2001, 29: 1316-1324).

Table 1 listed the stability of some examples disclosed herein in human and rat liver microsomes. As showing in Table 1, the compounds disclosed herein exhibited desirable half-life ($T_{1/2}$) and clearance ($CL_{int}$) when the compounds were incubated in human and rat liver microsomes.

TABLE 1

Human and rat liver microsomes Stability

| | Human | | Rat | |
|---|---|---|---|---|
| Example | $T_{1/2}$ (min) | $CL_{int}$ (mL/min/kg) | $T_{1/2}$ (min) | $CL_{int}$ (mL/min/kg) |
| Ex. 1 | 187.6 | 9.27 | 88.86 | 27.95 |
| Ex. 2 | 243.9 | 7.13 | 191.2 | 12.99 |
| Ex. 3 | 1931 | 0.90 | 341.9 | 7.26 |
| Ex. 12 | ∞ | NA | 998.1 | 2.49 |
| Ex. 14 | 508.1 | 3.42 | 199.2 | 12.47 |
| Ex. 19 | ∞ | NA | 172.1 | 14.43 |

Example B

Evaluation of Pharmacokinetics after Intravenous and Oral Administration of the Compounds Disclosed Herein in Mice, Rats, Dogs and Monkeys The compounds disclosed herein are assessed in pharmacokinetic studies in mice, rats, dogs or monkeys. The compounds are administered as a water solution, 2% HPMC+1% TWEEN® 80 in water solution, 5% DMSO+5% solutol in saline, 4% MC suspension or capsule. For the intravenous administration, the animals are generally given at 1 or 2 mg/kg dose. For the oral (p.o.) dosing, mice and rats are generally given 5 or 10 mg/kg dose, and dogs and monkeys are generally given 10 mg/kg dose. The blood samples (0.3 mL) are drawn at 0.25, 0.5, 1.0, 2.0, 3.0, 4.0, 6.0, 8.0, 12 and 24 h time points or 0.083, 0.25, 0.5, 1.0, 2.0, 4.0, 6.0, 8.0 and 24 h time points and centrifuged at 3,000 or 4000 rpm for 2 to 10 min. The plasma solutions are collected, and stored at −20° C. or −70° C. until analyzed by LC/MS/MS as described above.

Table 2 listed the PK profile of the compounds disclosed herein in rats. The compounds disclosed herein exhibited optimized pharmacokinetic properties with desirable clearance (CL), half-life ($T_{1/2}$), exposure ($AUC_{last}$) and bioavailability (F).

TABLE 2

Pharmacokinetic profiles in rats

| | iv dosing | | | | | |
|---|---|---|---|---|---|---|
| Example | dose mg/kg | $T_{1/2}$ h | $AUC_{last}$ ng · h/ml | Cl/F L/h/kg | Vss L/kg | F % |
| Ex. 1 | 1 | 1.51 | 1190 | 1.69 | 1.200 | 163.3 |
| Ex. 2 | 1 | 7.71 | 27200 | 0.033 | 0.313 | 68.1 |
| Ex. 3 | 1 | 3.83 | 26300 | 0.039 | 0.180 | 94.5 |
| Ex. 12 | 1 | 6.68 | 46700 | 0.020 | 0.136 | 72.1 |
| Ex. 14 | 1 | 5.01 | 12900 | 0.076 | 0.359 | 87.9 |
| Ex. 19 | 1 | 7.09 | 50100 | 0.018 | 0.150 | 66.7 |

The efficacy of the compounds disclosed herein as inhibitors of receptor tyrosine kinases, such as Axl, Mer, c-Met, and/or Ron related activity and as anti-tumor agents in xenograft animal models can be evaluated as follows. The assay results can demonstrate that certain compounds disclosed herein potently inhibit Axl, Mer, c-Met, and/or Ron phosphorylation, and demonstrate potent, dose dependent anti-tumor activity in certain xenograft models.

Example C

Kinase Activity Assay

General Description for Kinase Assays

Kinase assays can be performed by measurement of incorporation of γ-$^{33}$P ATP into immobilized myelin basic protein (MBP). High binding white 384 well plates (Greiner) are coated with MBP (Sigma #M-1891) by incubation of 60 µL/well of 20 µg/mL MBP in Tris-buffered saline (TBS; 50 mM Tris pH 8.0, 138 mM NaCl, 2.7 mM KCl) for 24 h at 4° C. Plates are washed 3× with 100 µL TBS. Kinase reactions are carried out in a total volume of 34 µL in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions are performed in DMSO and added to assay wells to a final DMSO concentration of 1%. Each data point is measured in duplicate, and at least two duplicate assays are performed for each individual compound determination. Enzyme is added to final concentrations of 10 nM or 20 nM, for example. A mixture of unlabeled ATP and γ-$^{33}$P ATP is added to start the reaction (2×10$^6$ cpm of γ-$^{33}$P ATP per well (3000 Ci/mmole) and 10 µM unlabeled ATP, typically. The reactions are carried out for 1 h at room temperature with shaking. Plates are washed 7× with TBS, followed by the addition of 50 µL/well scintillation fluid (Wallac). Plates are read using a Wallac Trilux counter. This is only one format of such assays; various other formats are possible, as known to one skilled in the art.

The above assay procedure can be used to determine the IC$_{50}$ for inhibition and/or the inhibition constant, K$_i$. The IC$_{50}$ is defined as the concentration of compound required to reduce the enzyme activity by 50% under the condition of the assay. The IC$_{50}$ value is estimated by preparing a 10 point curve using a ½ log dilution series (for example, a typical curve may be prepared using the following compound concentrations: 10 µM, 3 µM, 1 µM, 0.3 µM, 0.1 µM, 0.03 µM, 0.01 µM, 0.003 µM, 0.001 µM and 0.1 µM).

Axl (h) Assay

Axl (h) is incubated with 8 mM MOPS pH 7.0, 0.2 mM EDTA, 250 µM KKSRGDYMTMQIG, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.

Mer (h) Assay

Mer (h) is incubated with 8 mM MOPS pH 7.0, 0.2 mM EDTA, 30 mM NaCl, 250 µM GGMEDIYFEFMGGKKK, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.

c-Met (h) Assay

Met (h) is incubated with 8 mM MOPS pH 7.0, 0.2 mM EDTA, 250 µM KKKSPGEYVNIEFG, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.

The compound disclosed herein exhibited potent activities in the Mer (h) and c-Met (h) assays. Table 3 listed the IC$_{50}$s of some example described herein in the Mer (h) and c-Met (h) assay.

TABEL 3

| Example | IC₅₀ (nM) | | |
|---|---|---|---|
| | Axl | Mer | c-Met |
| Ex. 2 | / | 3 | 26 |
| Ex. 3 | / | 35 | 100 |
| Ex. 5 | 19 | 4 | 15 |
| Ex. 6 | 36 | 33 | 57 |
| Ex. 8 | 7 | 3 | 5 |
| Ex. 9 | 14 | 12 | 27 |
| Ex. 11 | 5 | 6 | 12 |
| Ex. 12 | 14 | 74 | 54 |
| Ex. 14 | 7 | 8 | 21 |
| Ex. 17 | 5 | / | 8 |
| Ex. 19 | 5 | 5 | 41 |
| Ex. 20 | 49 | 44 | / |
| Ex. 21 | 9 | / | 14 |
| Ex. 22 | 16 | / | 54 |
| Ex. 23 | 10 | 14 | 30 |

The kinase assays described herein were performed at Millipore UK Ltd, Dundee Technology Park, Dundee DD2 1SW, UK.

Alternatively, the kinase activities of the compounds can be measured using KINOMEscan™, which is based on a competition binding assay that quantitatively measures the ability of a compound to compete with an immobilized, active-site directed ligand. The assay was performed by combining three components: DNA-tagged kinase; immobilized ligand; and a test compound. The ability of the test compound to compete with the immobilized ligand was measured via quantitative PCR of the DNA tag.

For most assays, kinase-tagged T7 phage strains were prepared in an E. coli host derived from the BL21 strain. E. coli were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SEABLOCK™ (Pierce), 1% BSA, 0.05% TWEEN® 20, 1 mM DTT) to remove unbound ligand and to reduce nonspecific binding. Binding reactions were assembled by combining kinases, liganded affinity beads, and test compounds in lx binding buffer (20% SEABLOCK™, 0.17×PBS, 0.05% TWEEN® 20, 6 mM DTT). All reactions were performed in polystyrene 96-well plates in a final volume of 0.135 mL. The assay plates were incubated at room temperature with shaking for 1 hour and the affinity beads were washed with wash buffer (lx PBS, 0.05% TWEEN® 20). The beads were then re-suspended in elution buffer (lx PBS, 0.05% TWEEN® 20, 0.5 µM non-biotinylated affinity ligand) and incubated at room temperature with shaking for 30 minutes. The kinase concentration in the eluates was measured by qPCR.

The kinase activity assays described herein were performed using KINOMEscan™ Profiling Service at DiscoveRx Corporation, 42501 Albrae St. Fremont, Calif. 94538, USA.

Example D

Tumor Xenograft Models

The efficacy of compounds disclosed herein is evaluated in a standard murine model of tumorigenesis. Human tumor cells (such as U87MG glioblastoma cells, MKN45 Gastric Adenocarcinoma cells, MDA-MB-231 breast adenocarcinoma cells, or Caki-1 renal carcinoma cells, all from ATCC) are expended in culture, harvested, and injected subcutaneously in the rear flank of 6-7 week old female athymic nude mice (BALB/cA nu/nu, Shanghai SLAC Laboratory Animal, Co.) (n=10 for vehicle group, n=8 for each dosing group). When tumors reach a volume of 100-250 mm³, animals are randomly divided into vehicle control (for example, 2% HPMC+1% Tween-80 in water) and compound groups. Subsequent administration of compound by oral gavage (for example, 3-50 mpk/dose, dissolved in 2% HPMC+1% Tween-80 in water) begins anywhere from day 0 to day 15 post tumor cell challenge and generally continues with once a day for the duration of the experiment.

Tumor Growth Inhibition (TGI) Analysis

Progression of tumor growth is assessed by tumor volumes and recorded as a function of time. The long (L) and short (W) axes of the subcutaneous tumors are measured with calipers twice weekly, and the tumor volume (TV) calculated as $(L \times W^2)/2$. TGI is calculated from the difference between the median tumor volumes of vehicle-treated and drug-treated mice, expressed as a percentage of the median tumor volume of the vehicle-treated control group, by the following relation:

$$\% \ TGI = \left( \frac{\text{Median Tumor } Volume_{control} - \text{Median Tumor } Volume_{drug-related}}{\text{Median Tumor } Volume_{control}} \right) \times 100$$

Initial statistical analysis is done by repeated measures analysis of variance (RMANOVA), Followed by Scheffe post hoc testing for multiple comparisons. Vehicle alone (2% HPMC+1% Tween-80, or the like) is the negative control.

Finally, it should be noted that there are alternative ways of implementing the present invention. Accordingly, the present embodiments are to be considered as illustrative and not restrictive, and the invention is not be limited to the details given herein, but may be modified within the scope and equivalents of the appended claims. All publications and patents cited herein are incorporated by reference.

What is claimed is:

1. A compound having Formula (I):

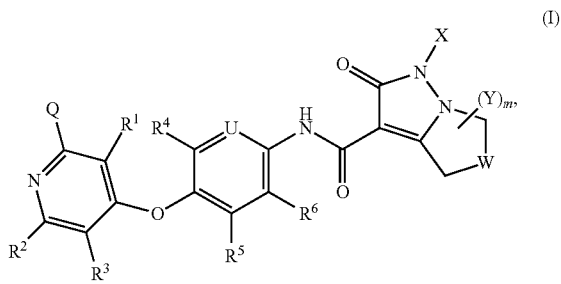

or a stereoisomer, a tautomer, an N-oxide, a solvate, a metabolite, a pharmaceutically acceptable salt or a prodrug thereof, wherein:

Q is H, OR$^a$, NR$^a$R$^b$, —C(=O)NR$^a$R$^b$, —N(R$^c$)C(=O) R$^d$, —N(R$^c$)C(=O)OR$^a$ or —N(R$^c$)C(=O)NR$^a$R$^b$;

U is CR$^7$ or N, provided that when U is N, the compound is not 2-oxo-1-phenyl-N-(5-((2-(pyrrolidine-1-carboxamido)pyridin-4-yl)oxy)pyridin-2-yl)-2,4,6,7-tetrahydro-1H-pyrazolo[5,1-c][1,4]oxazine-3-carboxamide or 1-(buta-1,3-dien-2- yl)-2-oxo-N-(5-((2-(pyrrolidine-1-carboxamido) pyridin-4-yl)oxy)pyridin-2-yl)-1,2,4,5,6,7-hexahydropyrazolo[1,5-a]pyrazine-3-carboxamide;

X is H, $C_1$-$C_6$ alkyl, $C_3$-$C_8$ alkenyl, $C_3$-$C_8$ alkynyl, $C_3$-$C_8$ cycloalkyl, —($C_1$-$C_4$ alkylene)-($C_3$-$C_8$ cycloalkyl), 3-8 membered heterocyclyl, —($C_1$-$C_4$ alkylene)-(3-8 membered heterocyclyl), $C_6$-$C_{10}$ aryl, —($C_1$-$C_4$ alkylene)-($C_6$-$C_{10}$ aryl), 5-10 membered heteroaryl or —($C_1$-$C_4$ alkylene)-(5-10 membered heteroaryl), wherein each of the $C_1$-$C_6$ alkyl, $C_3$-$C_8$ alkenyl, $C_3$-$C_8$ alkynyl, $C_3$-$C_8$ cycloalkyl, —($C_1$-$C_4$ alkylene)-($C_3$-$C_8$ cycloalkyl), 3-8 membered heterocyclyl, —($C_1$-$C_4$ alkylene)-(3-8 membered heterocyclyl), $C_6$-$C_{10}$ aryl, —($C_1$-$C_4$ alkylene)-($C_6$-$C_{10}$ aryl), 5-10 membered heteroaryl and —($C_1$-$C_4$ alkylene)-(5-10 membered heteroaryl) is optionally substituted with 1, 2, 3, 4 or 5 substituents independently selected from F, Cl, Br, CN, $C_1$-$C_6$ alkyl, $C_2$-$C_6$ alkenyl, $C_2$-$C_6$ alkynyl, $OR^a$, $NR^aR^b$, —($C_1$-$C_4$ alkylene)-$OR^a$ and —($C_1$-$C_4$ alkylene)-$NR^aR^b$;

each Y is independently $C_1$-$C_6$ alkyl, $C_2$-$C_6$ alkenyl, $C_2$-$C_6$ alkynyl, $C_3$-$C_8$ cycloalkyl, —($C_1$-$C_4$ alkylene)-($C_3$-$C_8$ cycloalkyl), 3-8 membered heterocyclyl, —($C_1$-$C_4$ alkylene)-(3-8 membered heterocyclyl), $C_6$-$C_{10}$ aryl, —($C_1$-$C_4$ alkylene)-($C_6$-$C_{10}$ aryl), 5-10 membered heteroaryl, —($C_1$-$C_4$ alkylene)-(5-10 membered heteroaryl), $OR^a$, $NR^aR^b$, —($C_1$-$C_4$ alkylene)-$OR^a$ or —($C_1$-$C_4$ alkylene)-$NR^aR^b$;

m is 0, 1, 2, 3, 4;

W is —$(CH_2)_n$—, —$(CH_2)_nO$—, —$(CH_2)_nNH$— or —$(CH_2)_nS$—, wherein n is 0, 1, 2, 3 or 4;

each of $R^1$, $R^2$, $R^3$, $R^4$, $R^5$, $R^6$ and $R^7$ is independently H, F, Cl, Br, CN, $N_3$, $OR^a$, $C_1$-$C_6$ alkyl, $C_1$-$C_6$ haloalkyl, $C_2$-$C_6$ alkenyl or $C_2$-$C_6$ alkynyl;

each of $R^a$, $R^b$ and $R^c$ is independently H, $C_1$-$C_6$ alkyl, $C_1$-$C_6$ haloalkyl, $C_3$-$C_6$ cycloalkyl, —($C_1$-$C_4$ alkylene)-($C_3$-$C_6$ cycloalkyl), 3-6 membered heterocyclyl, —($C_1$-$C_4$ alkylene)-(3-6 membered heterocyclyl), $C_6$-$C_{10}$ aryl, —($C_1$-$C_4$ alkylene)-($C_6$-$C_{10}$ aryl), 5-10 membered heteroaryl or —($C_1$-$C_4$ alkylene)-(5-10 membered heteroaryl), or $R^a$ and $R^b$ taken together with the nitrogen atom to which they are attached form a 3-8 membered heterocyclic ring, wherein each of the $C_1$-$C_6$ alkyl, $C_1$-$C_6$ haloalkyl, $C_3$-$C_6$ cycloalkyl, —($C_1$-$C_4$ alkylene)-($C_3$-$C_6$ cycloalkyl), 3-6 membered heterocyclyl, —($C_1$-$C_4$ alkylene)-(3-6 membered heterocyclyl), $C_6$-$C_{10}$ aryl, —($C_1$-$C_4$ alkylene)-($C_6$-$C_{10}$ aryl), 5-10 membered heteroaryl, —($C_1$-$C_4$ alkylene)-(5-10 membered heteroaryl) and 3-8 membered heterocyclic ring is optionally substituted with 1, 2, 3 or 4 substituents independently selected from F, Cl, CN, $N_3$, OH, $NH_2$, $C_1$-$C_6$ haloalkyl, $C_1$-$C_6$ alkoxy and $C_1$-$C_6$ alkylamino; and $R^d$ is H, $C_1$-$C_6$ alkyl, $C_3C_8$ cycloalkyl, —($C_1$-$C_4$ alkylene)-($C_3$-$C_8$ cycloalkyl), 3-8 membered heterocyclyl, —($C_1$-$C_4$ alkylene)-(3-8 membered heterocyclyl), $C_6$-$C_{10}$ aryl, —($C_1$-$C_4$ alkylene)-($C_6$-$C_{10}$ aryl), 5-10 membered heteroaryl or —($C_1$-$C_4$ alkylene)-(5-10 membered heteroaryl), wherein each of the $C_1$-$C_6$ alkyl, $C_3$-$C_8$ cycloalkyl, —($C_1$-$C_4$ alkylene)-($C_3$-$C_8$ cycloalkyl), 3-8 membered heterocyclyl, —($C_1$-$C_4$ alkylene)-(3-8 membered heterocyclyl), $C_6$-$C_{10}$ aryl, —($C_1$-$C_4$ alkylene)-($C_6$-$C_{10}$ aryl), 5-10 membered heteroaryl and —($C_1$-$C_4$ alkylene)-(5-10 membered heteroaryl) is optionally substituted with 1, 2, 3 or 4 substituents independently selected from F, Cl, CN, $OR^a$, $NR^aR^b$, $C_1$-$C_6$ alkyl, $C_2$-$C_6$ alkenyl, $C_2$-$C_6$ alkynyl, —($C_1$-$C_4$ alkylene)-$OR^a$ and —($C_1$-$C_4$ alkylene)-$NR^aR^b$.

2. The compound of claim 1, wherein X is $C_1$-$C_4$ alkyl, $C_3$-$C_6$ alkenyl, $C_3$-$C_6$ alkynyl, $C_3$-$C_6$ cycloalkyl, —($C_1$-$C_2$ alkylene)-($C_3$-$C_6$ cycloalkyl), phenyl or —($C_1$-$C_2$ alkylene)-phenyl, wherein each of the $C_1$-$C_4$ alkyl, $C_3$-$C_6$ alkenyl, $C_3$-$C_6$ alkynyl, $C_3$-$C_6$ cycloalkyl, —($C_1$-$C_2$ alkylene)-($C_3$-$C_6$ cycloalkyl), phenyl and —($C_1$-$C_2$ alkylene)-phenyl is optionally substituted with 1, 2, 3, 4 or 5 substituents independently selected from F, Cl, Br, CN, $C_1$-$C_4$ alkyl, $C_2$-$C_4$ alkenyl, $C_2$-$C_4$ alkynyl, $OR^a$, $NR^aR^b$, —($C_1$-$C_2$ alkylene)-$OR^a$ and —($C_1$-$C_2$ alkylene)-$NR^aR^b$.

3. The compound of claim 1, wherein each Y is independently $C_1$-$C_6$ alkyl, $C_2$-$C_6$ alkenyl, $C_2$-$C_6$ alkynyl, $C_3$-$C_6$ cycloalkyl, —($C_1$-$C_2$ alkylene)-($C_3$-$C_6$ cycloalkyl), 3-6 membered heterocyclyl, —($C_1$-$C_2$ alkylene)-(3-6 membered heterocyclyl), phenyl, —($C_1$-$C_2$ alkylene)-phenyl, 5-6 membered heteroaryl, —($C_1$-$C_2$ alkylene)-(5-6 membered heteroaryl), $OR^a$, $NR^aR^b$, —($C_1$-$C_2$ alkylene)-$OR^a$ or —($C_1$-$C_2$ alkylene)-$NR^aR^b$; m is 0, 1 or 2.

4. The compound of claim 1, wherein each of $R^1$, $R^2$, $R^3$, $R^4$, $R^5$, $R^6$ and $R^7$ is independently H, F, Cl, Me or OMe.

5. The compound of claim 1, wherein each of $R^a$, $R^b$ and $R^c$ is independently H, $C_1$-$C_4$ alkyl, $C_1$-$C_4$ haloalkyl, $C_3$-$C_6$ cycloalkyl, —($C_1$-$C_2$ alkylene)-($C_3$-$C_6$ cycloalkyl), 3-6 membered heterocyclyl or —($C_1$-$C_2$ alkylene)-(3-6 membered heterocyclyl), or $R^a$ and $R^b$ taken together with the nitrogen atom to which they are attached form a 3-8 membered heterocyclic ring, wherein each of the $C_1$-$C_4$ alkyl, $C_1$-$C_4$ haloalkyl, $C_3$-$C_6$ cycloalkyl, —($C_1$-$C_2$ alkylene)-($C_3$-$C_6$ cycloalkyl), 3-6 membered heterocyclyl, —($C_1$-$C_2$ alkylene)-(3-6 membered heterocyclyl) and 3-8 membered heterocyclic ring is optionally substituted with 1, 2, 3 or 4 substituents independently selected from F, Cl, CN, $N_3$, OH, $NH_2$, $C_1$-$C_3$ haloalkyl, $C_1$-$C_3$ alkoxy and $C_1$-$C_3$ alkylamino.

6. The compound of claim 1, wherein $R^d$ is H, $C_1$-$C_4$ alkyl, $C_3$-$C_6$ cycloalkyl, —($C_1$-$C_2$ alkylene)-($C_3$-$C_6$ cycloalkyl), 3-6 membered heterocyclyl or —($C_1$-$C_2$ alkylene)-(3-6 membered heterocyclyl), wherein each of the $C_1$-$C_4$ alkyl, $C_3$-$C_6$ cycloalkyl, —($C_1$-$C_2$ alkylene)-($C_3$-$C_6$ cycloalkyl), 3-6 membered heterocyclyl and —($C_1$-$C_2$ alkylene)-(3-6 membered heterocyclyl) is optionally substituted with 1, 2, 3 or 4 substituents independently selected from F, CN, $OR^a$, $NR^aR^b$, $C_1$-$C_4$ alkyl, $C_2$-$C_4$ alkenyl, $C_2$-$C_4$ alkynyl, —($C_1$-$C_2$ alkylene)-$OR^a$ and —($C_1$-$C_2$ alkylene)-$NR^aR^b$.

7. The compound of claim 1, wherein Q is:

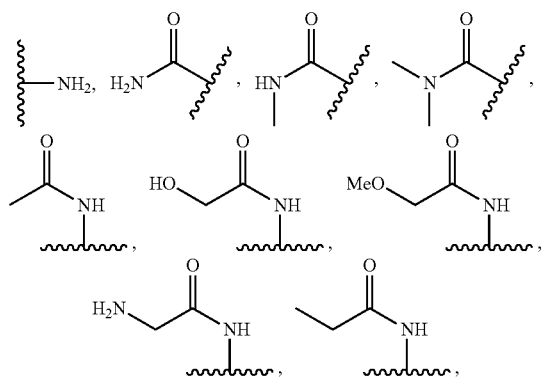

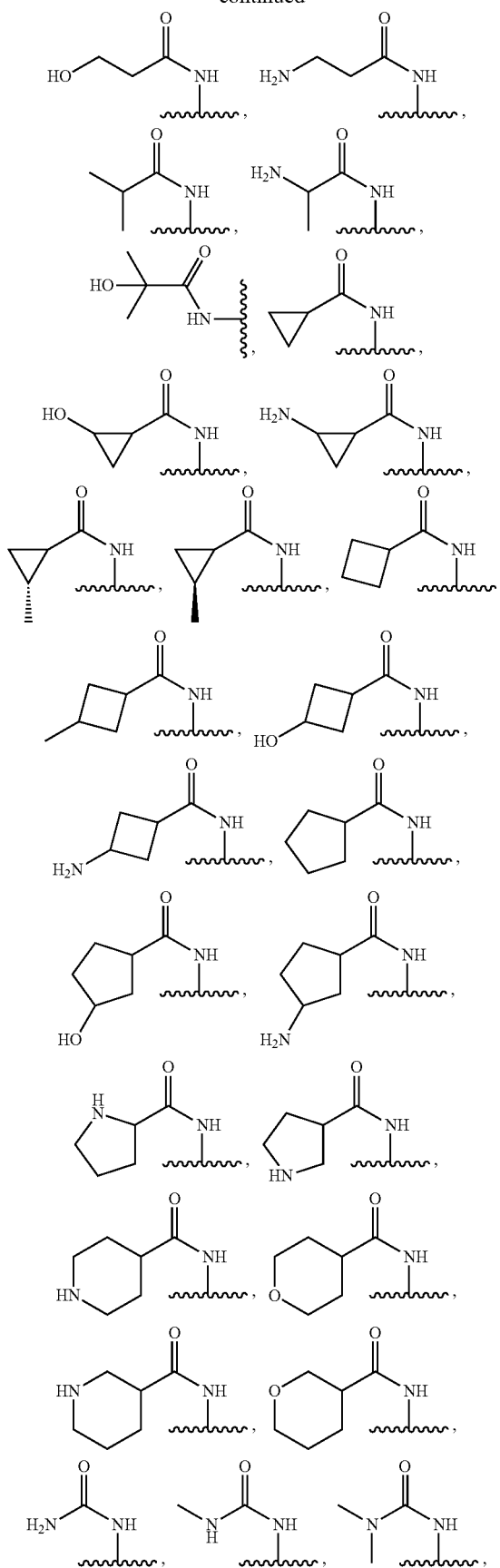
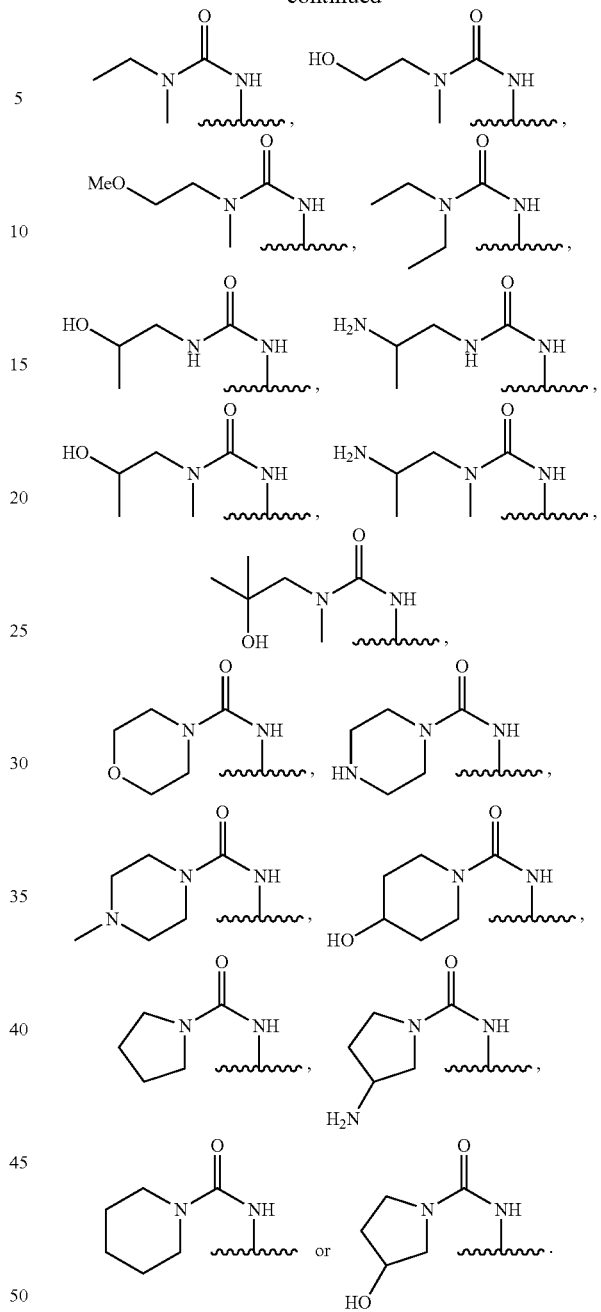
8. The compound of claim 1 having one of the following structures:
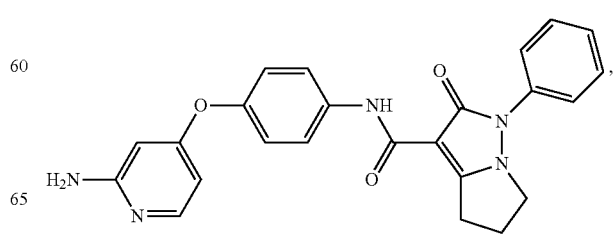

(2)
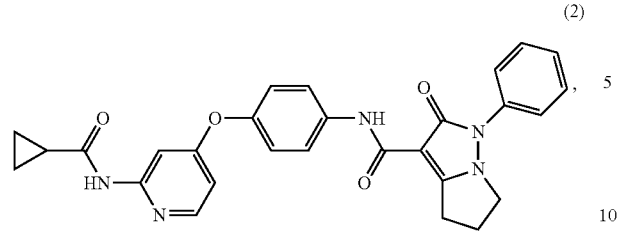
(3)
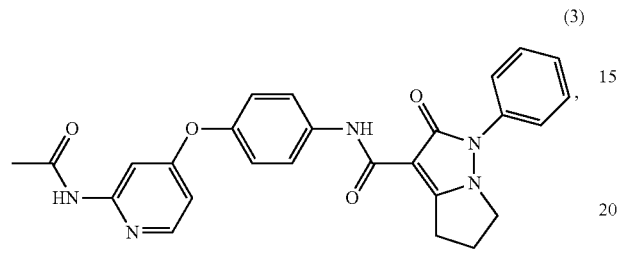
(4)
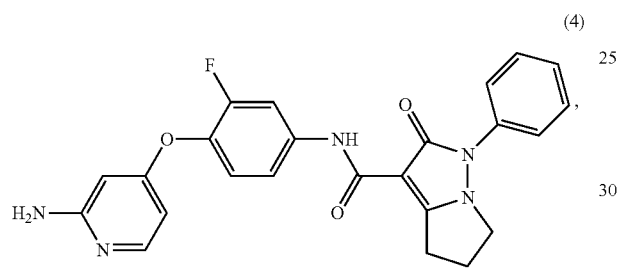
(5)
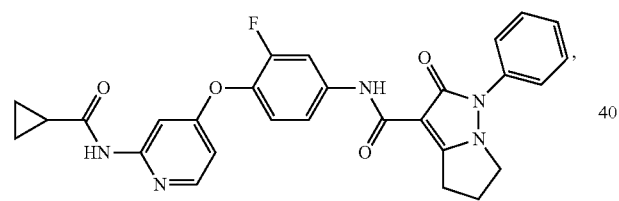
(6)
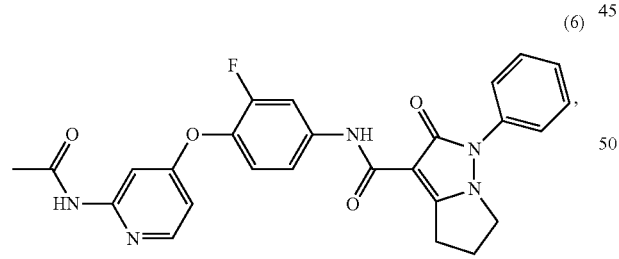
(7)
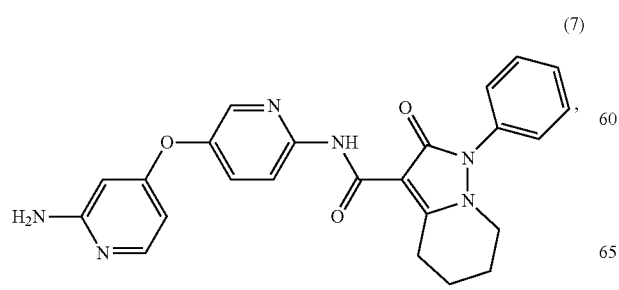
(8)
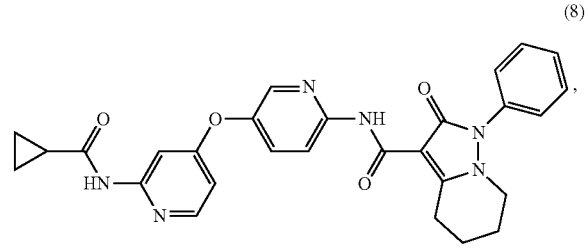
(9)
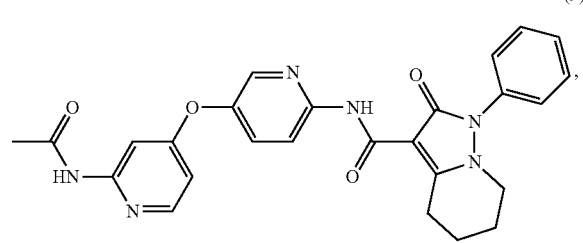
(10)
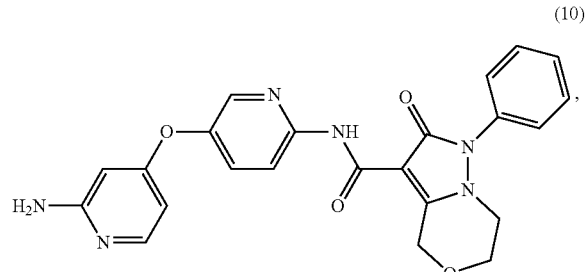
(11)
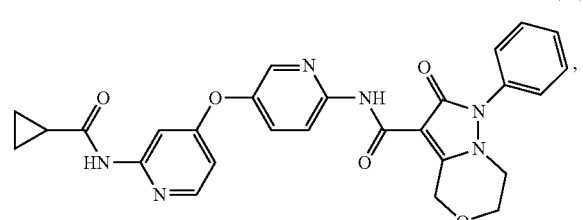
(12)
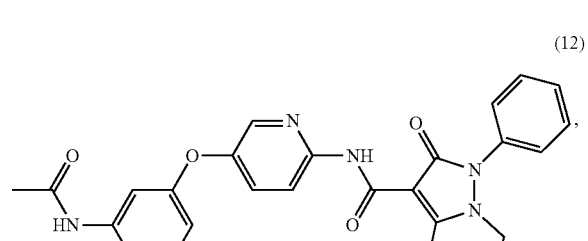
(13)
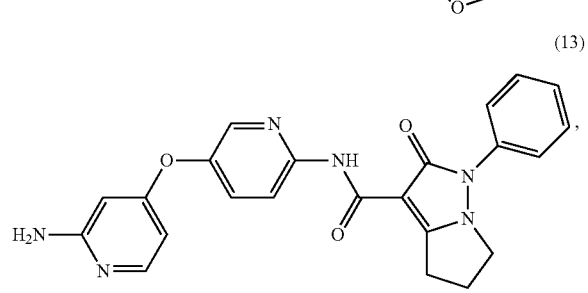

(14)
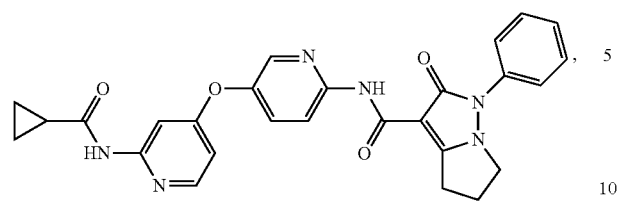
(15)
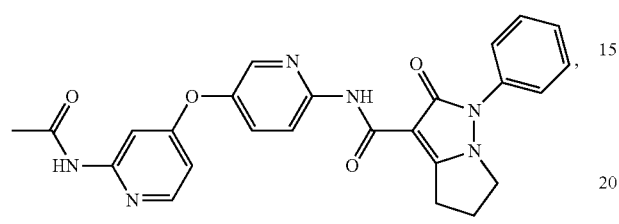
(16)
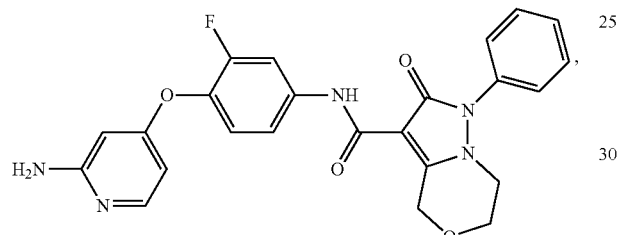
(17)
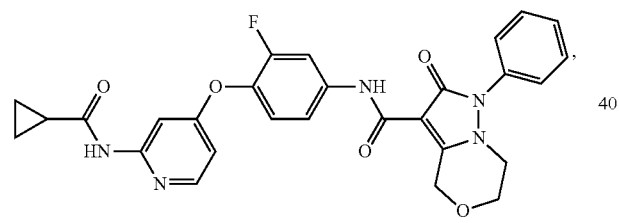
(18)
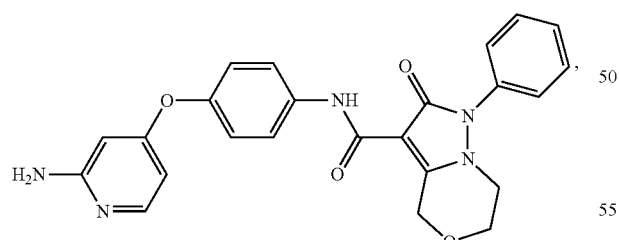
(19)
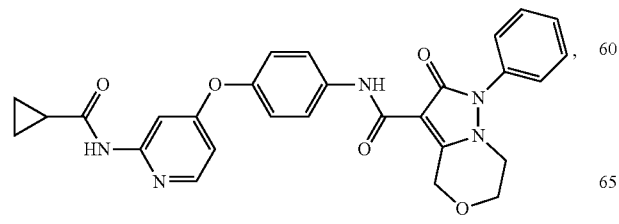
(20)
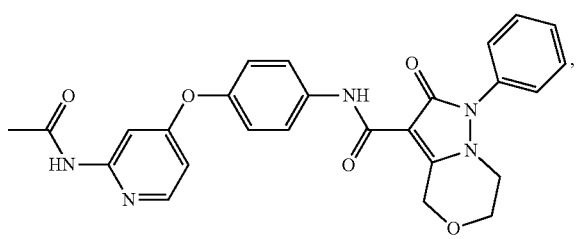
(21)
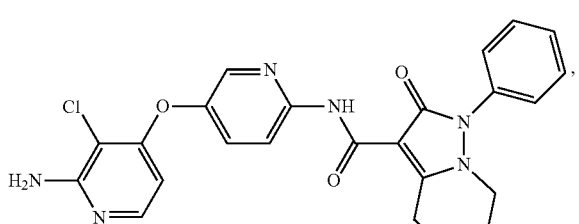
(22)
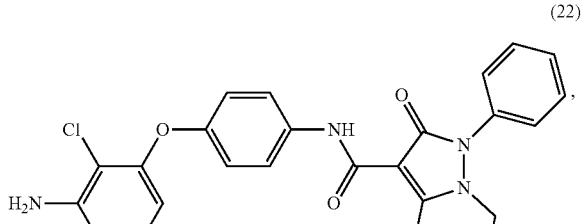
(23)
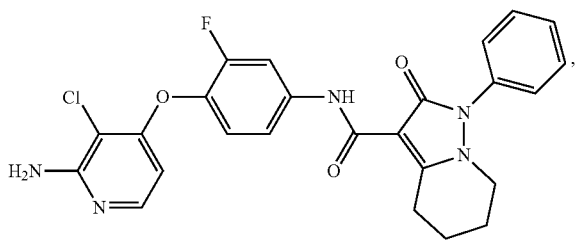
(24)
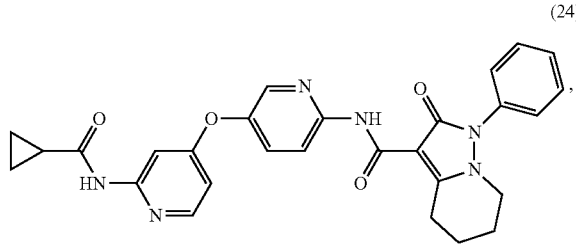
(25)
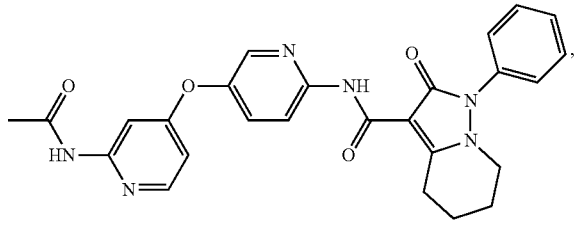

(26) 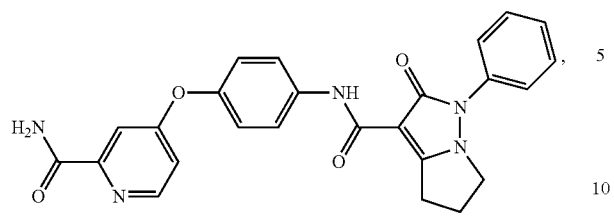
(27) 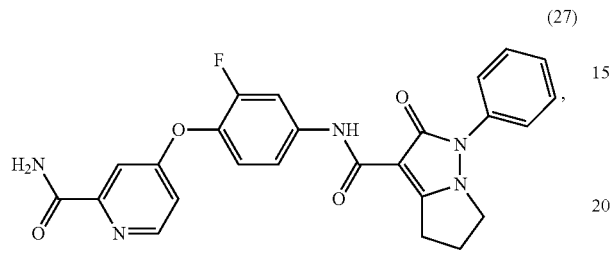
(28) 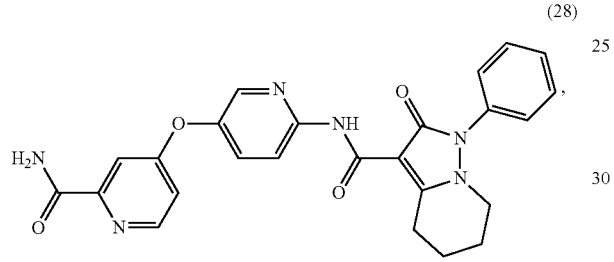
(29) 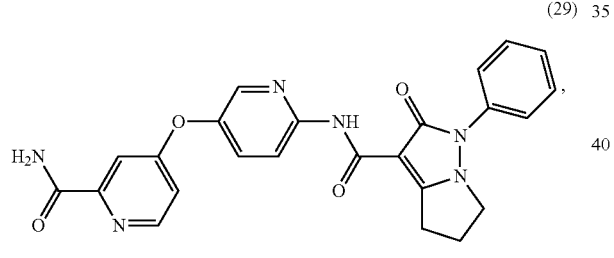
(30) 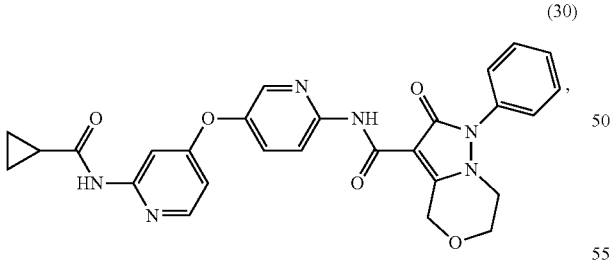
(31) 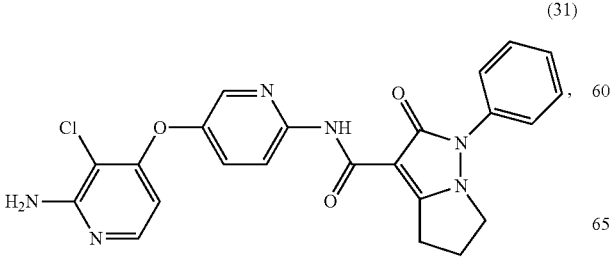
(32) 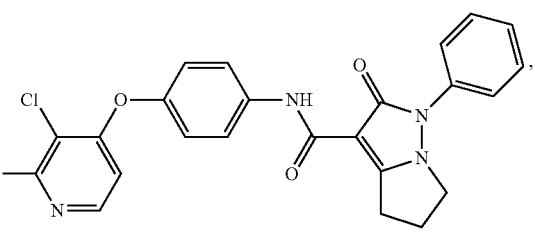
(33) 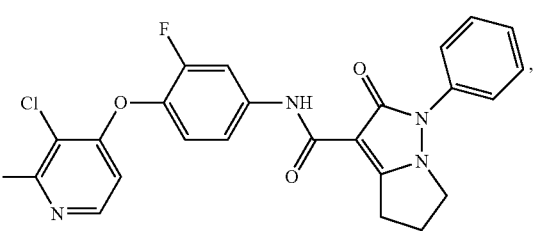
(34) 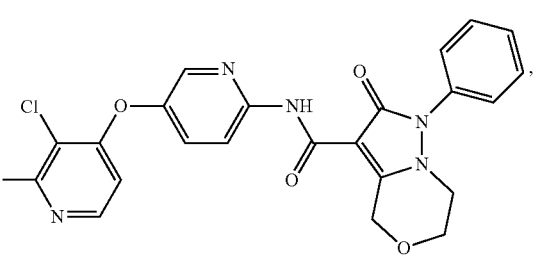
(35) 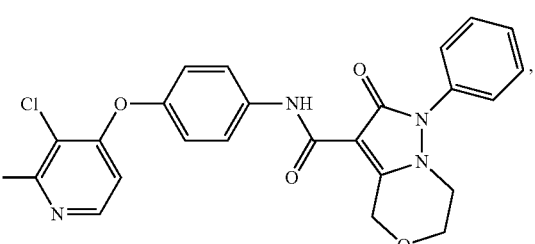
(36) 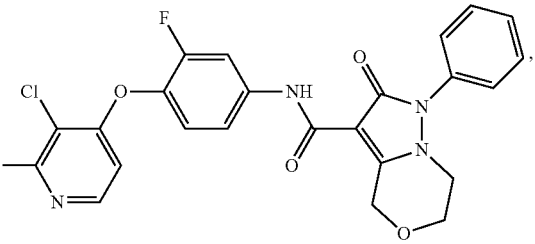
(37) 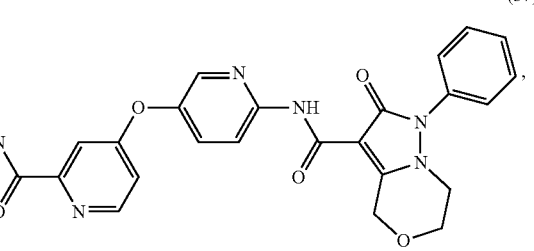

-continued

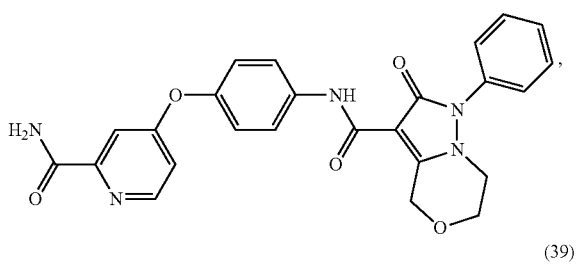 (38)

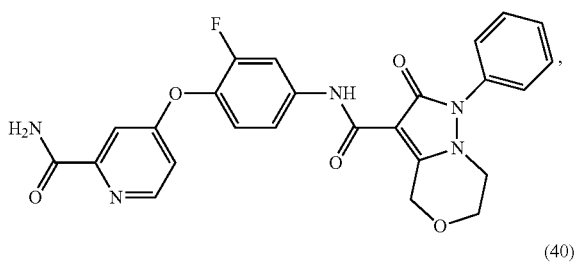 (39)

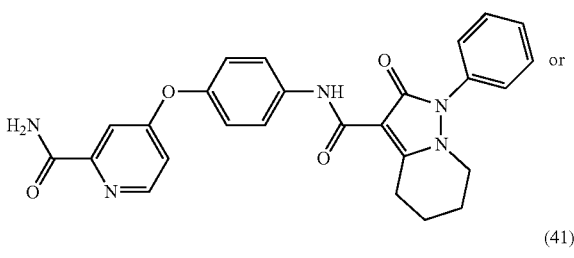 (40) or

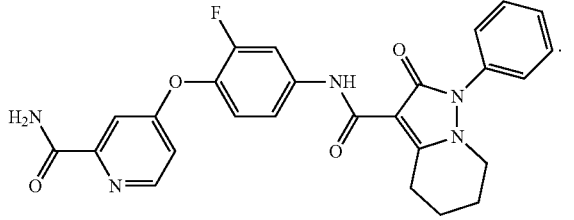 (41)

9. A pharmaceutical composition comprising the compound according to claim 1, and a pharmaceutically acceptable excipient, carrier, adjuvant, vehicle or a combination thereof.

10. The pharmaceutical composition of claim 9 further comprising a therapeutic agent selected from the group consisting of chemotherapeutic agents, anti-proliferative agents, agents for treating atherosclerosis, agents for treating lung fibrosis and combinations thereof.

11. The pharmaceutical composition of claim 10, wherein the therapeutic agent is chlorambucil, melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednisone, dexamethasone, methylprednisolone, thalidomide, interferon alfa, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximabvedotin, catumaxomab, cetuximab, denosumab, gemtuzumab, ipilimumab, nimotuzumab, ofatumumab, panitumumab, ramucirumab, rituximab, tositumomab, trastuzumab or a combination thereof.

12. A method of treating or lessening the severity of a proliferative disease in a patient by administering to the patient with a therapeutically effective amount of the compound according to claim 1, wherein the proliferative disease is atherosclerosis, lung fibrosis, colon cancer, rectal cancer, gastric cancer, gastric adenocarcinoma, pancreatic cancer, bladder cancer, gallbladder cancer, breast cancer, kidney cancer, renal cell carcinoma, liver cancer, hepatocellular carcinoma, lung cancer, skin cancer, melanoma, thyroid cancer, osteosarcomas, soft tissue sarcoma, a cancer of the head and neck, a cancer of the central nervous system, glioma, glioblastomas, ovarian cancer, uterine cancer, endometrial carcinoma, prostate cancer, acute myeloid leukemia or acute lymphoblastic leukemia, or a metastasis thereof.

13. A method of inhibiting or modulating the activity of a protein kinase in a biological sample comprising contacting the biological sample with the compound according to claim 1.

14. The method of claim 13, wherein the protein kinase is a receptor tyrosine kinase.

15. The method of claim 14, wherein the receptor tyrosine kinase is Axl, Mer, c-Met, Ron or a combination thereof.

16. A method of treating or lessening the severity of a proliferative disease in a patient by administering to the patient with a therapeutically effective amount of the pharmaceutical composition according to claim 9, wherein the proliferative disease is atherosclerosis, lung fibrosis, colon cancer, rectal cancer, gastric cancer, gastric adenocarcinoma, pancreatic cancer, bladder cancer, gallbladder cancer, breast cancer, kidney cancer, renal cell carcinoma, liver cancer, hepatocellular carcinoma, lung cancer, skin cancer, melanoma, thyroid cancer, osteosarcomas, soft tissue sarcoma, a cancer of the head and neck, a cancer of the central nervous system, glioma, glioblastomas, ovarian cancer, uterine cancer, endometrial carcinoma, prostate cancer, acute myeloid leukemia or acute lymphoblastic leukemia, or a metastasis thereof.

17. A method of inhibiting or modulating the activity of a protein kinase in a biological sample comprising contacting the biological sample with the pharmaceutical composition according to claim 9.

18. The method of claim 17, wherein the protein kinase is a receptor tyrosine kinase.

19. The method of claim 18, wherein the receptor tyrosine kinase is Axl, Mer, c-Met, Ron or a combination thereof.

* * * * *